US010842794B2

(12) United States Patent
Fekete et al.

(10) Patent No.: US 10,842,794 B2
(45) Date of Patent: Nov. 24, 2020

(54) USE OF SIGMA-1 RECEPTOR AGONIST COMPOUNDS

(71) Applicants: MTA TÁMOGATOTT KUTATÓCSOPORTOK IRODÁJA, Budapest (HU); SEMMELWEIS EGYETEM, Budapest (HU); SigmaDrugs Kft., Budapest (HU)

(72) Inventors: Andrea Fekete, Budapest (HU); Ádám Vannay, Budapest (HU); Endre Illés Kovács, Budapest (HU)

(73) Assignees: Támogatott Kutatócsoportok Irodája, Budapest (HU); Semmelweis Egyetem, Budapest (HU); SigmaDrugs Kft., Budapest (HU)

( * ) Notice: Subject to any disclaimer, the term of this patent is extended or adjusted under 35 U.S.C. 154(b) by 0 days.

(21) Appl. No.: 16/360,375

(22) Filed: Mar. 21, 2019

(65) Prior Publication Data
US 2019/0209575 A1 Jul. 11, 2019

Related U.S. Application Data

(60) Continuation-in-part of application No. 16/185,318, filed on Nov. 9, 2018, now abandoned, which is a division of application No. 15/117,233, filed as application No. PCT/HU2015/000014 on Feb. 9, 2015, now Pat. No. 10,124,006.

(30) Foreign Application Priority Data

Feb. 7, 2014 (EP) .................... 14462004

(51) Int. Cl.
A61K 31/5375 (2006.01)
A61K 31/4985 (2006.01)
A61K 31/495 (2006.01)
A61K 31/4515 (2006.01)
A61K 31/4468 (2006.01)
A61K 31/4453 (2006.01)
A61K 31/135 (2006.01)
A61K 31/341 (2006.01)
A61K 31/215 (2006.01)
A61K 31/15 (2006.01)
A61K 31/138 (2006.01)
A61K 31/402 (2006.01)

(52) U.S. Cl.
CPC ........ A61K 31/5375 (2013.01); A61K 31/135 (2013.01); A61K 31/138 (2013.01); A61K 31/15 (2013.01); A61K 31/215 (2013.01); A61K 31/341 (2013.01); A61K 31/402 (2013.01); A61K 31/4453 (2013.01); A61K 31/4468 (2013.01); A61K 31/4515 (2013.01); A61K 31/495 (2013.01); A61K 31/4985 (2013.01)

(58) Field of Classification Search
CPC ............ A61K 31/5375; A61K 31/4985; A61K 31/495; A61K 31/4515; A61K 31/4468; A61K 31/402; A61K 31/135; A61K 31/341; A61K 31/215; A61K 31/15; A61K 31/138; A61K 31/4453
See application file for complete search history.

(56) References Cited

U.S. PATENT DOCUMENTS

| 6,500,835 B2 | 12/2002 | Fukami et al. | |
| 2006/0063809 A1 | 3/2006 | Lee et al. | |
| 2006/0111375 A1 | 5/2006 | Shimizu et al. | |
| 2010/0285139 A1* | 11/2010 | Gulbins | A61K 31/00 424/489 |
| 2011/0288101 A1* | 11/2011 | Wang | A61K 45/06 514/252.12 |
| 2011/0288134 A1 | 11/2011 | Maksumova et al. | |
| 2012/0040004 A1 | 2/2012 | Howard et al. | |
| 2015/0031723 A1 | 1/2015 | Cao | |

FOREIGN PATENT DOCUMENTS

WO 2009/016227 A2 2/2009

OTHER PUBLICATIONS

C.E.Wainwright, New England Journal of Medicine, 220-231 (2015).*
P. Anderson, Therapeutic Advances in Respiratory Disease, 177-185 (2010).*
Armendáriz-Borunda et al.: "A pilot study in patients with established advanced liver fibrosis using pirfenidone", Gut, 2006, vol. 55(11), pp. 1663-1665.
Azuma: "Pirfenidone: antifibrotic agent for idiopathic pulmonary fibrosis", Expert Review of Respiratory Medicine, 2010, vol. 4(3), abstract.
Cho et al.: "Pirfenidone: an anti-fibrotic and cytoprotective agent as therapy for progressive kidney disease", Expert Opin Investig Drugs, 2010, vol. 19(2), pp. 275-283.
Gayraud et al.: "Raynaud's phenomenon", Joint Bone Spine, 2007, vol. 74(1), pp. e1-e8.
Hashimoto: "Sigma-1 receptor chaperone and brain-derived neurotrophic factor: Emerging links between cardiovascular disease and depression", Progress in Neurobiology, 2013, vol. 100, pp. 15-29.
Hinz et al.: "Fibrosis: recent advances in myofibroblast biology and new therapeutic perspectives", F1000 Biol Rep., 2010, vol. 2:78, pp. 1-5.
Ishikawa et al.: "The role of sigma-1 receptors in the pathophysiology of neuropsychiatric diseases", Journal of Receptor, Ligand and Channel Research, 2010, vol. 3, pp. 25-36.

(Continued)

Primary Examiner — Mark L Shibuya
Assistant Examiner — Ebenezer O Sackey
(74) Attorney, Agent, or Firm — Jason D. Voight

(57) ABSTRACT

Compositions and methods for the prevention, inhibition, and/or treatment of progressive fibrosis present in various fibroproliferative disorders. Embodiments relate to the use of Sigma-1 receptor agonists for use in the treatment of prevention of progressive fibrosis characterized by the over proliferation of ECM producing cells, e.g. myofibroblasts and by the excessive deposition of ECM components in a medical or disease condition. Preferred Sigma-1 agonists are disclosed.

11 Claims, 22 Drawing Sheets

Specification includes a Sequence Listing.

(56) References Cited

OTHER PUBLICATIONS

Karihaloo: "Anti-fibrosis therapy and diabetic nephropathy", Curr Diab Rep., 2012, vol. 12(4), abstract.
Lekkerkerker et al.: "Cellular players in lung fibrosis", Curr Pharm Des., 2012, vol. 18(27), abstract.
Paz et al.: "Antifibrosis: to reverse the irreversible", Clin Rev Allergy Immunol., 2010, vol. 38(2-3), abstract.
Schaefer et al.: "Antifibrotic activities of pirfenidone in animal models", Eur Respir Rev, 2011, vol. 20(120), pp. 85-97.
See et al.: "Early and Delayed Tranilast Treatment Reduces Pathological Fibrosis Following Myocardial Infarction", Heart Lung Circ., 2013, vol. 22(2), abstract.
Tagashira et al.: "Cardioprotective effect of Fluvoxamine, Sigma-1 Receptor High Affinity Agonist", Yakugaku Zasshi: Journal of the Pharmaceutical Society of Japan, 2012, vol. 132(2), pp. 167-172.
Li et al.: "Fluoxetine inhibited extracellular matrix of pulmonary artery and intlammation of lungs in monocrotaline-treated rats", Acta Pharmacologica Sinica, 2011, vol. 32(2), pp. 217-222.
Dumas et al.: "Molecular interactions involving organic halides", Halides, Pseudo-Halides and Azides, 1983, Chapter 21, pp. 985-1020.
Egashira et al.: "Involvement of the sigma1 receptor in inhibiting activity of fluvoxamine on marble-burying behavior. Comparison with paroxetine", European Journal of Pharmacology, 2007, vol. 563, pp. 149-154.
Hyrskyluoto et al.: "Sigma-1 receptor agonist PRE084 is protective against mutant huntingtin-induced cell degeneratio: involvement of calpastatin and the NK-kB pathway", Cell Death and Disease, 2013, vol. 4, pp. 1-9.
Kobayashi et al.: "Enhancement of Acetylcholine Release by SA4503, a Novel sigma1 Receptor Agonist, in the Rat Brain", Journal of Pharmacology and Experimental Therapeutics, 1996, vol. 279, pp. 106-113.
Ono et al.: "A sigma-1 receptor antagonist (NE-100) prevents tunicamycin-induced cell death via GRP78 induction in hippocampal cells", Biochemical and Biophysical Research Communications, 2013, vol. 434, pp. 904-909.
Oxford English Language Dictionary, "pseudohalogen", (3rd ed., Sep. 2007).
Becker et al.: "Acid Sphingomyelinase Inhibitors Normalize Pulmonary Ceramide and Inflammation in Cystic Fibrosis", Am J Respir Cell Mol Biol, 2009, vol. 42, pp. 716-724.
Dygai et al.: "Antifibrotic Effect of Combined Treatment with Neuroleptic Drug and Immobilized Hyaluronidase in Pulmonary Fibrosis", Bulletin of Experimental Biology and Medicine, 2013, vol. 154(3), pp. 329-333.
Friedlander: "Fibrosis and diseases of the eye", The Journal of Clinical Investigation, 2007, vol. 117(3), pp. 576-586.
Hanner et al.: "Purification, molecular cloning, and expression of the mammalian sigma1-binding site", Proc Natl Acad Sci USA, vol. 93(15), pp. 8072-8077.
Hill et al.: "Decorin treatment for reversing trabecular meshwork fibrosis in open-angle glaucoma", Neural Regen Res., 2016, vol. 11(6), pp. 922-923.
McDonnell et al.: "The Role of Epigenetics in the Fibrotic Processes Associated with Glaucoma", Journal of Ophthalmology, 2014, Article ID 750459, 13 pages.
Montecchi-Palmer et al.: "TGFb2 Induces the Formation of Cross-Linked Actin Networks (CLANs) in Human Trabecular Meshwork Cells Through the Smad and Non-Smad Dependent Pathways", Glaucoma, 2017, vol. 58(2), pp. 1288-1295.
Niiitsu et al.: "Sigma-1 Receptor Agonists as Therapeutic Drugs for Cognitive Impairment in Neuropsychiatric Diseases", Curr Pharm Des., 2012, vol. 18(7), pp. 875-883.
Patel: "Ocular drug delivery systems: An overview", World J Pharmacol., 2013, vol. 2(2), pp. 47-64.
Stamer et al.: "The many faces of the trabecular meshwork cell", Exp Eye Res., 2017, vol. 158, pp. 112-123.
Yu-Wai-Man et al.: "Personalized Medicine in Ocular Fibrosis: Myth or Future Biomarkers", Adv Wound Care (New Rochelle), 2016, vol. 5(9), pp. 390-402.
Vagnerova et al.: "Sigma 1 Receptor Agonists Act as Neuroprotective Drugs Through Inhibition of Inducible Nitric Oxide Synthase", Anesthesia & Analgesia, 2006, vol. 103(2), pp. 430-434.
Anavex Life Sciences Corp.: "Anavex Encouraged by Scientific Data Confirming Sigma-1 Receptor Agonist is Potentially Disease-Modifying in Parkinson's Disease", Globe Newswire, 2014, New York.

\* cited by examiner

*p<0.05 vs. Control

*p<0.0001 vs. Control; +p<0.0001 vs. C + PDGF;
§p<0.01 vs. PDGF + 10 µM FLU + NE100

*p<0.0001 vs. Control; +p<0.05 vs. PDGF;
§p<0.0001 vs. PDGF

*p<0.0001 vs. Control; #p<0.005 vs. PDGF

*p<0.0001 vs. Control; # p<0.05 vs. TGF; +p<0.001 vs. TGF

*p<0.0001 vs. Control; +p<0.05 vs. TGF

*p<0.0001 vs. Control; +p<0.05 vs. TGF;

$*p<0.0001$ vs. Control; $+p<0.0001$ vs. D; $§p<0.0001$ vs. D + FLU + NE100

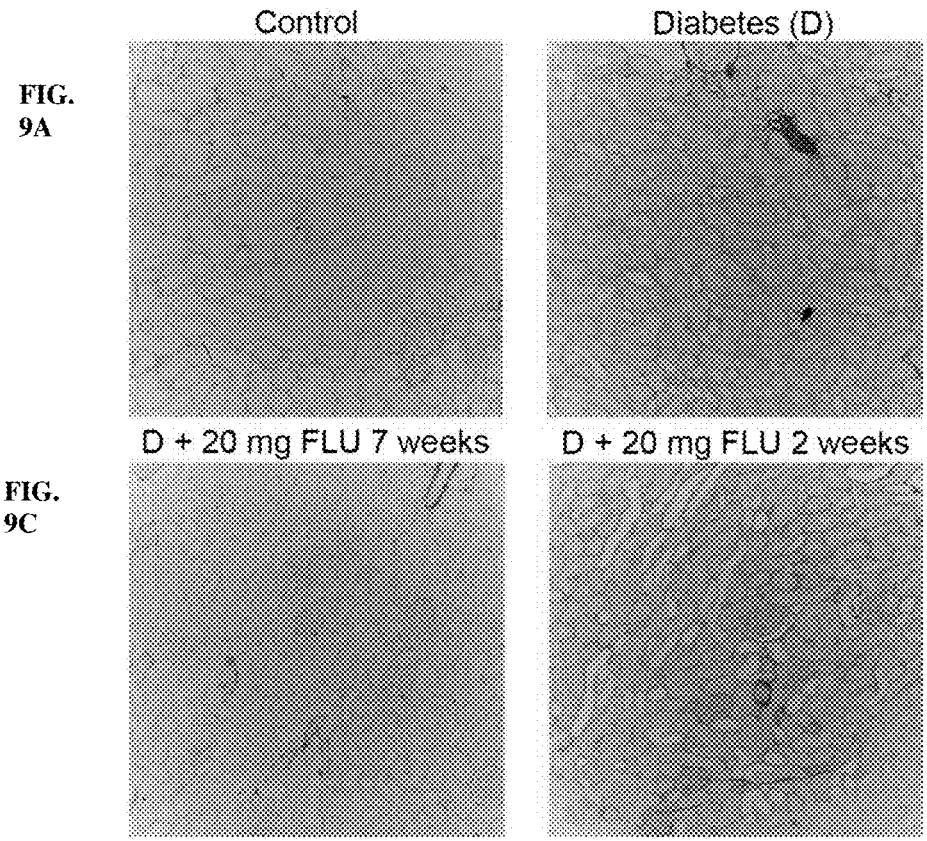
FIG. 9A — Control
FIG. 9B — Diabetes (D)
FIG. 9C — D + 20 mg FLU 7 weeks
FIG. 9D — D + 20 mg FLU 2 weeks
FIG. 9E
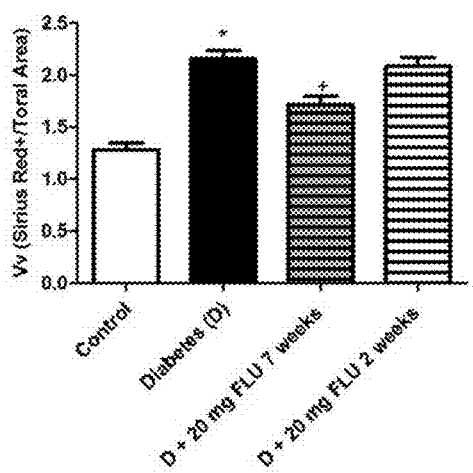
Diabetes induced ECM production
*$p<0.0001$ vs. Control; +$p<0.0001$ vs. Diabetes FIG. 11A  Control
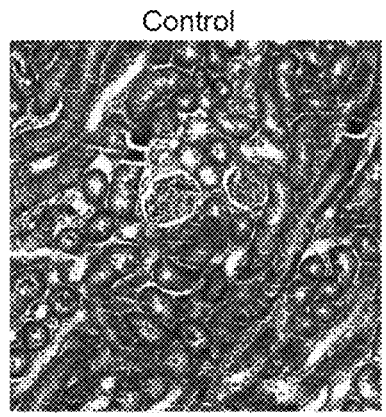
FIG. 11B  UUO
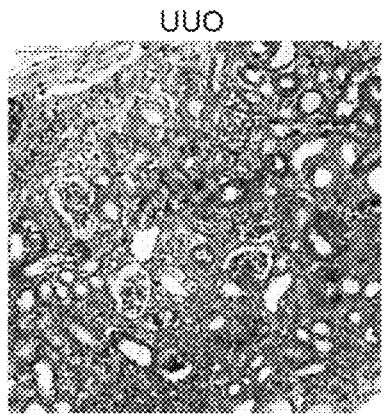
FIG. 11C  UUO + FLU
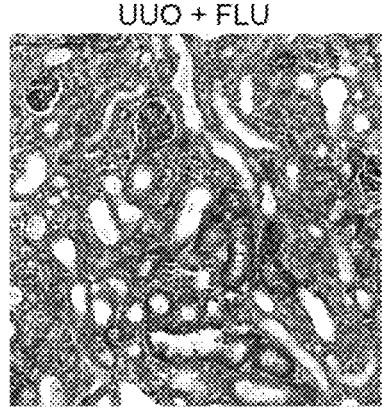
FIG. 11D  UUO + FLU + NE100
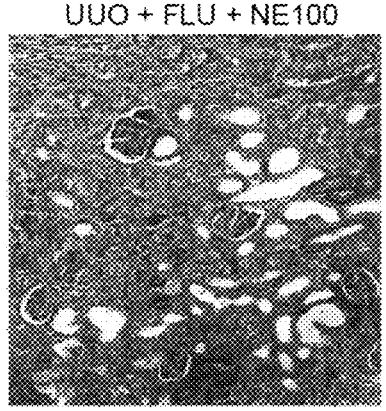
FIG. 11E  UUO induced Tubulointerstitial fibrosis
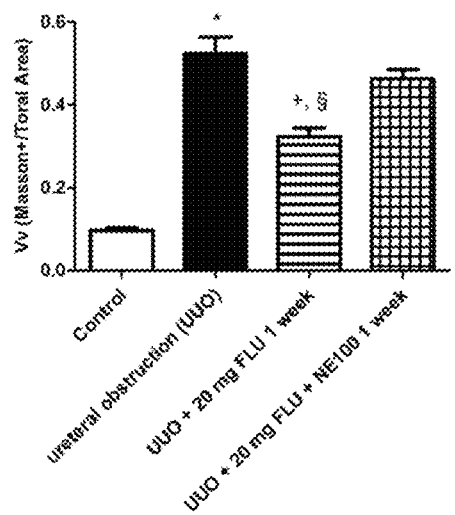
*$p<0.0001$ vs. Control; +$p<0.05$ vs. B; §$p<0.05$ vs. B + FLU + NE100

SEQUENCE LISTING

<160> NUMBER OF SEQ ID NOS: 6

<210> SEQ ID NO 1
<211> LENGTH: 24
<212> TYPE: DNA
<213> ORGANISM: Artificial Sequence
<220> FEATURE:
<223> OTHER INFORMATION: Rat collagen I forward primer

<400> SEQUENCE: 1
agctcagggg cgaaggcaac agtc                                          24

<210> SEQ ID NO 2
<211> LENGTH: 18
<212> TYPE: DNA
<213> ORGANISM: Artificial Sequence
<220> FEATURE:
<223> OTHER INFORMATION: Rat collagen I reverse primer

<400> SEQUENCE: 2
caggcgggag gtcttggt                                                 18

<210> SEQ ID NO 3
<211> LENGTH: 19
<212> TYPE: DNA
<213> ORGANISM: Artificial Sequence
<220> FEATURE:
<223> OTHER INFORMATION: Rat collagen III forward primer

<400> SEQUENCE: 3
aggcggtgcg ggtgctgat                                                19

<210> SEQ ID NO 4
<211> LENGTH: 21
<212> TYPE: DNA
<213> ORGANISM: Artificial Sequence
<220> FEATURE:
<223> OTHER INFORMATION: Rat collagen III reverse primer

<400> SEQUENCE: 4
gggccagggg gaccaatagg a                                             21

<210> SEQ ID NO 5
<211> LENGTH: 18
<212> TYPE: DNA
<213> ORGANISM: Artificial Sequence
<220> FEATURE:
<223> OTHER INFORMATION: Rat GAPDH forward primer

<400> SEQUENCE: 5
gtcacggcat ggactgtg                                                 18

<210> SEQ ID NO 6
<211> LENGTH: 20
<212> TYPE: DNA
<213> ORGANISM: Artificial Sequence
<220> FEATURE:
<223> OTHER INFORMATION: Rat GAPDH reverse primer

<400> SEQUENCE: 6
caccaccatg gagaaggctg                                               20

USE OF SIGMA-1 RECEPTOR AGONIST COMPOUNDS

This application is a CIP application of application Ser. No. 16/185,318, filed Nov. 9, 2018 (now abandoned), which is divisional of application Ser. No. 15/117,233 (now U.S. Pat. No. 10,124,006), which is the national stage of International Application PCT/HU2015/000014, filed Feb. 9, 2015, which prior applications are incorporated herein by reference.

FIELD OF THE INVENTION

The present invention is directed to compositions and methods for the prevention, and/or treatment of progressive fibrosis in various organs. In particular, embodiments of the present invention relate to the use of Sigma-1 receptor (S1R) agonists for use in the prevention and/or treatment of excessive deposition of the extracellular matrix (ECM) and/or accumulation of ECM producing cells in a medical or disease condition. In a preferred embodiment the S1R agonist is fluvoxamine.

BACKGROUND ART

The human body responds to various injuries by a biological process that involves the remodeling of the ECM, the non-cellular component present in all tissues and organs. Tissue remodeling occurs in a highly regulated and exquisitely choreographed fashion which may lead to the regeneration of the injured tissue recovering its original architecture. However, aberrant tissue remodeling characterized by excessive deposition of ECM components, among many others collagens and fibronectin, may lead to progressive fibrosis accompanied by the destruction of the original tissue architecture and the decline of organ functions. Accordingly, the term of progressive fibrosis is also used in medical sciences to describe the pathological state of excess deposition of fibrous tissue, i.e. a tissue composed of bundles of collagenous white fibers between which rows of connective tissue cells are found. The interaction of multiple pathways, molecules and systems determines whether fibrosis is homeostatic and regenerative, or whether it is uncontrolled and excessive [Pellicoro et al. *Nature Reviews Immunology* 14, 181-194 (2014)].

Progressive fibrosis is characterized by the excessive production and accumulation of extracellular matrix (ECM) components, including fibrillar collagens (collagen I and III) or collagen IV, which is one of the major components of the basement membrane and glycoproteins (e.g. fibronectin) and proteoglycans (e.g. heparin sulphate) as well. The ECM is a functional tissue whose components possess not only scaffolding characteristics, but also growth facilitating, mitogenic, and other bioactive properties.

In tissue repair, remodeling of the ECM can lead to the regeneration of the tissue when the damaged cells are replaced by other ones to recover the original function of the tissue and the ECM producing myofibroblasts undergo apoptosis. Gradually, the reconstructed ECM takes over the mechanical load again and myofibroblasts disappear. Thus, this regenerative regulatory process counteracts fibrosis which is thereby limited and called herein regenerative remodeling. In "progressive fibrosis" ECM components—particular collagen type I and III and fibronectin—and ECM producing cells continue to accumulate and this process may become adverse or even deleterious to the tissue or to the organ.

Progressive fibrosis occurs when tissue remodeling is shifted towards excessive deposition of ECM leading to destruction of the original tissue architecture and to gradual decline of tissue and/or organ function. Progressive fibrosis is a pathological process leading to the formation of permanent scar tissue; in several cases it causes organ failure and might lead to death [Lekkerkerker S et al. *Curr Pharm Des.* 18(27), 4093-102 (2012)]. Progressive fibrosis may induce a progressive and continuous loss of organ function in chronic diseases (e.g. fibroproliferative disorders).

The term myofibroblast denotes the co-existence of fibroblast morphological features, such as a developed endoplasmic reticulum (ER) and smooth muscle like features, like contractile actin filament bundles. Differentiated myofibroblasts spindle or stellate-shaped cells, which express α-smooth muscle actin (α-SMA) in their contractile filament bundles (stress fibers) and pre-eminently contribute to ECM remodeling/production. Previously, the derivation of myofibroblast from several other cell types including fibroblasts, stellate cells, pericytes, smooth muscle cells, epithelial, endothelial cells, stem cells or circulating progenitors has been suggested.

Progressive fibrosis may induce a progressive and continuous loss of organ function in chronic fibroproliferative disorders including cardiovascular diseases (cardiac fibrosis associated with acute myocardial infarction (AMI) or hypertension, fibrillation, etc); kidney related diseases, like various forms of chronic kidney diseases (CKD; e.g. diabetic nephropathy, hypertensive nephropathy, obstructive uropathies etc), gastrointestinal diseases (e.g. in inflammatory bowel disease, or esophageal atresia), pulmonary fibrotic diseases (like COPD, asthma or idiopathic pulmonary fibrosis), autoimmune diseases (including SLE, scleroderma, Boeck sarcoidosis), dermal diseases (keloid, scars, acne, or varicella etc), liver cirrhosis or urogenital diseases and many more. The prevalence of these fibroproliferative disorders is rapidly increasing and it has become a major public health problem. Indeed, according to some estimates, about 45% of all deaths are attributed to FD worldwide.

Treatment of these fibroproliferative diseases is not identical with the prevention and/or treatment of the features of progressive fibrosis themselves; fibrosis may even progress further despite or even due to the treatment of the related, possibly causative disease. Quite often pathophysiology of a disease is well or increasingly understood, while that of the accompanying progressive fibrosis is largely unexplored. As Rieder and Fiocchi note in respect of intestinal fibrosis "This ignorance is largely responsible for our current inability to diagnose intestinal fibrosis early and accurately, treat it properly, and take measures to prevent it." [Rieder et al. *Curr Opin Gastroenterol.* July; 24(4), 462-8 (2008)].

Intestinal fibrosis in inflammatory bowel disease: progress in basic and clinical science.

Treatments of Fibrotic Conditions According to the State of the Art

The few classes of compounds, which were thought to be useful in the specific treatment of pathological fibrotic conditions, include compounds having TGFβ inhibitory activity. TGFβ and related factors regulate various cellular proliferation and differentiation processes and are important to organisms for regulating repair and regeneration of cells after tissue disorder. It is known that TGFβ has a role in the accumulation of the ECM proteins and is related to fibrosis of organs or tissues. Neutralizing humanized antibodies targeting TFGB or its downstream effectors and cooperative regulator CTGF have also been tested [Hutchinson et al. *BBA* 1832, 962-971 (2013)]. However cautions must be exercised when aiming to target the TGFβ pathway. Indeed TGFβ has a well known tumor-suppressor effect, thus the inhibition of this pathway may provoke the appearance of a subset of malignant tumors. Lack of TGFβ resulted in severe multifocal inflammatory diseases and embrional lethality was observed in TGFβ knockout mice drawing attention to its the strong anti-inflammatory effect and crucial role during development. There might be also some less serious side effects of the manipulation of this pathway like photosensitivity, hepatic dysfunction, dizziness or loss of weight.

In EP 1548008 [SHIMIZU K. et al.] quinoline and quinazoline derivatives having TGFβ inhibitory activity are disclosed.

WO 03/087304A2 [LEE, Wen-Cherng et al.] teaches tri-substituted heteroaryls which are alleged to be potent antagonists of the TGFβ family type receptors, Alk5 and/or Alk4. These compounds are suggested to be useful in the prevention of fibrosis.

Pirfenidone (5-Methyl-1-phenylpyridin-2-one) reduces the production of fibrogenic mediators such as TGF and also inhibits TGFβ stimulated collagen production [Schaefer C J et al. *Eur Respir Rev* 20(120), 85-97 (2011)]. It has anti-fibrotic and anti-inflammatory properties in various in vitro systems and animal models of fibrosis. Cell-based studies have shown that pirfenidone reduces fibroblast proliferation.

Pirfenidone has been approved for treatment in idiopathic pulmonary fibrosis (IPF). In a review by Azuma A. the usefulness and limitations of pirfenidone in IPF treatment are discussed to determine its potential for the management of IPF progression [Azuma A. *Expert Review of Respiratory Medicine* 4(3), 301-310 (2010)]. It has also been proposed as anti-fibrotic and cytoprotective agent as therapy for progressive kidney disease [ME Cho et al. *Expert Opin Investig Drugs.* 19(2), 275-283 (2010)], a multicenter, randomized, double-blind placebo-controlled study of pirfenidone (1,800 mg/day) versus placebo was carried out in 107 Japanese patients Clinic with IPF. The primary end point was not significantly different between the two groups [Paz Z et al. *Rev Allerg Immunol* 38, 276-286 (2010)]. Furthermore pirfenidone cannot be administered to patients with more severe kidney disease (creatinine clearance of less than 30 ml/min) [Armendariz-Borunda J et al. *Gut* 55(11), 1663-1665 (2006)].

Tranilast (2-{[(2E)-3-(3,4-dimethoxyphenyl)prop-2-enoyl]amino}benzoic acid), an anti-allergic drug was found to be effective in the treatment of keloids and hypertrophic scars resulting from excessive collagen deposition. Recent reports suggest that tranilast reduces pathological fibrosis following AMI via inhibiting myocardial TGFβ1 expression [See *F. Heart Lung Circ.* 22(2), 122-132 (2013)]. However, while delaying the tranilast commencement of treatment to 7 days post-AMI impeded left ventricular remodeling, intervention from 24h post-AMI exacerbated infarct expansion.

Maksumova et al. in WO 2010/048716 [Maksumova L. and Unwin D. H.] teach a method in which tranilast or pirfenidone administered together with N-acetyl-cysteine results in an additive anti-proliferative effect, more pronounced than that of either drug alone.

Another treatment concept which may be useful in the treatment of keloids or hypertrophic scars is disclosed by Lee W J et al. [Lee W J et al. *Br J Dermatol.* 165(3), 673-7 (2011)]. The authors suggest that reduced expression of major ECM components (e.g. type I and III collagen, elastin and fibronectin) shows anti-fibrotic effect of relaxine-expressing adenovirus, which may have therapeutic effects on keloids by reversing pathological fibrosis and preventing keloid recurrence after surgical excision.

New therapeutic targets include e.g. 5-HT antagonists, as 5-$Ht_{2B}$ receptor activation is supposed to play a role in mitogenic signaling. This activity underpins the reason why 5-$Ht_{2B}$ receptor antagonists are treatment options of conditions associated with the development of fibrosis. WO 2009/016227 relates to 5-$HT_{2B}$ antagonist compounds useful in the treatment of fibrotic conditions.

High expression of alpha5 beta1 integrin was found in activated fibroblasts with strong accumulation of alpha5 beta1 integrin when fibroblasts switch to the fibrotic state. WO 2013/103317 teaches the use of an anti-angiogenic integrin alpha5 beta1 inhibitor compound in the treatment of fibrosis and fibrosis-related diseases, demonstrating the effectiveness of the compound in the bleomycin-induced mouse model of pulmonary fibrosis.

CA2368366 describes the beneficial effects of chymase-inhibitor compounds in the Tsk mouse model of scleroderma and the bleomycin-induced mouse model of pulmonary fibrosis.

TNFα ligands are extensively researched potential therapeutics of the disease states characterized by the overproliferation of myofibroblasts and/or excess production of fibrous material. WO 2010/085959 relates to a TNFα antagonist useful in the treatment of radiation-induced fibrosis.

Therapeutically used mesenchymal stem cells were also envisaged to regenerate organs affected by progressive fibrosis by local or systemic administration, however, clinical studies failed to unambiguously prove this concept. Furthermore they are said to be even a potential risk for turning the host environment to fibrogenic rather than regenerative cells. Paz Z and Shoenfeld Y. in 2010 gave a detailed review of treatment options for progressive fibrosis, an admittedly "heavily investigated subject" [Paz Z et al. *Clin Rev Allergy Immunol.* 38(2-3), 276-286 (2010)]. The authors are moderately optimistic but acknowledge that "No proven antifibrotic therapy has shown efficacy in ameliorating the clinical course of fibrotic diseases, but our current understanding led to the development of different drugs with promising results, like: mycophenolate mofetil, interferon, relaxin, and intravenous immunoglobulin" (emphasis added).

Similarly, Hinz. B and Gabbiani G [Hinz. B et al. F1000 *Biol Rep.,* 2:78 (2010)] after a review of the mechanisms of myofibroblast action and possible strategies for treatment evaluated recent development as "new findings that may develop into therapeutic strategies during the next few years" (emphasis added).

Most recently Karihaloo A. comes to a more gloomy conclusion on anti-fibrosis therapy [Karihaloo A. *Curr Diab Rep.* 12(4), 414-22 (2012)]: "Research points towards a multifactorial etiology and complex interplay of several pathogenic pathways that can contribute to the declining kidney function in diabetes. Patients with diabetic nephropathy (and with any chronic kidney disease) eventually develop kidney fibrosis. Despite the financial and labor investment spent on determining the basic mechanism of fibrosis, not much progress has been made in terms of therapeutic targets available to us today."

All these literature data further underline that there is no generally accepted therapy at present for progressive fibrosis in fibroproliferative disorders. Treatment of the underlying, causative or consequential disease is not sufficient to provide a solution and to treat the progressive fibrosis itself. In conclusion, the need to control progressive fibrosis per se thus remains.

The present inventors have unexpectedly found that Sigma-1-receptor (S1R) agonist compounds are useful in the prevention, control and treatment of progressive fibrosis and thereby conditions associated therewith, in particular excessive deposition of ECM, preferably collagen, e.g. collagen type I, III and fibronectin; and/or accumulation of cells producing ECM proteins.

BRIEF DESCRIPTION OF THE INVENTION

The invention relates to a SIR agonist compound for use in inhibiting, controlling, reversing or preventing progressive fibrosis in a tissue and/or in an organ of a subject, preferably a patient.

The invention relates to a SIR agonist compound for use in the treatment or prevention of fibrosis, preferably of progressive fibrosis in a tissue and/or in an organ of a subject, preferably a patient.

In a preferred embodiment the invention relates to an SiR agonist compound for use in inhibiting, controlling, reversing or preventing fibrosis preferably progressive fibrosis in a tissue and/or in an organ wherein one or more ECM components are excessively deposited, in said tissue, preferably said ECM components being selected from
Structural proteins, such as collagen and elastin
Specialized proteins, such as fibrillin, fibronectin, and laminin
Proteoglycans.

In a preferred embodiment the invention relates to a SIR agonist compound for use in inhibiting, controlling, reversing or preventing fibrosis, preferably progressive fibrosis in a tissue and/or in an organ wherein one or more ECM producing cells accumulate or excessively accumulate, preferably upon remodeling of ECM, in said tissue. Particularly, the accumulating ECM producing cells comprise or are myofibroblasts, preferably wherein myofibroblasts are excessively proliferating.

In an embodiment the patient has a diagnosed medical condition of fibrosis, preferably progressive fibrosis or is endangered by a medical condition of or accompanied by progressive fibrosis. Diagnosis of such a condition is defined optionally by the direct measurement of increased expression of collagen I-III, fibronectin and alpha smooth muscle actin ($\alpha$-SMA) in the tissue affected by progressive fibrosis. Evaluation of increased presence of Masson's trichrome or Sirius red positivity is also an option.

In a preferred embodiment the patient is diagnosed with a fibroproliferative eye disorder, preferably a disorder selected from glaucoma, preferably a glaucoma as disclosed below, in particular open angle glaucoma, an eye disease related with a fibrosis in the trabecular meshwork, an eye disease in the anterior segment of the eye, post-operative scarring, an allergic disease with fibrosis.

Preferably, the tissue of the subject or patient is the tissue of an organ selected from the group consisting of kidney, lung, liver, gastrointestinal system, secretory tissues, like pancreatic tissue, vasculature, ligaments, skin, eye, and the urogenital system, more preferably kidney, lung, liver, gastrointestinal system, urogenital system, joints and ligaments, skin and eye; even more preferably the kidney, lung, gastrointestinal system, the urogenital system, highly preferably the kidney and the lung.

Preferably, the organ of the subject or patient is selected from the group consisting of kidney, lung, liver, gastrointestinal system, secretory glands, vasculature, ligaments, skin, eye and the urogenital system, more preferably the kidney, lung, liver, gastrointestinal system, the urogenital system, ligaments, skin and eye; even more preferably the kidney, lung and gastrointestinal system, highly preferably the kidney and the lung.

In a preferred embodiment the organ differs from the brain.

In a preferred embodiment the organ differs from the heart.

In a preferred embodiment in the use according to the invention the patient has a diagnosed medical condition of progressive fibrosis or is endangered by a medical condition of progressive fibrosis accompanying a disorder, preferably a fibroproliferative disorder. Preferably said disorder, preferably fibroproliferative disorder, is selected from the group consisting of renal diseases, lung diseases, pancreatic diseases, intestinal diseases, hepatic diseases, eye diseases, diseases of the urogenital tract, dermal diseases, metabolic diseases, autoimmune diseases, diseases of the joints and ligaments (musculoskeletal system), diseases related to the use of other therapeutical drugs or processes (e.g. organ transplantation, irradiation, chemotherapy, post-operative conditions and side-effect of surgery), to burns, to various toxins, chemical or mechanical injuries etc. More preferably said fibroproliferative disorder is selected from the group consisting of renal diseases, lung diseases, pancreatic diseases, gastrointestinal diseases, hepatic diseases, eye diseases and dermal diseases. In a further embodiment the fibroproliferative disorder is selected from diseases related to the use of other therapeutical drugs or processes (e.g. organ transplantation, irradiation, chemotherapy, post-operative conditions and side-effect of surgery), to burns, to various toxins, chemical or mechanical injuries), even more preferably renal disease, lung diseases, gastrointestinal diseases; highly preferably renal diseases and lung diseases.

In an embodiment, the disorder wherein progressive fibrosis occurs is associated with anatomic abnormalities, metabolic diseases, genetic diseases, autoimmune disease, exposure to allergens (e.g. pollens) toxins (e.g. smoking, alcohol, asbestos etc.) or drugs (analgesics, acetaminophen etc) and infections, In a highly preferred embodiment the fibroproliferative disease in which progressive fibrosis is treated or is to be prevented, preferably inhibited, controlled or reversed, is a chronic renal disease characterized by a loss of renal function, e.g. decreased GFR, increased level of serum creatinine, and urea nitrogen, proteinuria and/or microalbuminuria, increased fractional excretion of sodium, accompanied by hyperkalaemia, hyponatremia, anemia, hypercholesterinaemia, hypocalcemia, hyperphosphatemia, hyperparathyreoidsm, etc.

In a preferred embodiment the disorder is different from a cancer, a tumor, preferably a malignant tumor or malignant neoplasm, In a preferred embodiment the disorder is different from a cardiovascular disorder.

In a preferred embodiment the disorder is different from a neuropsychiatric disorder.

In a preferred embodiment the compound of the invention is a S1R agonist compound wherein said compound is an agonist selective for S1R over S2R (sigma 2 receptor), i.e. the compound is a selective S1R agonist. A compound is selective for S1R over S2R if it has a higher affinity for S1R than S2R, preferably an at least 5 times higher or at least 20 times higher or at least 50 times higher or, preferably, at least $10^2$ higher or at least $10^3$ higher or at least $10^4$ higher affinity.

In a preferred embodiment the compound is a S1R agonist the effect of which can be selectively antagonized with a specific S1R antagonist, e.g. NE-100.

In a preferred embodiment said tissue is a progressively fibrotic tissue in an eye of said subject, wherein preferably cells of said tissue show actin filament rearrangement. Preferably, the subject is suffering in progressive fibrosis and has a fibroproliferative eye disorder. Particularly preferably, said fibroproliferative eye disorder is glaucoma, more preferably glaucoma is open angle glaucoma.

In a preferred embodiment said fibroproliferative eye disorder is an eye disease related with a fibrosis in the trabecular meshwork.

In a further preferred embodiment said fibroproliferative eye disorder is an eye disease in the anterior segment of the eye.

In a further preferred embodiment said fibroproliferative eye disorder is selected from the group consisting of
  glaucoma, in particular open angle glaucoma and angle closure glaucoma,
  post-operative scarring
  an allergic disease with fibrosis,
  a disease related with a fibrosis in the trabecular meshwork.

Highly preferably, the patient has open angle glaucoma and said S1R agonist is administered in the formulation of eye drops or in the form of emulsion, suspension or ointment, preferably ointment.

In a preferred embodiment wherein the tissue is an eye tissue or the fibroproliferative disorder is an eye disorder, any of the compounds as defined below is administered to the patient.

In a preferred embodiment, any of the compounds of the following general formula is administered to the patient:
  a compound of formula I',
  a compound of formula II,
  a compound of formula I'',
  a compound of formula III.

In a highly preferred embodiment, any of the compounds of general formula II is administered to the patient, in a particularly preferred embodiment fluvoxamine.

In an embodiment of the invention the S1R agonist compound is an S1R agonist compound for use as defined herein or as defined above, said S1R agonist compound having the following formula I':

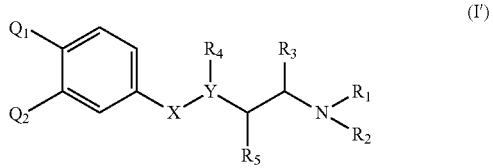 (I')

wherein
$Q_1$ is H, halogen, pseudo-halogen, C(1-4) alkyl optionally substituted with 1, 2, 3 or 4 halogen(s), C(1-3) alkoxy, C(6-10) aryl, optionally substituted with 1, 2, 3 or 4 halogen(s),
$Q_2$ is H, halogen, pseudo-halogen or C(1-3) alkoxy,
X is O, $CH_2$, ethylene or carbonyl (CO), amide or not present,
or X has the formula

wherein $R_6$ is selected from the group consisting of a hydroxyl, substituted or unsubstituted C(1-6) alkyl, preferably C(1-3) alkyl and C(1-6) alkoxy, preferably C(1-3) alkoxy, C(1-2) alkoxy C(1-6) alkyl or C(1-6) alkoxyalkil, preferably C(1-4) alkoxyalkyl, C(5-10) aryl, preferably C(5-6) aryl, or X has the formula

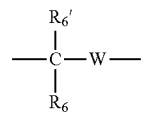

wherein W is —CH— or carbonyl (—CO—) or W is not present, and
$R_6$ and $R_6'$ are independently substituted or unsubstituted C(1-6) alkyl preferably C(1-3) alkyl, C(1-6) alkyloxy preferably C(1-3) alkoxy, C(1-6) alkoxyalkil preferably C(1-4) alkoxyalkyl, C(1-6) alkyloxy carbonyl preferably C(1-4) alkyloxycarbonyl or at least one of $R_6$ and $R_6'$, preferably $R_6'$ is a C(5-10) aryl preferably a C(5-6) aryl,
or $R_6$ and $R_6'$ together form a C(4-7) cycloalkyl, preferably a cyclopentyl or a cyclohexyl
or X has the formula

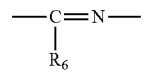

wherein is $R_6$ is selected from a substituted or unsubstituted C(1-6) alkyl preferably C(1-3) alkyl, C(1-6) alkoxy preferably C(1-3) alkoxy, C(1-6) alkoxy C(1-6) alkyl or C(1-2) alkoxy C(1-6) alkyl or C(1-6) alkoxyalkil, or C(5-10) aryl, preferably C(5-6) aryl,
Y is CH, N or O, —O—$CH_2$—$CH_2$—O— or not present wherein
if Y is O then $R_4$ is not present,
if Y is N then $R_4$ is H, or a C(1-3) alkyl or C(1-3) alkenyl, preferably ethyl or propenyl, or $R_4$ and $R_1$ together with Y, N and the carbon atoms between them form a C(5-7) heterocyclic ring,
if Y is CH then $R_4$ is selected from a H, substituted or unsubstituted C(1-4) alkyl, C(1-4) alkoxy and C(5-10) aryl, or $R_4$ and $R_1$ together with Y, N and the carbon atoms between them form a C(5-7) heterocyclic ring,
$R_3$ is selected from H, a substituted or unsubstituted C(1-6) alkyl preferably C(1-4) alkyl, C(1-6) alkoxy preferably C(1-4) alkoxy, C(1-2) alkoxy C(1-6) alkyl or C(1-6) alkoxyalkil, C(5-10) aryl, or
$R_3$ and $R_6$ together with the —X—Y—C2 alkyl moiety which they are attached to, may form a saturated or partially unsaturated 6 to 8 membered cycloalkyl or 6 to 8 membered heterocycloalkyl comprising 0 to 3 heteroatom(s), or
$R_3$ and $R_6$ together with the —X—Y—C2 alkyl moiety which they are attached to, may form a substituted or unsubstituted C(7-14) polycyclic aryl or C(7-14) polycyclic heteroaryl or C(7-14) cycloalkylaryl, or
$R_3$ and $R_4$ together with the —X—Y—C2 alkyl moiety which they are attached to, may form a saturated or partially unsaturated 6 to 8 membered cycloalkyl or 6 to 8 membered heterocycloalkyl comprising 0 to 3 heteroatom, or an alkylaryl, comprising preferably a substituted or unsubstituted phenyl, $R_5$ is C(1-3) alkyl or C(1-3) alkyloxy or $R_5$ and $R_6$ together with carbon atoms which they are attached to form a 3, 4, 5 or 6 membered saturated or unsaturated, preferably saturated ring, said ring optionally comprising a heteroatom, preferably O, wherein said ring is preferably furanyl, dihidrofuranyl or tethrahydrofuranyl, wherein preferably Y is not present, $R_1$ and $R_2$ are independently H or a C(1-6) alkyl, preferably methyl or ethyl, or $R_1$ and $R_2$ form a 5 or 6 membered, saturated or unsaturated, preferably saturated ring, said ring optionally comprising a heteroatom, preferably O, preferably an oxazine or morpholine, or alternatively N, preferably a diazine or piperazine ring or said ring being optionally a substituted or unsubstituted piperidine ring, preferably a piperidine ring substituted with one or two of OH and methoxy, and phenyl, preferably a phenyl substituted with a halogen at the para position, said substituents being preferably in the para position of the piperidine ring, or $R_1$ is a C(2-4) alkylene preferably C(2-3) alkylene or C(3-4) alkylene and together with Y and N and the carbon atoms between Y and N form a heterocyclic ring, preferably a piperazine and $R_2$ is a C(1-6) alkyl preferably C(1-4) alkyl, C(5-10) aryl preferably C(5-6) aryl or C(7-10) aralkyl, or $R_2$ is a C(2-4) alkylene preferably C(2-3) alkylene or C(3-4) alkylene and together with the N form a heterocyclic ring, preferably a tetrahydro-tetrazole, or a pharmaceutically acceptable salt thereof.

In a preferred embodiment said S1R agonist compound having the following formula I,

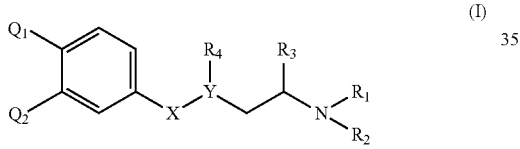

(I)

and the substitutents as defined above,
preferably
$Q_1$ is halogen, pseudo-halogen, methyl-halogen or ethyl-halogen,
$Q_2$ is H, halogen or pseudo-halogen,
X is O, $CH_2$, or X has the formula

wherein $R_6$ is selected from the group consisting of a substituted or unsubstituted C(1-6) alkyl preferably C(1-4) alkyl, C(1-6) alkyloxy preferably C(1-4) alkyloxy, C(1-6) alkoxyalkil, C(5-10) aryl preferably C(5-6) aryl,
or X has the formula

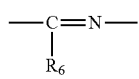

wherein $R_6$ is selected from a substituted or unsubstituted C(1-6) alkyl preferably C(1-4 alkyl), C(1-6) alkyloxy preferably C(1-4) alkyloxy, C(1-6) alkoxyalkyl, C(5-10) aryl preferably C(5-6) alkyl, Y is CH, N or O, wherein
if Y is O then $R_4$ is not present,
if Y is N then $R_4$ is H, methyl or ethyl,
if Y is CH then $R_4$ is selected from a substituted or unsubstituted C(1-4) alkyl, C(1-4) alkyloxy, C(5-10) aryl preferably C(5-6) aryl, $R_3$ is selected from H, a substituted or unsubstituted C(1-6) alkyl preferably C(1-4) alkyl, C(1-6) alkyloxy preferably C(1-4) alkyloxy, C(1-6) alkoxyalkyl, C(5-10) aryl preferably C(5-6) aryl, or $R_3$ and $R_6$ together with the —X—Y—C2 alkyl moiety which they are attached to, may form a saturated or partially unsaturated 6 to 8 membered cycloalkyl or 6 to 8 membered heterocycloalkyl comprising 0 to 3 heteroatom, or $R_3$ and $R_6$ together with the —X—Y—C2 alkyl moiety which they are attached to, may form a substituted or unsubstituted C(7-14) polycyclic aryl or polycyclic heteroaryl, or $R_3$ and $R_4$ together with the —X—Y—C2 alkyl moiety which they are attached to, may form a saturated or partially unsaturated 6 to 8 membered cycloalkyl or 6 to 8 membered heterocycloalkyl comprising 0 to 3 heteroatom, or an alkylaryl, comprising preferably a substituted or unsubstituted phenyl, $R_1$ and $R_2$ are independently H, methyl or ethyl,
or a pharmaceutically acceptable salt thereof.
Preferably said compound is fluvoxamine.
Preferably said compound is fluoxetine.

In a further preferred embodiment said S1R agonist compound has the following formula II:

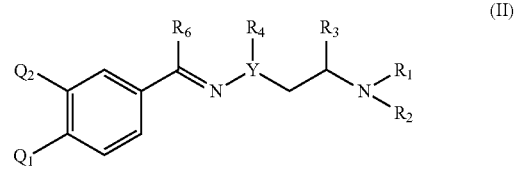

(II)

wherein
$Q_1$ is a Cl or F or a methyl-halogen selected from $CH_2F$, $CHF_2CF_3$, $CH_2Cl$, $CHCl_2$, $CCl_3$, or optionally a methoxy
$Q_2$ is H, Cl or F,
$R_6$ is selected from a substituted or unsubstituted C(1-6) alkyl preferably C(1-4) alkyl, C(1-6) alkoxy preferably C(1-4) alkoxy, C(1-6) alkoxyalkyl (or C(1-6) dialkyl-ether), C(5-10) aryl preferably C(5-6) aryl,
Y is CH or O, wherein
if Y is O then $R_4$ is not present,
if Y is CH then $R_4$ is H, methyl or ethyl,
$R_3$ is H, methyl or ethyl, or $R_3$ and $R_4$ together with the —Y—C2 alkyl moiety which they are attached to, may form a saturated or partially unsaturated cyclic group comprising 0 to 2 heteroatom(s), or $R_4$ and $R_3$ together form a C(2-4) alkyl bridge,
$R_1$ and $R_2$ are independently H, methyl or ethyl,
or a pharmaceutically acceptable salt thereof.
In a preferred embodiment in formula II
$Q_1$ is a methyl-halogen selected from $CHF_2$, $CF_3$, $CHCl_2$ and $CCl_3$,
$Q_2$ is H,
X has the formula

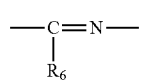

wherein R₆ is selected from a substituted or unsubstituted C(1-6) alkoxyalkyl (or C(1-6) dialkyl-ether) or C(1-2) alkoxy C(2-5) alkyl, Y is CH or O, wherein
if Y is O then R₄ is not present,
if Y is CH then R₄ is H, methyl or ethyl,
R₃ is H or methyl,
R₁ and R₂ are independently H, methyl or ethyl,
or a pharmaceutically acceptable salt thereof.

In a highly preferred embodiment the compound is fluvoxamine.

Preferably, the compound according to formula II is for use in the prevention or treatment of progressive fibrosis in a disorder, said disorder is selected from the group consisting of renal diseases, lung diseases, pancreatic diseases, intestinal diseases, hepatic diseases, eye diseases, diseases of the urogenital tract, dermal diseases, metabolic diseases, autoimmune diseases, diseases of the joints and ligaments (of the musculoskeletal system), diseases related to the use of other therapeutical drugs/processes (e.g. organ transplantation, irradiation, chemotherapy, post-operative conditions and side-effect of surgery), to burns, to various toxins, chemical or mechanical injuries.

More preferably said disorder is selected from the group consisting of renal diseases, lung diseases, pancreatic diseases, gastrointestinal diseases, hepatic diseases, eye diseases, skin diseases, and diseases of the urogenital tract.

Even more preferably said disorder is selected from the group consisting of renal diseases, lung diseases, gastrointestinal diseases, and skin diseases. In an embodiment, however, in case the compound is a compound according to formula II, the fibroproliferative disease is different from renal diseases and lung diseases now claimed in U.S. Pat. No. 10,124,006.

In a further preferred embodiment said S1R agonist compound has the following formula I″

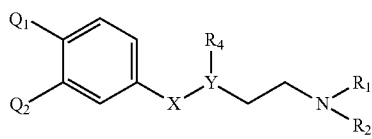

(I″)

wherein Q₁, and Q₂ are independently from each other selected from the group consisting of a halogen, preferably I, Cl and F, and a C(1-3) alkoxy, preferably a methoxy,
Y is —CH— or N,
X is ethylene or amide,
or X has the formula

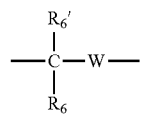

wherein W is —CH— or carbonyl (—CO—), and
R₆ and R₆' are independently substituted or unsubstituted C(1-3) alkyl, C(1-3) alkoxy, or one of R₆ and R₆' is phenyl,
R₄ is C(2-3) alkyl or R₄ is C(2-3) alkylene or C(2-4) alkenyl,
R₁ and R₂ form a 5 or 6 membered ring which is saturated or unsaturated, preferably saturated, said ring optionally comprising a heteroatom, preferably
O, preferably said ring being oxazine or morpholine, or
N, preferably said ring being diazine or piperazine ring
R₁ is a C(2-3) alkylene and together with R₁, Y and N and the carbon atoms between Y and N form a heterocyclic ring, preferably a piperazine or piperidine; and
R₂ is a C(1-6) alkyl, C(6-10) aryl or C(7-10) aralkyl,
or R₂ is a C(3-6) alkylene and together with the N form a heterocyclic ring, preferably a tetrahydro-tetrazole,
or R₂ together with R₁, R₄, Y and N and the carbon atoms between Y and N form a bicyclic heterocyclic ring, preferably octahydropyrrolo[1,2-a]pyrazine.

Preferably, the compound according to formula I″ is for use in the prevention or treatment of progressive fibrosis in a disorder, said disorder is selected from the group consisting of renal diseases, lung diseases, pancreatic diseases, intestinal diseases, hepatic diseases, eye diseases, diseases of the urogenital tract, dermal diseases, metabolic diseases, autoimmune diseases, diseases of the joints and ligaments (of the musculoskeletal system), diseases related to the use of other therapeutical drugs/processes (e.g. organ transplantation, irradiation, chemotherapy, post-operative conditions and side-effect of surgery), to burns, to various toxins, chemical or mechanical injuries.

More preferably said disorder is selected from the group consisting of renal diseases, lung diseases, pancreatic diseases, gastrointestinal diseases, hepatic diseases, eye diseases, skin diseases, and diseases of the urogenital tract.

Even more preferably said disorder is selected from the group consisting of renal diseases, lung diseases, gastrointestinal diseases, and skin diseases; highly preferably renal diseases and lung diseases. Very preferably the disease is a renal disease. Very preferably the disease is a lung disease.

In a preferred embodiment the compound according to formula I″ is a compound according to formula III':

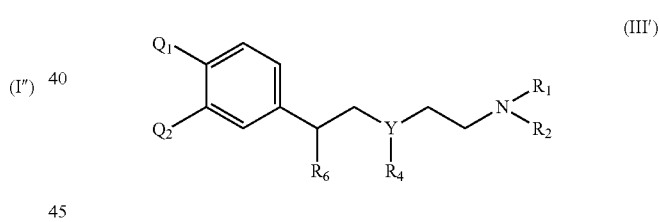

(III')

and the substituents are as defined for formula I″ mutatis mutandis
wherein
R₆ is C(1-3) alkyl, C(1-3) alkoxy, or R₆ is phenyl.

In a preferred embodiment the S1R agonist compound having the following formula (III)

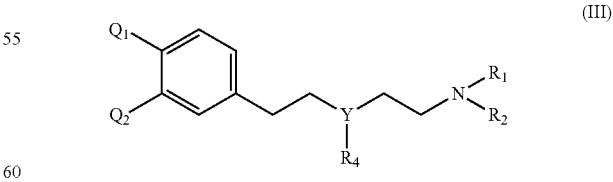

(III)

Q₁ and Q₂ are independently from each other selected from the group consisting of I, Cl and F, C(1-3) alkoxy, preferably a methoxy,
Y is N,
R₄ is C(2-3) alkyl or R₄ is C(2-3) alkylene or C(2-4) alkenyl R₁ and R₂ form a 5 or 6 membered ring which is saturated or unsaturated, preferably saturated, said ring optionally comprising a heteroatom, preferably O, preferably said ring being oxazine or morpholine, or N, preferably said ring being diazine or piperazine ring or R₁ is a C(2-3) alkylene and together with R₄, Y and N and the carbon atoms between Y and N form a heterocyclic ring, preferably a piperazine or piperidine; and R₂ is a C(1-6) alkyl, C(6-10) aryl or C(7-10) aralkyl, or R₂ is a C(3-6) alkylene and together with the N form a heterocyclic ring, preferably a tetrahydro-tetrazole, or R₂ together with R₁, R₄, Y and N and the carbon atoms between Y and N form a bicyclic heterocyclic ring, preferably octahydropyrrolo[1,2-a]pyrazine.

Preferably in formula III

Q₁ and Q₂ are independently from each other selected from the group consisting of Cl, F and a methoxy, Y is N, R₄ is C(2-3) alkyl or R₄ is C(2-3) alkylene or C(2-4) alkenyl R₁ and R₂ form a 5 membered ring said ring comprising a N, or R₁ is a C(2-3) alkylene and together with R₄, Y and N and the carbon atoms between Y and N form a heterocyclic ring, preferably a piperazine or piperidine; and R₂ is a C(1-6) alkyl, C(6-10) aryl or C(7-10) aralkyl.

In a preferred embodiment the compound is SA 4503 (cutamesine).

Preferably, the compound according to formula III for use in the prevention or treatment of progressive fibrosis in a disorder, said disorder is selected from the group consisting of renal diseases, lung diseases, pancreatic diseases, intestinal diseases, hepatic diseases, eye diseases, diseases of the urogenital tract, dermal diseases, metabolic diseases, autoimmune diseases, diseases of the joints and ligaments (of the musculoskeletal system), diseases related to the use of other therapeutical drugs/processes (e.g. organ transplantation, irradiation, chemotherapy, post-operative conditions and side-effect of surgery), to burns, to various toxins, chemical or mechanical injuries.

More preferably said disorder is selected from the group consisting of renal diseases, lung diseases, pancreatic diseases, gastrointestinal diseases, hepatic diseases, eye diseases, skin diseases, and diseases of the urogenital tract.

Even more preferably said disorder is selected from the group consisting of renal diseases, lung diseases, gastrointestinal diseases, and skin diseases; highly preferably renal diseases and lung diseases. Very preferably the disease is a renal disease. Very preferably the disease is a lung disease.

In a preferred embodiment said S1R agonist compound has the following formula IV

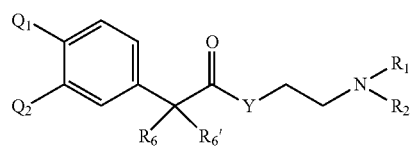

(IV)

wherein Q₁ and Q₂ are, independently from each other, H or C(1-2) alkyl,

R₆ and R₆' together form a C(4-7) cycloalkyl, preferably a cyclopentyl or a cyclohexyl Y is O or O—CH₂—CH₂—O or NH, and R₁ and R₂ are independently H or, methyl or ethyl, or R₁ and R₂ form a 5 or 6 membered ring which is saturated or unsaturated, preferably saturated, said ring optionally comprising a heteroatom, preferably O, preferably said ring being oxazine or morpholine, or N, preferably said ring being diazine or piperazine ring.

In a preferred embodiment the compound is selected from PRE-084 and pentoxyverine (carbetapentane).

Preferably, the compound according to formula IV for use in the prevention or treatment of progressive fibrosis in a disorder, said disorder is selected from the group consisting of renal diseases, lung diseases, pancreatic diseases, intestinal diseases, hepatic diseases, eye diseases, diseases of the urogenital tract, dermal diseases, metabolic diseases, autoimmune diseases, diseases of the joints and ligaments (of the musculoskeletal system), diseases related to the use of other therapeutical drugs/processes (e.g. organ transplantation, irradiation, chemotherapy, post-operative conditions and side-effect of surgery), to burns, to various toxins, chemical or mechanical injuries.

More preferably said disorder is selected from the group consisting of renal diseases, lung diseases, pancreatic diseases, gastrointestinal diseases, hepatic diseases, eye diseases, skin diseases, and diseases of the urogenital tract.

Even more preferably said disorder is selected from the group consisting of renal diseases, lung diseases, gastrointestinal diseases, and skin diseases; highly preferably renal diseases and lung diseases. Very preferably the disease is a renal disease. Very preferably the disease is a lung disease.

In a preferred embodiment the invention relates to said S1R agonist compound having the following formula V

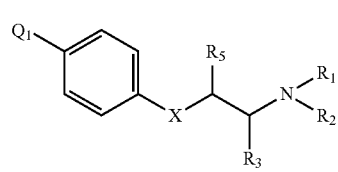

(V)

wherein Q₁ is a halogen, phenyl or H,

R₃ is H or Me,

R₅ is H, C(1-3) methyl or C(1-3) alkoxy,

X has the formula

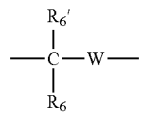

wherein W is methylene or not present, and

R₆ is H or methyl

R₆' is C(1-6) alkyl, C(1-6) alkyloxy or a C(6-10) aryl, preferably a phenyl, or R₅ and R₆ together with the carbon atoms to which they are attached to form a 3, 4, 5 or 6 membered ring (saturated or unsaturated, preferably saturated), said ring optionally comprising a heteroatom, preferably O, wherein said ring is preferably a furanyl, dihidrofuranyl or tetrahydrofuranyl, more preferably tetrahydrofuranyl, wherein preferably the compound is Anavex 2-73, or X has the formula

wherein R$_6$ is selected from a substituted or unsubstituted C(1-2) alkyl and C(1-2) alkyloxy and a C(6-10) aryl, preferably C(1-2) alkyl, preferably methyl, wherein preferably the compound is RC-33.

In a further preferred embodiment said S1R agonist compound has the following formula (VI)

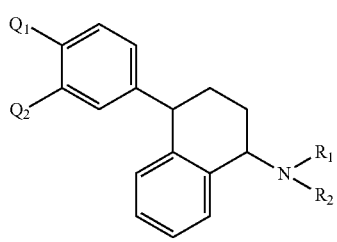

(VI)

wherein Q$_1$ and Q$_2$, independently from each other, are selected from the group consisting of a halogen, preferably Cl and F, and a C(1-3) alkoxy, preferably a methoxy, R$_1$ and R$_2$ are independently H, methyl or ethyl, Preferably, in formula II Q$_1$ and Q$_2$ are identical and are selected from the group consisting of Cl and F and a methoxy, R$_1$ and R$_2$ are independently H, methyl or ethyl.

In a preferred embodiment said compound is sertraline.

Preferably, the compound according to formula V or formula VI for use in the prevention or treatment of progressive fibrosis in a disorder, said disorder is selected from the group consisting of renal diseases, lung diseases, pancreatic diseases, intestinal diseases, hepatic diseases, eye diseases, diseases of the urogenital tract, dermal diseases, metabolic diseases, autoimmune diseases, diseases of the joints and ligaments (of the musculoskeletal system), diseases related to the use of other therapeutical drugs/processes (e.g. organ transplantation, irradiation), to burns, to various toxins, chemical or mechanical injuries.

More preferably said disorder is selected from the group consisting of renal diseases, lung diseases, pancreatic diseases, gastrointestinal diseases, hepatic diseases, eye diseases, diseases of the urogenital tract.

Even more preferably said disorder is selected from the group consisting of renal diseases, lung diseases, gastrointestinal diseases and urogenital diseases; highly preferably renal diseases and lung diseases. Very preferably the disease is a renal disease. Very preferably the disease is a lung disease.

In a preferred embodiment said S1R agonist compound is selected from the group consisting of 2-{[(E)-{5-methoxy-1-[4-(trifluoromethyl)phenyl]pentylidene}amino]oxy}ethanamine (fluvoxamine);

N-methyl-3-phenyl-3-[4-(trifluoromethyl)phenoxy]propan-1-amine (fluoxetine);

(1S,4S)-4-(3,4-dichlorophenyl)-N-methyl-1,2,3,4-tetrahydronaphthalen-1-amine (sertraline);

1-[2-(3,4-dimethoxyphenyl)ethyl]-4-(3-phenylpropyl)piperazine (cutamesine);

(8aR)-2-[2-(3,4-dichlorophenyl)ethyl]octahydropyrrolo[1,2-a]pyrazine (BD1031);

N-[2-(3,4-dichlorophenyl)ethyl]-N-(2-pyrrolidin-1-ylethyl) prop-2-en-1-amine (BD1052);

N—(N-benzylpiperidin-4-yl)-4-iodobenzamide (4-IBP);

2-morpholin-4-ylethyl-1-phenylcyclohexane-1-carboxylate (PRE-084);

2-[2-(diethylamino)ethoxy]ethyl 1-phenylcyclopentanecarboxylate (carbetapentane);

(S*,R*)-2-[(4-hydroxy-4-phenyl-1-piperidinyl)methyl]-1-(4-methylphenyl)-cyclopropanecarboxylic acid methyl ester (ppcc);

4-[4-(4-chlorophenyl)-4-hydroxy-1-piperidyl]-1-(4-fluorophenyl)-butan-1-ol (haloperidol);

tetrahydro-N,N-dimethyl-2,2-diphenyl-3-furanmethanamine hydrochloride (anavex2-73) or 1-[1-(4-biphenyl)-1-methyl-propyl]piperidine (RC-33)

or a pharmaceutically acceptable salt thereof.

In a preferred embodiment the invention relates to a S1R agonist compound for use in preventing, controlling, inhibiting or reversing progressive fibrosis in a tissue of a subject wherein said tissue is a progressively fibrotic tissue in the kidney of said subject and said subject suffers in or is endangered by a renal disease. Preferably, the S1R agonist is a compound selected from the list given above, highly preferably the compound is fluvoxamine.

In a preferred embodiment the compound of the invention is a synthetic compound.

In a preferred embodiment the compound of the invention cannot be synthesized by a biological organism.

In a preferred embodiment the compound of the invention is different from a natural compound and/or a natural product.

In a preferred embodiment the compound of the invention is different from a compound that contains three or more interconnected rings of atoms. Thus, it is different from a tricyclic and a quatrocyclic compound.

In a preferred embodiment the compound of the invention is different from a steroid, i.e. a compound having an androstane skeleton, preferably from a sterane.

In a preferred embodiment the compound of the invention comprises monocyclic and/or bicyclic ring(s) only. Preferably the compound of invention comprises monocyclic ring(s) only.

"Compound of the invention" is to be understood as "compound of the invention for use according to the invention" or compound for use according to the invention.

In an embodiment the compound is an optically active compound, which is present in the form of a racemate or in an optically pure form.

According to a further aspect the invention relates to a method of preventing or treating fibrosis, preferably progressive fibrosis said method comprising administering to a subject or patient an S1R agonist compound as defined above in an effective amount. Preferably in an amount sufficient for preventing, controlling, reversing or inhibiting progressive fibrosis. Preferably the subject or patient suffers in a condition of progressive fibrosis. Preferably said subject or patient suffers in a disorder, preferably a fibroproliferative disorder associated with or characterized by progressive fibrosis.

Preferably the subject or patient is a mammalian or avian subject or patient.

Preferably the compound is a compound as defined above or in the appended claims.

Preferably the compound is an S1R selective S1R agonist as defined above or in the appended claims.

Preferably the compound for use in said treatment is a compound according to formula I or formula I' as defined above.

Preferably the compound for use in said treatment is a compound according to formula II or formula II' as defined above.

Preferably the compound for use in said treatment is a compound according to formula I" or formula III or formula III' as defined above.

Preferably the compound for use in said treatment is a compound according to formula IV as defined above.

Preferably the compound for use in said treatment is a compound according to formula V or formula VI as defined above.

Highly preferably the compound is fluvoxamine or a compound of related structure.

Highly preferably the compound is cumetasine or a compound of related structure.

The invention further relates to a method comprising the step of administering a S1R agonist as disclosed herein to subject or patient wherein a tissue of said subject or patient is affected by progressive fibrosis and thereby inhibiting, controlling or reversing progressive fibrosis in said tissue, preferably fibrotic remodeling of ECM in said tissue, said method comprising administering to said tissue a S1R agonist compound (S1R agonist). Preferably said tissue affected by progressive fibrosis is targeted and/or contacted by the S1R agonist.

The method according to the invention wherein the S1R agonist is contacted with a tissue of a subject or patient whereby fibrotic remodeling of ECM is prevented or ameliorated in said tissue of the patient.

The method according to the invention wherein said S1R agonist is administered to said patient in a dose sufficient for agonizing S1R in the tissue of the patient.

The method according to the invention wherein said S1R agonist is administered in a dose sufficient for preventing, controlling, inhibiting or reversing accumulation of ECM producing cells, which comprise or are myofibroblasts in the tissue. Preferably, the myofibroblasts are originated or differentiated from the existing fibroblasts; however other sources such stellate cells, pericytes, smooth muscle cells, epithelial, endothelial cells, stem cells or circulating progenitors has been suggested although the relative contribution of each varies between tissues. The method according to the invention wherein said S1R agonist is administered in a dose sufficient for preventing, controlling, inhibiting or reversing excessive deposition of ECM or ECM components in said tissue.

Preferably, the ECM components accumulated or excessively deposited in remodeling of ECM comprise an ECM component as defined herein (e.g. in the DEFINITIONS chapter), or preferably a protein selected preferably from collagen I, III, and fibronectin, or other ECM forming proteins or proteoglycans.

Preferably, said method comprising administering to an S1R expressing tissue as defined herein; a S1R agonist compound as defined herein; whereby an effective level of the S1R agonist is provided in said tissue and wherein the S1R agonist is contacted with a tissue of a patient whereby progressive fibrosis is prevented or ameliorated in said tissue of the patient.

In a highly preferred embodiment the S1R agonist compound is administered to the subject or preferably to a patient before the onset or during of progressive fibrosis in the tissue of said subject or preferably a patient.

The disorder or condition accompanied by fibrosis, preferably progressive fibrosis and wherein progressive fibrosis is treated in any disorder or condition as defined herein. In a highly preferred embodiment the medical condition is chronic kidney disease.

The invention also relates to a cosmetic method for the treatment of a subject having fibrosis, preferably progressive fibrosis effecting the skin said method comprising the step of administering a compound as defined above in an effective dose, to the area of the skin affected by progressive fibrosis; preferably in the form that is suitable for topical, percutaneous, or transdermal application (e.g. cream, lotion, ointment, etc)

In an embodiment the compound for use according to the invention is in the form of or is present in a pharmaceutical composition.

Thus, the invention relates to a pharmaceutical composition or a cosmetic composition comprising the compound of the invention for use according to the invention said composition also comprising a pharmaceutically acceptable carrier or excipient.

Preferably the pharmaceutical composition is for or is suitable for oral, parenteral (including intravenous, intramuscular, intrasynovial, intrathecal, intranasal, intratracheal, intraosseal, intracardiac, intragastrical, intrabuccal, intravaginal, intrarectal, percutaneous, subcutaneous, sublingual), topical or transdermal, administration into said tissue of the patient.

Said pharmaceutical compositions may be formulated as pills, tablets, tabs, coated tablets, film tablets, capsules, powders, granulates, sustained-release formulations, suspensions, injections, drops, sprays, aerosols, suppositories, ointments, creams, pastes, syrup, lotion or gels.

Most preferably the pharmaceutical composition is present in the form of tablets either for oral, percutaneous (cream, gels) or topical (drops, aerosol) administration.

For the purpose of ocular administration it should be taken into account that the eye has an anterior segment and posterior segment. "Tissues such as cornea, conjunctiva, aqueous humor, iris, ciliary body and lens make up the anterior portion. Back of the eye or posterior segment of the eye include sclera, choroid, retinal pigment epithelium, neural retina, optic nerve and vitreous humor. The anterior and posterior segment of eye is affected by various vision threatening diseases. Diseases affecting anterior segment include, but not limited to glaucoma, allergic conjunctivitis, anterior uveitis and cataract. While age-related macular degeneration (AMD) and diabetic retinopathy are the most prevalent diseases affecting posterior segment of the eye." [Patel Ashaben. Ocular drug delivery systems: An overview. World J Pharmacol. 2013; 2(2): 47-64.] There is a variety of barriers which protect the eye in particular the posterior segment and it is often a challenge of intraocular drug delivery to surpass these barriers and maintain drug levels in tissues.

In case of ocular formulation for use in the anterior segment, however, topical administration, like topical instillation is usually appropriate, even if ocular bioavailability is low with topical drop administration. Traditionally, a variety of drug delivery routes can be applied, like eye drops or topical liquids, emulsions, suspensions and ointments. Emulsions and suspensions may provide formulations which may result in a better resorption due to a capability to better surpass barriers. More advanced formulation means include nanotechnology based and sustained release formulations. A review of the formulation techniques is provided by Patel Ashaben et al. [Patel Ashaben. Ocular drug delivery systems: An overview. World J Pharmacol. 2013; 2(2): 47-64.] the content of which is incorporated herein as a teaching for eye specific formulations by reference.

In case of the posterior segment of the eye, topical administration like eye drops and topical liquids, may require the use use of nanoparticles in which the drug is incorporated to achieve therapeutic levels at the posterior pole. Systemic administration is usually not advantageous because of the relatively small mass and volume of the eye. In a particular embodiment drug delivery to the posterior segment can be effected by e.g. intraocular injections, like intravitreal injections or periocular injections, whereas intravitreal injections are preferred.

In the method according to the invention wherein the S1R agonist compound is used, the tissue is a progressively fibrotic tissue or a tissue having propensity for progressive fibrosis in an organ of said subject/patient, said organ being selected from kidney, lung, liver, gastrointestinal system, secretory tissues, like pancreatic tissue, vasculature, ligaments, skin, eye, and the urogenital system. In the present invention eye is preferred.

Below conditions regularly accompanied by progressive fibrosis are listed in more detail.

In a preferred embodiment the subject or patient suffering in or endangered by progressive fibrosis has a diagnosed medical condition of a fibroproliferative disease selected from the group consisting of renal diseases, lung diseases, pancreatic diseases, intestinal diseases, hepatic diseases, eye diseases, metabolic diseases, autoimmune diseases, skin diseases, diseases of the urogenital tract, fibroproliferative diseases associated with pathological pregnancy, diseases of the urogenital tract in men and obstructive uropathies.

Preferably the fibroproliferative disease is selected from the group consisting of pancreatic diseases, intestinal diseases, hepatic diseases, eye diseases, metabolic diseases, autoimmune diseases, skin diseases, diseases of the urogenital tract Particularly preferably the fibroproliferative disease is an eye disease. Preferably said eye disease is selected from the group consisting of
  glaucoma,
  post-operative scarring
  an allergic disease with fibrosis in the eye,
  a disease related with a fibrosis in the trabecular meshwork.

In a preferred embodiment glaucoma is selected from open angle glaucoma and angle closure glaucoma.

In a preferred embodiment glaucoma is selected from primary glaucoma and secondary glaucoma.

Both primary glaucoma and secondary glaucoma can be selected from open angle glaucoma and angle closure glaucoma.

Below examples of diseases of various organs are given.

Examples of Renal Diseases:
  diabetic nephropathy, hypertensive nephropathy, glomerular diseases including proliferative glomerulonephritis (mesangial proliferative, membranoproliferative, focal proliferative, diffuse proliferative, crescenic); glomerulonepritis associated with lupus nephritis, bacterial endocarditis, vasculitis, chronic hepatitis, infections (e.g. hantavirus), non-inflammatory glomerular diseases (minimal change nephritis, focal glomerular sclerosis, membranousus nephropathy, fibrillary glomerular disease), glomerular disease associated with Hodgkin's disease, antibiotic, drug (aspirin, ibuprofen, acetaminophen, tacrolimus, cyclosporine, contrast agents, chemotherapy, or heroin toxicity) HIV infection. Hereditary nephritis (Alport syndrome), vascular diseases including renal artery stenosis, sickle cell disease, hemolytic uremic syndrome, atypic hemolytic uremic syndrome. Tubulointerstitial diseases including pyelonephritis, analgesic nephritis, allergic interstitial nephritis, granulomatous interstitial nephritis, autoimmune interstitial nephritis, non-inflammatory t diseases like reflux nephropathy, obstructive uropathies (anatomical abnormalities e.g posterior urethra valve, or stones, or malignancy or prostatism) myeloma kidney; Diseases in the transplant like chronic rejection, drug toxicity, recurrent disease, transplant glomerulopathy;

Examples of Lung Diseases:
  bronchitis, asthma, idiopathic pulmonary fibrosis, usual interstitial pneumonia, gas or ionizing radiation induced lung fibrosis, nitrofurantoin, tobacco smoke-induced lung fibrosis, emphysema, chronic obstructive pulmonary disease, tuberculosis, rheumatoid arthritis induced lung fibrosis, systemic lupus erythematosus induced lung fibrosis, sarcoidosis, Wegener's granulomatosis, nonspecific interstitial pneumonitis, Hamman-Rich Syndrome, diffuse fibrosing alveolitis, inhalation of environmental and occupational pollutants (fume silica, asbestos, nitrogen, and sulfur gases, fumes, vapors of detergenst, cleaners, hydrochloric acid, herbicide, hairspray); Drugs-induced pulmonary fibrosis (bleomycin, amiodarone, busulfan, methotrexate, apomorhpine, nitrofuratoin, phenytoin) and radiotherapy. Torque teno virus; pneumoconiosis Examples of Pancreatic Diseases:
  alcoholic chronic pancreatitis, hereditary pancreatitis, autoimmune pancreatitis, obstructive chronic pancreatitis, tropical calcific pancreatitis, fibrocalculous pancreatic diabetes, chronic non-alcoholic pancreatitis, chronic atrophic pancreatitis, Groove pancreatitis, Examples of Intestinal Diseases:
  ulcerative colitis, Crohn's disease, Collagenous colitis, microscopic colitis, diversion colitis, necrotizing enterocolitis, chemical colitis, ischemic enterocolitis, *Helicobacter pylori*-induced gastritis, chronic gastritis, Oesophageal sub-epithelial fibrosis, Barrett's esophagus, gastroesophageal reflux disease, oral submucous fibrosis, oesophageal atresia, Examples of Hepatic Diseases that are:
  nonalcoholic steatohepatitis, autoimmune hepatitis, viral hepatitis (hepatitis A, hepatitis B, hepatitis C, hepatitis D), alcoholic hepatitis, toxic and drug-induced hepatitis, non-alcoholic fatty liver disease, liver cirrhosis, fascioliasis, schistosomiasis, liver fluke induced fibrosis, primary sclerosing cholangitis, Budd-Chiari syndrome, biliary atresia, Alagille syndrome, progressive familial intrahepatic cholestasis, serotonergic agonist drugs: weight loss drugs (fenfluramine, chlorphentermine, aminorex), anti-migraine drugs (ergotamine, methysergide), antiparkinsonian drugs (pergolide, cabergoline), recreational drugs (MDA, MDMA, DOI, mCPP), Examples of Eye Diseases:
  Preferred examples of eye diseases are diseases of the anterior part of the eye.

A frequent and particularly preferred fibroproliferative disease to be treated according to the invention of the eye is glaucoma. Glaucoma may be e.g. an open angle glaucoma or a closed angle glaucoma or angle-closure glaucoma.

Recently it has become known that in a part of the glaucomas, preferably in open-angle glaucoma, fibrosis is related to an accumulation of extracellular matrix (ECM) materials in the trabecular meshwork (TM) at the anterior of the eye resulting in clogging of the TM forming an obstacle to exit of the aqueous humor (AH) via its normal pathway and the pressure within the eye subsequently increases [McDonnell, Fiona et al. The Role of Epigenetics in the Fibrotic Processes Associated with Glaucoma. Journal of Ophthalmology Volume 2014, Article ID 750459, 13 pages]

Preferably the glaucoma according to the invention is a glaucoma related to progressive fibrosis in the trabecular meshwork.

Angle-closure glaucoma, a less common form of glaucoma and is caused by blocked drainage canals, resulting in a sudden rise in intraocular pressure in which fibrosis may also be formed.

Variants of open-angle and angle-closure glaucoma include and be selected from the group consisting of secondary glaucoma, pigmentary glaucoma, pseudoexfoliative glaucoma, irido corneal endothelial syndrome (ice), exfoliative glaucoma, neovascular glaucoma, traumatic glaucoma, uveitic glaucoma, traumatic glaucoma, congenital glaucoma.

Secondary glaucoma refers to any glaucoma in which there is an identifiable cause of increased eye pressure and/or in which another disease causes or contributes to increased eye pressure, resulting in optic nerve damage and vision loss.

According to present protocols glaucoma is treated by reduction of eye pressure.

In the present invention glaucoma is treated by the administration of a Sigma-1 receptor agonist, preferably an S1R agonist as described above. Preferably, said S1R agonist is formulated in the form of eye drops or topical liquids, emulsions, suspensions, ointments and implants with sustained drug releasing.

In a preferred embodiment the fibroproliferative eye disease is a disease related to or the pathogenesis of which involves progressive fibrosis in the tabecular meshwork of the eye.

In an other preferred embodiment scarring after or in parallel with eye operations are treated. As noted above upon wound healing an excess accumulation of extracellular matrix may occur related with progressive fibrosis.

A further field of treatment may be allergic disease in which the eye is involved.

In an embodiment the glaucoma is different from neovascular glaucoma, which is typically of posterior segment origin, and wherein the underlying pathogenesis in most cases is posterior segment ischemia.

Further examples of eye diseases: diabetic retinopathy, fibrosis of the cornea, neovascular glaucoma, retinopathy of prematurity, age-related macular degeneration, premacular fibrosis, herpetic keratitis, pingueculae, capsular fibrosis, fibrosis of the posterior lens capsule, fibrovascular scarring of the retina, gliosis in the retina, complication of surgery to treat retinal detachment, viral infection of the cornea, retinal injury due to hypoxia or inflammatory changes, trachoma, congenital fibrosis syndrome, levator muscle fibrosis, congenital fibrosis of the ocular muscles, congenital fibrosis of the extraocular muscles, proliferative retinopathy, macular fibrosis, talc retinopathy, subretinal fibrosis, subconjunctival fibrosis, chronic dry eye, proliferative vitreoretinopathy, infectious and non-infectious keratitis, postoperative fibrosis of the ocular tissues (ocular adnexa, retina, lens capsule, trabecular meshwork, cornea, sclera, conjunctiva), corneal degenerations and dystrophies, retinal dystrophies.

In a preferred embodiment wherein the tissue is an eye tissue or the fibroproliferative disorder is an eye disorder, any of the compounds as defined below is administered to the patient.

In a preferred embodiment, any of the compounds of the following general formula is administered to the patient:

a compound of formula I',
a compound of formula II,
a compound of formula I'',
a compound of formula III.

In a highly preferred embodiment, any of the compounds of general formula II is administered to the patient, in a particularly preferred embodiment fluvoxamine.

Examples of metabolic diseases: Type 2 diabetic complications atherosclerosis, arteriosclerosis, diabetic foot; metabolic syndrome; hyperlipidaemia; haemochromatosis; Wilson-disease; alfa-1-antitrypsin deficiency; galactosaemia; glycogen storage disease I-IV; VI; IX; XI; urate nephropathy; hyperlipoproteinaemia I.-V.; familiar hypercholesterineaemia; mucopolysaccharidosis type I-VII.; mucolipidosis III-IV; Fabry disease (angiokeratoma corporis diffusum); pseudoxanthoma elasticum, Examples of autoimmune diseases: Type 1 diabetic complications; rheumatoid arthritis; ankylosing spondylitis (Bechterew's disease); systemic lupus erythematosus; systemic sclerosis; Sjögren's syndrome; CREST-syndrome, polymyositis; dermatomyositis; primary biliary cirrhosis; primary sclerotising cholangitis; vasculitis: giant cell arteritis, Takayasu's arteritis, polyarteritis nodosa, Wegener's granulomatosis; thromboangitis obliternas; sarcoidosis; Goodpasture syndrome; mixed connective tissue disease; Churg-Strauss-syndrome, Examples of skin diseases: keloid and scars associated with trauma, operations, piercing, acne, chicken pox, infections, (cutting), haematoma, spontaneusly, granuloma, tick-granuloma; solaris atrophia, burn injury, pseudocicatrix *stellata* (Batman purpura), ulcus associated with anthrax, gonorrhoea, ulcus molle, tularaemia, decubitus, diabetic foot sy, diabetes skin, necrobiosis lipoidica diabeticorum, varicosits cruris, thrombophlebitis, infections: fascitis necrotisans, ecthyma simplex, ecthyma gangrenosum, phlegmone-abscessus, furunculus, carbunculus, anthrax, granuloma venereum, tularaemia, tbc (lupus vulgaris, scrofuloderma), lepra, Lyme-borreliosis, Tibola (Tick-Bone-Lymphadenopathy), syphilis, actinomycosis, every mycotic infection secundary infection scar tissue, HSV, VZV, erythema multiforme, dermatitis herpetiformis; scars associated with prurigo (infection, allergy, irritation, paraneopl.gravidarum, diabetes) acne: ecthyma simplex, acne inversa, acne vulg, rosacea, rinophima, dermatitis seborhoica, Cushing-syndrome), Operations, side effects of surgery (sec. infection, sponge, splintering), Examples of diseases of the urogenital tract: menstrual disorders: endometriosis, PCOS, adrenal diseases (CAH, Cushing, virilizing sy, acne, seborrhea), Asherman's syndrome (-iatrogen), endometritis, IUD), infections: perinephritis, paranephritis, pyelonephritis, pyelitis and pyelonephritis.chronica, pyelonephros, chonic. uretritis (gonorrhoea, *E. coli, Proteus*, HSV), retroperitoneal fibroma, cystitis chronica, cystitis after radiotherapy, ulcus simplex (Hunner), Trichomonases, tuberculosis (renis, vesicae urinariae, epididymitis, prostata), actinomycosisulcus, pelveopeitonitis, vulvovaginitis cand, herpes genitalis, genitalis HPV, chronic cervicitis, endometritis, salpingitis, *abscessus*. tuboovarii; Douglas, syphilis, gonorrhoea, chlamidya, *trichomonas*, HPV, ulcus molle, HIV, tuberculosis, Examples of fibroproliferative diseases associated with pathological pregnancy: pruritus gravidarum, bullosus pemphigoid, impetigo herpetiformis, caesairan section (or other operation) rupture corporis uteri, ulcer puerperalis, endometritis, myometritis puerperalis, adnexitis puerperalis, pelveoperitonitis puerperalis, parametritis puerperalis, thrombophlebitis, mastitis puerperalis. In men: penis, prostata, orchis: cavernitis, induratio penis plastica, prostatitis, *abscessus*, orchitis chronic. epididymitis. Obstructive uropathies associated with anatomical abnormalities posterior urethra valve, subvesical obstruction, vesicouretheral reflux nephrolithiasis, inflammation. arthritis urica, hyperparathyreosis, hypercalcaemia, oxalosis, cystinuria, xantinuria.

Definitions

A "subject" as used herein is an individual of an animal species, preferably a vertebrate, more preferably a mammalian or avian species, in particular a mammalian species, highly preferably the individual is a primate, a hominid or a human.

A "patient" is a subject who is or intended to be under medical or veterinarian observation, supervision, diagnosis or treatment.

A "treatment" refers to any process, action, application, therapy, or the like, wherein the subject or patient is under aid, in particular medical or veterinarian aid with the object of improving the subjects's or patient's condition, either directly or indirectly. Improving the subjects's condition may include improving an aesthetic condition (cosmetic treatment) and/or may include, in particular, restoring or maintaining normal function of an organ or tissue, preferably at least partly restoring or maintaining health (medical or veterinarian treatment). Treatment typically refers to the administration of an effective amount of a compound or composition described herein. Treatment may relate to or include medical or veterinarian treatment and cosmetic treatment, in particular medical or veterinarian treatment.

A "composition" or "formulation" of the invention is a composition of matter which comprises at least one biologically active substance suitable for the treatment of progressive fibrosis as defined herein in an effective amount. Compositions may also comprise further biologically active substances useful e.g. in a combination therapy. Furthermore, the compositions may comprise biologically acceptable carriers, formulation agents, excipients etc. which are well known in the art.

The terms "effective amount" or "therapeutically effective amount" are intended to qualify the amount of a therapeutic agent required to relieve to some extent one or more of the symptoms of a condition, disease or disorder, including but not limited to: 1) reducing the number of myofibroblasts; 2) reducing the synthesis of the ECM components, and/or increasing the degradation of the ECM component; 3) reducing the size of the fibrous tissue; 4) improving to at least some extent the physiological function of the tissue due to any of 1) to 3);

As used herein, the term "alkyl" alone or in combinations means a straight or branched-chain hydrocarbon group containing preferably from 1 to 6, preferably 1 to 4 or 1 to 3 carbon atom(s) or 1 to 2 carbon atom(s) [i.e. "C(1-6)" "C(1-4)" or "C(1-3)" or "C(1-2)" alkyl groups, respectively], such as methyl, ethyl, propyl, isopropyl, butyl, sec-butyl and t-butyl.

As used herein, the term "alkoxy" means an alkyl-O— group in which the alkyl group is as previously described. Non-limiting examples of suitable alkoxy groups include methoxy, ethoxy, n-propoxy, isopropoxy and n-butoxy, preferably methoxy. The bond to the parent moiety is through the oxygen (if to a carbon atom, ether oxygen).

The term "alkoxy alkyl" means an alkyl group which is substituted by an alkoxy group, i.e. an alkyl-O-group as previously described. The bond to the alkyl moiety is through the oxygen i.e. it is an ether oxygen.

An "alkenyl" as used herein, alone or in combinations, means a straight or branched-chain unsaturated hydrocarbon group containing at least one carbon-carbon double bond, said hydrocarbon group containing preferably from 2 to 6, preferably 2 to 4 or 2 to 3 or 2 carbon atom(s) [i.e. "C(2-6)" "C(2-4)" or "C(2-3)" or "C(2-2)" alkyl groups].

The term "cycloalkyl" as used herein is a non-aromatic carbon-based alkyl ring composed of at least three carbon atoms.

A "heterocyclic" ring as used herein is a cyclic moiety that has, besides carbon atom(s), atoms of at least one non-carbon element(s) as member(s) of its ring(s). Preferably the ring(s) of the heterocyclic moiety is/are 5 to 6 membered ring(s).

The term "heterocycloalkyl" refers to a "heterocyclic" ring which is derivable from cycloalkyl group as defined above, wherein at least one of the carbon atoms of the ring is replaced with a heteroatom such as, but not limited to, nitrogen or oxygen.

The term "aryl" as used herein is a group that contains any carbon-based aromatic ring which is preferably a mono- or bicyclic group. The term aryl also includes optionally "heteroaryl" which is defined as a group that contains an aromatic group that has at least one heteroatom incorporated within the ring of the aromatic group. Examples of heteroatoms include but not limited to nitrogen and oxygen. Optionally, the term "aryl" is limited to non-heteroaryl which is also included into the term aryl and defines a group that contains an aromatic group that does not contain a heteroatom.

The term "aralkyl" as used herein refers to an aryl alkyl group which is linked to the parent molecule through the alkyl group, which may be further optionally substituted with one or more, preferably one to three or one to two substituents.

The term "cycloalkylaryl" refers to a group comprising a fused cycloalkyl and cycloaryl ring. Preferably the "cycloalkylaryl" moiety is attached to the compound of the invention via the cycloalkyl part of the group.

As used herein, the term "fused ring" means that the ring is fused with at least one other ring to form a group of a compound which comprises two or more rings wherein a single bond between two member atoms of the rings is, together with said two members, common in, i.e. shared by the two rings. An example of fused rings is a polycyclic aryl. A polycyclic aryl is understood herein as a group that contains multiple rings of a carbon-based group among which at least one ring is an aryl and which optionally may also comprise a cycloalkyl and/or a heterocycloalkyl.

A "substituted" moiety comprises a substituent selected from the groups and moieties as defined herein; however a substituent is smaller, i.e. shorter, i.e. consists of not more, preferably less atoms than the moiety which is/are substituted thereby.

When a moiety indicated in a formula is "not present" it means that there is a single (covalent) bond in the structure illustrated by the formula linking the atoms indicated in the vicinity of the moiety which is not present.

"Extracellular matrix" or "ECM" is the non-cellular component prescut in all tissues and organs. ECM is understood herein as the extracellular part of a multicellular tissue in a subject, preferably of a mammalian species, more preferably a human, that provides structural, biochemical and biological support and cell adhesion, cell to ECM and cell-to-cell communication to the surrounding cells. The ECM initiates crucial biochemical and biomechanical cues that are required for tissue morphogenesis, differentiation, homeostasis or in response to injury to regeneration or progressive fibrosis. It provides a substrate for cell anchorage, serves as a tissue scaffold, guides cell migration during embryonic development, wound repair, tissue remodeling and progressive fibrosis. The ECM is also responsible for transmitting environmental signals, such as releasing growth factors, cytokines to cells, which ultimately affects cell proliferation, differentiation and death.

ECM is a complex structural entity which is composed of three major classes of biomolecules:
1. Structural proteins: collagen and elastin
2. Specialized proteins: fibrillin, fibronectin and laminin
3. Proteoglycans having a net negative charge that attracts water and other molecules to contribute to the maintenance of ECM. Proteoglycans are composed of a protein core to which long chains of repeating disaccharide units termed glycosaminoglycans (GAGs) are attached, forming extremely complex high molecular weight components of the ECM.

"Collagens" are the most abundant and main structural proteins in the ECM, being present in the ECM as fibrillar proteins, fibril-associated collagen with interrupted triple helices (FACIT), membrane-associated collagen with interrupted triple helices (MACIT), multiplex triple helix domains and interruptions (Multiplexin), Long chain, Short chain, Filamentous and Basement membrane and giving structural support to resident cells [Janna K et al. *Nature Rev Mol Cell Biol* 15, 771-785 (2014)].

Preferably, collagen is exocytosed in precursor form (procollagen), which is then cleaved by procollagen proteases to allow extracellular assembly.

Collagens can be divided into several families according to the types of structure they form.
Fibrillar: Type I, II, III, V, VII, XI, XXIV, XXVII
FACIT: Type IX, XII, XIV, XVI, XIX, XX, XXI, XXII
MACIT: Type XIII, XVII, XXIII
Multiplexin: Type XV, XVIII
Long chain: Type VII
Short chain Type VIII, X
Filamentous: Type VI
Basement membrane: Type IV Preferably, collagen fibers are composed of triple helices having a common motif in the amino acid sequence of collagen "glycine-proline-X" and "glycine-X-hydroxyproline", where X is any amino acid other than glycine, proline or hydroxyproline. Preferably the collagens comprise at least 20% or at least 25% or at least 30% or at least 32% of glycine, and preferably at most 50% or at most 40% or at most 35% or 34% of glycine per total number of their amino acids.

"Remodeling of ECM" is a series of quantitative and qualitative changes in the ECM during developmental processes, response to injury and regenerative processes that maintain tissue homeostasis. The components of the ECM are degradable and subject to modification. The final amount of deposited ECM and the composition thereof depends on the balance between the synthesis and degradation of the components of ECM.

"Deposition of ECM" is understood herein as a process during remodeling of ECM leading to an increase in the amount of ECM components in a space between (i.e. outside) the cells of a tissue.

An "excessive" deposition of ECM occurs when deposition of ECM components leads to impairment, i.e. destruction of tissue architecture and/or tissue function itself. The excessive or unregulated deposition of ECM components is a particular hallmark of progressive fibrosis and abnormal repair processes in different tissues upon injury. Preferably, deposition of ECM components is considered as "excessive" when there are no signs that regulatory processes of the tissue in question counter-acting deposition are capable of reversing, or at least arresting such deposition.

"Myofibroblasts" are cells with different origin, which express ECM components and have an increased ability of contraction and isometric tension as compared with its precursor cells.

Preferably the myofibroblasts are characterized by αSMA expression and by the incorporation of αSMA into stress fibres. Preferably the myofibroblasts, as understood herein, produce different component of the ECM and contribute to the remodeling of ECM. Preferably myofibroblasts differentiate from fibroblasts, bone-marrow derived fibrocytes, pericytes, epithelial cells, endothelial cells, smooth muscle cells and hepatic stellate cells.

"Accumulation of" cells in a tissue include herein or comprises one or more of the following:
proliferation of said cells and/or
differentiation of said cells from a precursor cell, and/or
increasing the number of said cells in said tissue by migration thereof from other tissue including recruitment of said cells, and/or
activation of said cells from a non-active variant or precursor.

"Progressive fibrosis" or "fibrosis" in short is characterized by a process when ECM remodeling is shifted towards accumulation of ECM producing cells, like myofibroblasts, and/or towards excessive deposition of ECM components leading to impairment or destruction of tissue architecture and/or to gradual decline of organ function.

Progressive fibrosis may turn into a pathological process leading to the formation of permanent scar tissue, may cause tissue or organ failure and might lead to death. In "progressive fibrosis" ECM components and ECM producing cells, in particular fibrillar ECM components like type I and III collagen and fibronectin, as well as the cells producing them continue to accumulate even beyond the homeostatic/regenerative phase of ECM remodeling. Excessive production and/or rearrangement of actin filaments in the fibrotic cells is also a hallmark of progressive fibrosis.

The process in which an excessive amount of ECM replaces normal parenchyma or the ECM which is typical to the tissue affected by progressive fibrosis may also be considered "progressive fibrosis". This process is characterized by overproliferation of ECM producing cells, e.g. myofibroblasts, and excessive or unregulated deposition of ECM components and/or abnormal repair processes in different tissues upon injury.

"Fibroproliferative disorder" is a disorder which is characterized by inter alia the presence of progressive fibrosis, in particular wherein at least partially ECM remodeling is shifted towards accumulation of ECM producing cells, like myofibroblasts, and/or towards excessive deposition of ECM components leading to impairment or destruction of tissue architecture and/or to gradual decline of organ function.

The term "comprises" or "comprising" or "including" are to be construed here as having a non-exhaustive meaning and allow the addition or involvement of further features or method steps or components to anything which comprises the listed features or method steps or components. "Comprising" can be substituted by "including" if the practice of a given language variant so requires or can be limited to "consisting essentially of" if other members or components are not essential to reduce the invention to practice.

BRIEF DESCRIPTION OF THE FIGURES

FIGS. 6A-H show the development of tubulointerstital fibrosis in the kidney sections of Streptozotocin-(65 mg/bwkg iv.) induced type 1 diabetic rats treated per os with (D): vehicle (isotonic saline); (D+7FLU): fluvoxamine (20 mg/bwkg/day) for 7 weeks or (D+FLU): fluvoxamine (20 mg/bwkg/day) for 2 weeks from the $5^{th}$ week of diabetes,) or (D+FLU2): fluvoxamine (2 mg/bwkg/day) for 2 weeks from the $5^{th}$ week of diabetes. Additional groups were also treated per os with NE-100, a specific antagonist of S1R; (D+FLU+NE-100): fluvoxamine+NE-100 (20 mg/bwkg/day+1 mg/bwkg/day) for two weeks or (D+FLU2+NE-100): fluvoxamine+NE-100 (2 mg/bwkg/day+1 mg/bwkg/day) for two weeks from the $5^{th}$ week of diabetes. Masson's trichrome staining of kidney sections was performed and the fibrotic area per total area was calculated. Average volumetric mesangial matrix expansion given relative to the total area in case of animal groups (6/A 1-7) (Bars represent Mean±SEM, n=8-10/group, 20× magnification; scale bar –100 μm). Specifically:

FIG. 6A shows Control non-diabetic rats treated with isotonic saline, as vehicle only FIG. 6B shows Diabetic rats treated with isotonic saline, as vehicle only FIG. 6C shows Diabetic rats treated fluvoxamine (20 mg/bwkg/day) for 7 weeks FIG. 6D shows Diabetic rats treated fluvoxamine (20 mg/bwkg/day) for 2 weeks from the $5^{th}$ week of diabetes FIG. 6E shows Diabetic rats treated fluvoxamine (20 mg/bwkg/day)+NE-100 (1 mg/bwkg/day) for 2 weeks from the $5^{th}$ week of diabetes FIG. 6F shows Diabetic rats treated fluvoxamine (2 mg/bwkg/day) for 2 weeks from the $5^{th}$ week of diabetes FIG. 6G shows Diabetic rats treated fluvoxamine (2 mg/bwkg/day)+NE-100 (1 mg/bwkg/day) for 2 weeks from the $5^{th}$ week of diabetes FIG. 6H shows Average volumetric tubulointerstitial fibrosis given relative to the total area in case of animal groups FIGS. 7A-H. Sigma-1 receptor (S1R) agonist compound fluvoxamine decreases diabetes induced mesangial matrix expansion in the kidney of diabetic rats

FIG. 7A shows Control non-diabetic rats treated with isotonic saline, as vehicle only FIG. 7B shows Diabetic rats treated with isotonic saline, as vehicle only FIG. 7C shows Diabetic rats treated fluvoxamine (20 mg/bwkg/day) for 7 weeks FIG. 7D shows Diabetic rats treated fluvoxamine (20 mg/bwkg/day) for 2 weeks from the $5^{th}$ week of diabetes FIG. 7E shows Diabetic rats treated fluvoxamine (20 mg/bwkg/day)+NE-100 (1 mg/bwkg/day) for 2 weeks from the $5^{th}$ week of diabetes FIG. 7F shows Diabetic rats treated fluvoxamine (2 mg/bwkg/day) for 2 weeks from the $5^{th}$ week of diabetes FIG. 7G shows Diabetic rats treated fluvoxamine (2 mg/bwkg/day)+NE-100 (1 mg/bwkg/day) for 2 weeks from the 5$^{th}$ week of diabetes FIG. 7AH shows Average volumetric mesangial matrix expansion given per glomeruli (glom) for animal groups of FIGS. 7A-G FIGS. 8A-E. Sigma-1 receptor (S1R) agonist compound fluvoxamine treatment decreases diabetes induced fibronectin accumulation in the kidney of diabetic rats

FIG. 8A shows Control non-diabetic rats treated with isotonic saline, as vehicle only FIG. 8B shows Diabetic rats treated with isotonic saline, as vehicle only FIG. 8C shows Diabetic rats treated fluvoxamine (20 mg/bwkg/day) for 2 weeks from the 5$^{th}$ week of diabetes FIG. 8D shows Diabetic rats treated fluvoxamine (20 mg/bwkg/day)+NE-100 (1 mg/bwkg/day) for 2 weeks from the 5$^{th}$ week of diabetes FIG. 8E shows Average volumetric fibronectin positive area (given per total area) for animal groups of

FIGS. 8A-D

FIGS. 9A-E. Sigma-1 receptor (S1R) agonist compound fluvoxamine treatment decreases diabetes induced extracellular matrix (ECM) production in the kidney of diabetic rats FIGS. 9A-E show accumulation of fibrillar ECM components in the kidney sections of Streptozotocin-(65 mg/bwkg iv.) induced type 1 diabetic rats treated per os with (D): vehicle (isotonic saline); (D+7FLU): fluvoxamine (20 mg/bwkg/day) for 7 weeks or (D+FLU): fluvoxamine (20 mg/bwkg/day) for 2 weeks from the 5$^{th}$ week of diabetes. Kidney sections were stained with 0.1% Sirius Red and the fractional volume values (Vv) are defined by the ratio of Sirius red-positive per total area. (Bars represent Mean±SEM, n=8-10/group, 20× magnification; scale bar— 50 μm). Specifically:

FIG. 9A shows Control non-diabetic rats treated with isotonic saline, as vehicle only FIG. 9B shows Diabetic rats treated with isotonic saline, as vehicle only FIG. 9C shows Diabetic rats treated fluvoxamine (20 mg/bwkg/day) for 7 weeks FIG. 9D shows Diabetic rats treated fluvoxamine (20 mg/bwkg/day) for 2 weeks from the 5$^{th}$ week of diabetes FIG. 9E shows Average volumetric Sirius Red positive area given per total area for animal groups of FIGS. 9A-D FIG. 10. Sigma-1 receptor (S1R) agonist compound fluvoxamine treatment decreases diabetes induced α-smooth muscle (αSMA) protein level in the kidney of diabetic rats FIG. 10 demonstrates the protein level of αSMA in kidney homogenates of Streptozotocin-(65 mg/bwkg iv.) induced type 1 diabetic rats treated per os with (D): vehicle (isotonic saline); (D+7FLU): fluvoxamine (20 mg/bwkg/day) for 7 weeks or (D+FLU): fluvoxamine (20 mg/bwkg/day) for 2 weeks from the 5$^{th}$ week of diabetes,) or (D+FLU2): fluvoxamine (2 mg/bwkg/day) for 2 weeks from the 5$^{th}$ week of diabetes. Additional groups were also treated per os with NE-100, a specific antagonist of S1R; (D+FLU+NE-100): fluvoxamine+NE-100 (20 mg/bwkg/day+1 mg/bwkg/day) for two weeks or (D+FLU2+NE-100): fluvoxamine+NE-100 (2 mg/bwkg/day+1 mg/bwkg/day) for two weeks from the 5$^{th}$ week of diabetes (Bars represent Mean±SEM, n=8-10/group). Upper panel shows representative picture of western blot of αSMA.

FIGS. 11A-E. Sigma-1 receptor (S1R) agonist compound fluvoxamine treatment minimizes tubulointerstitial fibrosis in the kidney after unilateral ureteral obstruction (UUO)

FIGS. 11A-E shows the development of tubulointerstital fibrosis in kidneys of six-week old mice 7 days after having UUO. Mice were treated once daily by oral gavage for one week with vehiculum (UUO), or with fluvoxamine (20 mg/bwkg/day) or with fluvoxamine+S1R antagonist NE-100 (1 mg/bwkg/day). Kidney sections were stained for Masson's trichrome and the ration of Masson positive/total area was calculated (Bars represent Mean±SEM, n=6/group, 20× magnification; scale bar –100 μm). Specifically:

FIG. 11A shows Sham operated, control mice treated with vehicle only

FIG. 11B shows Mice with UUO treated with vehicle only

FIG. 11C shows Mice with UUO treated with vehicle only treated with fluvoxamine (20 mg/bwkg/day) for one week FIG. 11D shows Mice with UUO treated with vehicle only treated with fluvoxamine (20 mg/bwkg/day) +NE-100 (1 mg/bwkg/day) for one week FIG. 11E shows Average volumetric tubulointerstitial fibrosis given by Masson stained area per total area for animal groups of FIGS. 11-A-D.

FIG. 12 demonstrates the protein level of αSMA in kidney homogenates of six-week old mice 7 days after having UUO. Mice were treated once daily by oral gavage for one week with vehicle (UUO), or with fluvoxamine (20 mg/bwkg/day). (Bars represent Mean±SEM, n=6/group). Upper panel shows representative picture of western blot of αSMA.

FIGS. 13A-E represent the development of lung fibrosis two weeks after the intratracheal injection of bleomycin in rats treated with vehicle (with or without sham operation) or with fluvoxamine (20 mg/bwkg/day) or with fluvoxamine+ S1R antagonist NE-100 (1 mg/bwkg/day) for three weeks. Masson trichrome staining of tissue sections was performed Bars represent Mean±SEM, n=6/group). Specifically:

FIG. 13A shows Control non-bleomycin injected, sham operated rats treated with vehicle only FIG. 13B shows Bleomycin injected rats treated with vehicle only FIG. 13C shows Bleomycin injected rats treated with fluvoxamine (20 mg/bwkg/day) for two weeks FIG. 13D shows Bleomycin injected rats treated with fluvoxamine (20 mg/bwkg/day)+NE-100 (1 mg/bwkg/day) for three weeks FIG. 13E shows Average Masson-stained fibrotic pixels relative to all pixels for animal groups of FIGS. 13A-D FIG. 14. Sigma-1 receptor (S1R) agonist compound fluvoxamine treatment diminishes α-smooth muscle (αSMA) production in a rat model of bleomycin-induced lung fibrosis.

It should be noted that the term "fibroblast" is used to indicate "myofibroblast" in the figure legends.

Figure 15A:
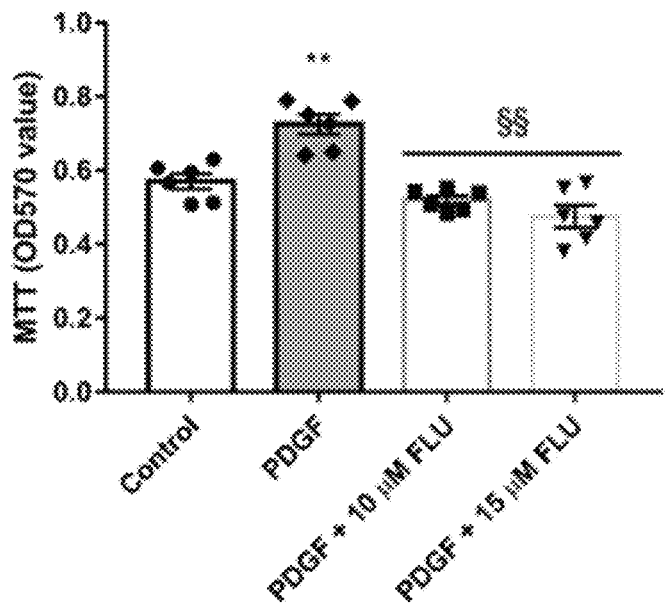
Figure 15B:
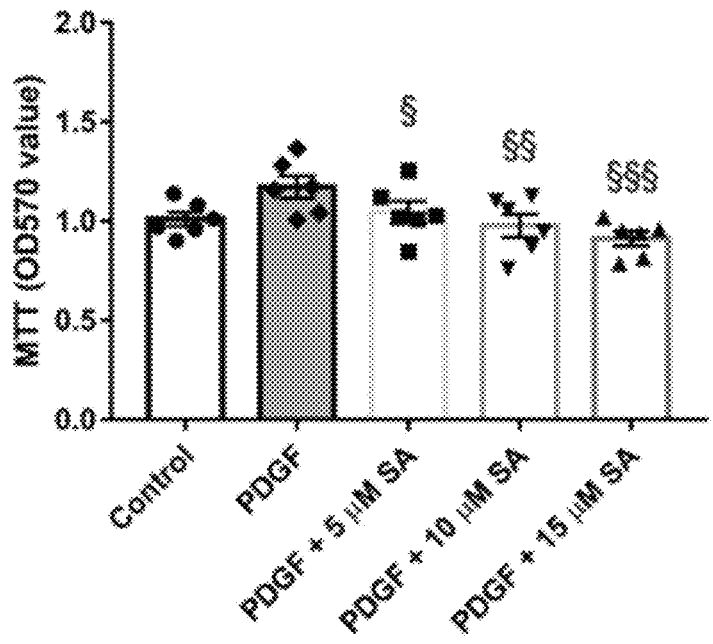
Figure 15C:
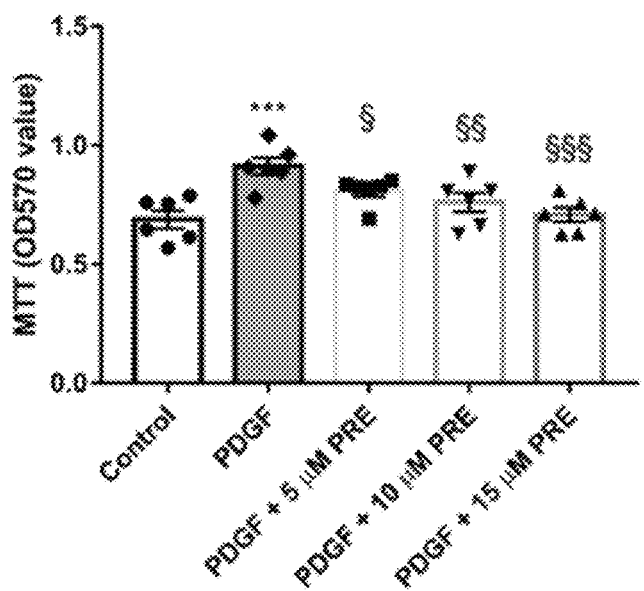

FIGS. 15A-C. Sigma-1 receptor (S1R) agonists suspend platelet-derived growth factor (PDGF)-induced cell proliferation in human trabecular meshwork-5 (HTM-5) cells.

(FIG. 15A) MTT assay of 20 ng/mL platelet-derived growth factor (PDGF), 20 ng/mL PDGF+10 μM fluvoxamine (FLU), 20 ng/mL PDGF+15 μM FLU treatment for 24 h in human trabecular meshwork-5 (HTM-5) cells. (FIG. 15B) MTT assay of 20 ng/mL PDGF, 20 ng/mL PDGF+5 μM sigma-1 receptor (S1R) agonist SA-4503 (SA), 20 ng/mL PDGF+10 μM SA, 20 ng/mL PDGF+15 μM SA treatment for 24 h in HTM-5 cells. (FIG. 15C) MTT assay of 20 ng/mL PDGF, 20 ng/mL PDGF+5 μM S1R agonist PRE-087 (PRE), 20 ng/mL PDGF+10 μM PRE, 20 ng/mL PDGF+15 μM PRE treatment for 24 h in HTM-5 cells. All data are shown as mean±SEM; n=6/group. *p<0.05 vs. Control; ***p<0.001 vs. Control; § p<0.05 vs. PDGF; §§ p<0.01 vs. PDGF; §§ p<0.001 vs. PDGF.

Figure 16A:
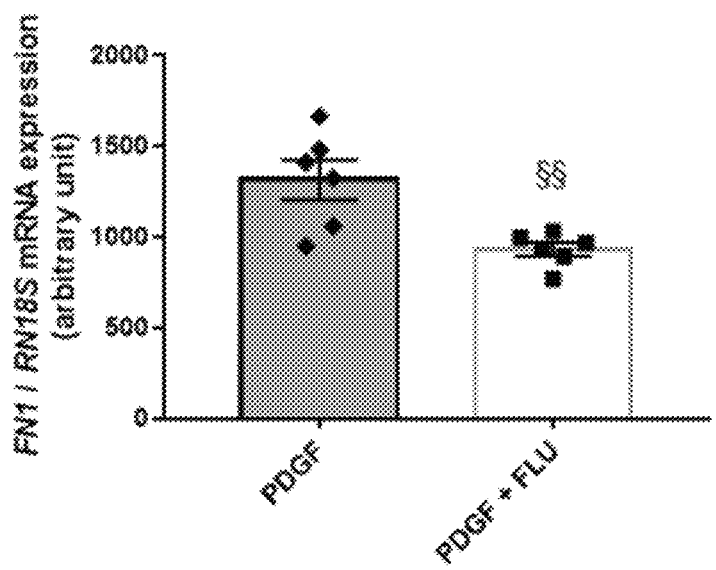
Figure 16B:
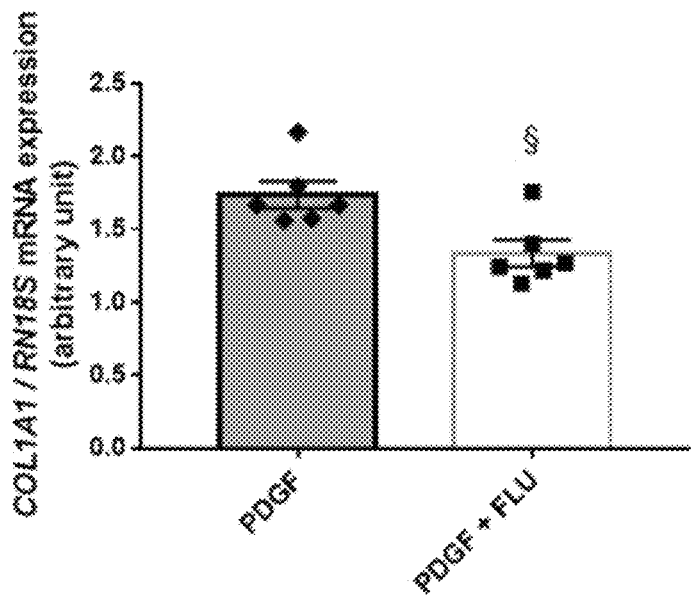
Figure 16C:
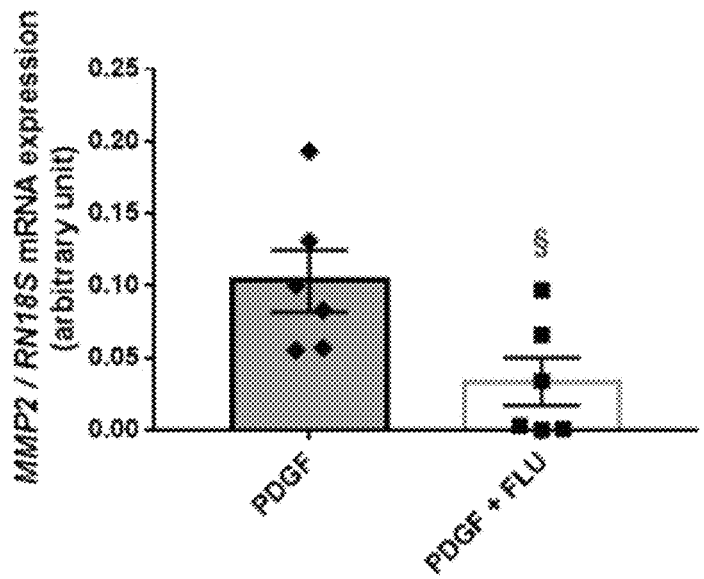

FIGS. 16A-C. S1R receptor agonist fluvoxamine reduces fibrotic markers in HTM-5 cells.

FIG. 16A. Total RNA of FN1 (fibronectin) expression determined in human trabecular meshwork-5 (HTM-5) cells treated with 20 ng/ml platelet-derived growth factor (PDGF) (grey bar) and with 20 ng/ml PDGF plus 5 μM fluvoxamine (FLU) (white bar).

FIG. 16B. Total RNA of COL1A1 (collagen1a1) expression determined in human trabecular meshwork-5 (HTM-5) cells treated with 20 ng/ml PDGF (grey bar) and with 20 ng/ml PDGF plus 5 μM fluvoxamine (FLU) (white bar).

FIG. 16C. Total RNA MMP2 (matrix metalloproteinase 2) expression determined in human trabecular meshwork-5 (HTM-5) cells treated with 20 ng/ml PDGF (grey bar) and with 20 ng/ml PDGF plus 10 μM FLU (white bar).

In each of FIGS. 16A, 16B and 16C total RNA was represented by comparison with RN18S mRNA as internal control from the same samples. All data are shown as means±SEMs; n=6/group. § p<0.05 vs. PDGF; §§ p<0.01 vs. PDGF.

Figure 17A:
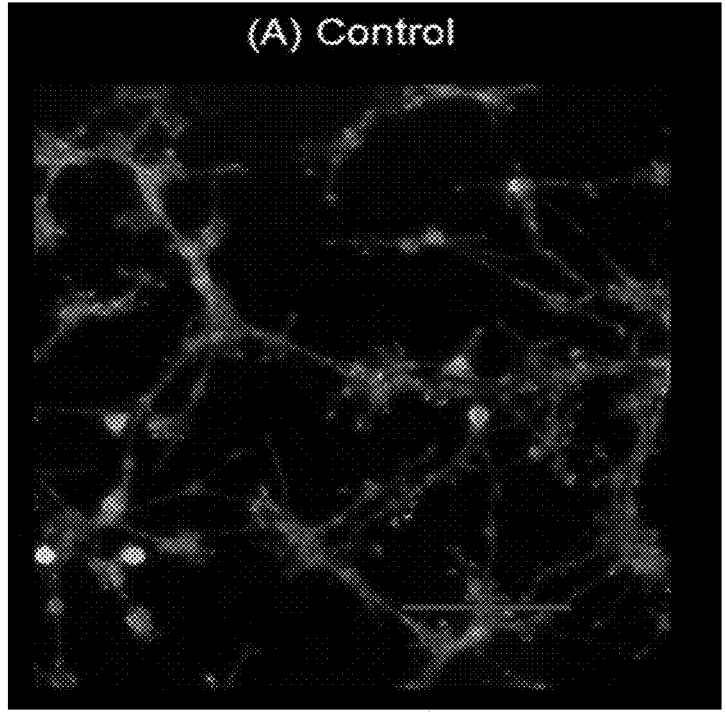
Figure 17B:
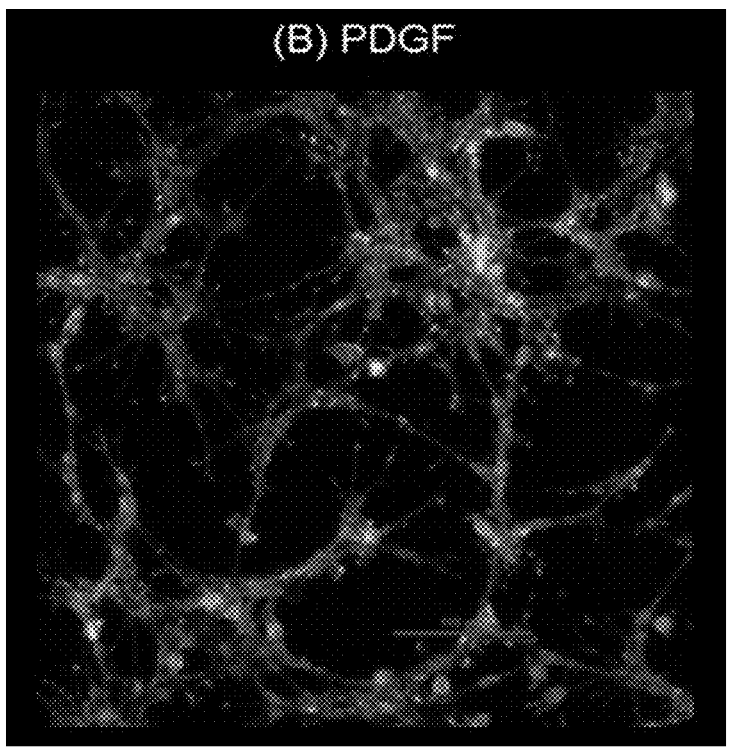
Figure 17C:
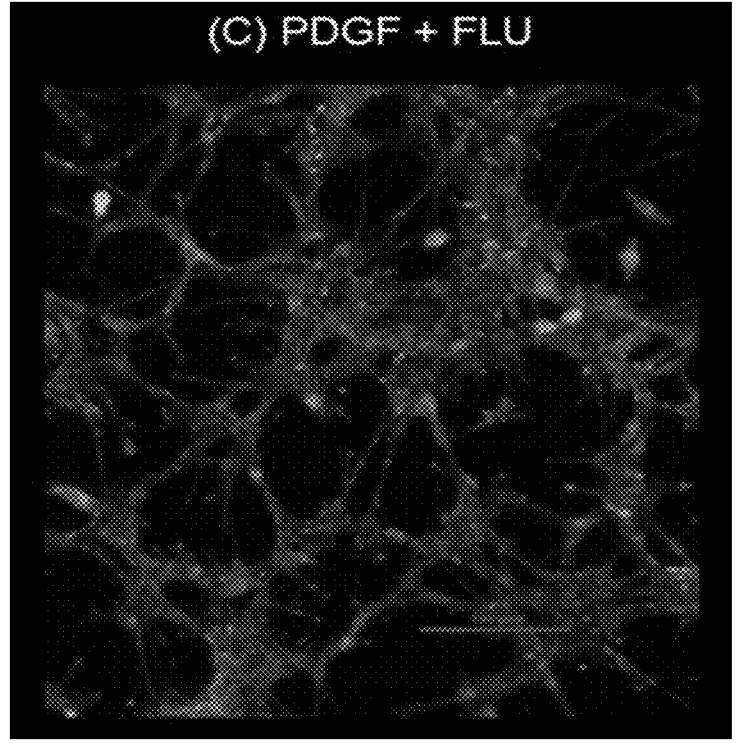

FIGS. 17A-C. Effect of PDGF and S1R agonist FLU on actin cytoskeleton rearrangement in HTM-5 cells.

Representative pictures of phalloidin immunostained human trabecular meshwork-5 (HTM-5) cells treated with platelet-derived growth factor (PDGF) or with PDGF plus fluvoxamine (FLU); 1000× magnification; yellow: F-actin; blue: nucleus; scale bar=100 μm FIG. 17A. HTM-5 cells, untreated (Control);

FIG. 17B. HTM-5 cells, treated for 24 h with 20 ng/mL PDGF;

FIG. 17C HTM-5 cells, treated for 24 h with 20 ng/mL PDGF and 10 μM FLU (PDGF+FLU).

Figure 18A:
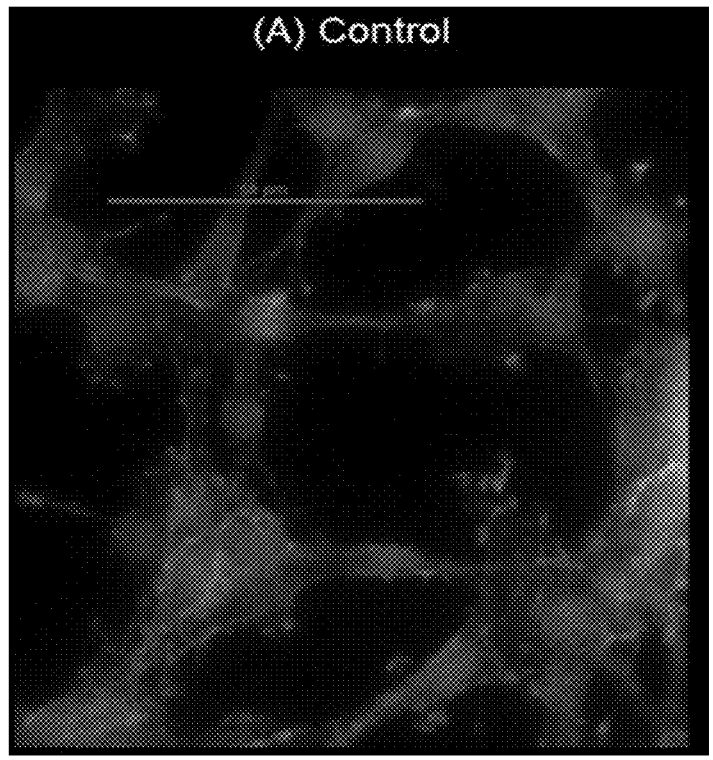
Figure 18B:
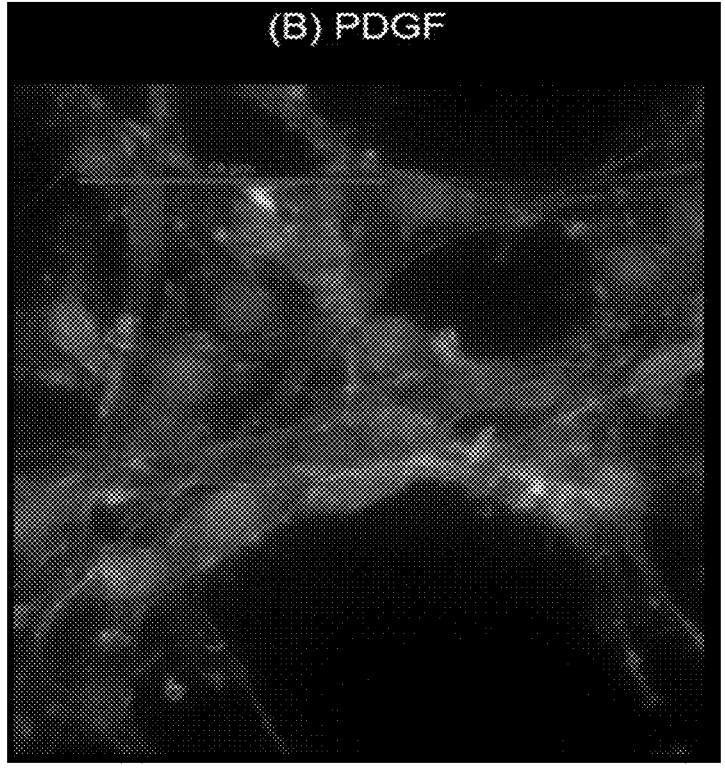
Figure 18C:
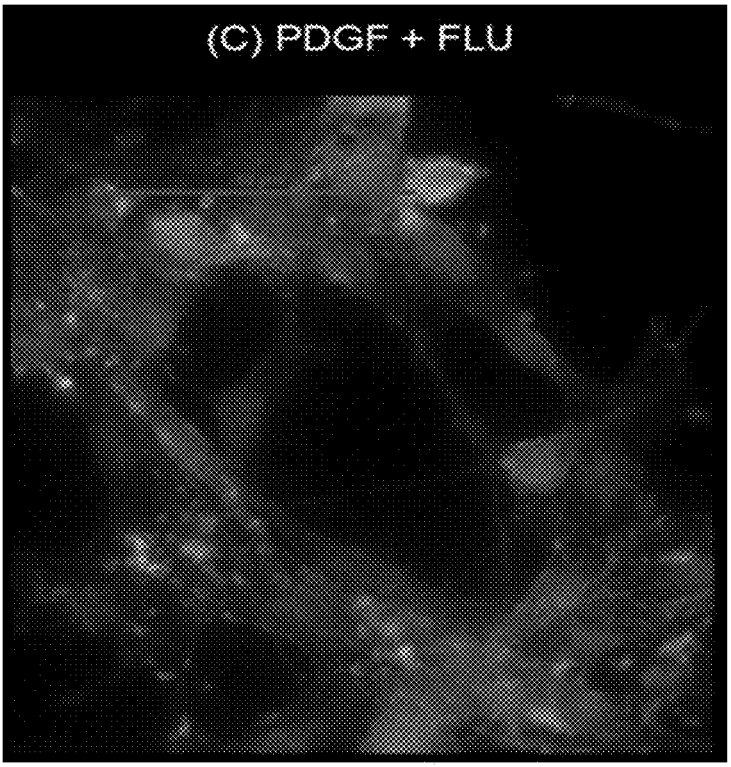

FIGS. 18A-C. Effect of PDGF and S1R agonist FLU on actin cytoskeleton rearrangement in HTM-5 cells.

Representative pictures of phalloidin immunostained human trabecular meshwork-5 (HTM-5) cells treated with platelet-derived growth factor (PDGF) or with PDGF plus fluvoxamine (FLU); 6000× magnification; yellow: F-actin; blue: nucleus; scale bar=50 μm FIG. 18A. HTM-5 cells, untreated (Control);

FIG. 18B. HTM-5 cells, treated for 24 h with 20 ng/mL PDGF;

FIG. 18C HTM-5 cells, treated for 24 h with 20 ng/mL PDGF and 10 μM FLU (PDGF+FLU).

DETAILED DESCRIPTION OF THE INVENTION

Progressive fibrosis is a common pathological response in many medical conditions. According to some estimates almost the half of all deaths is attributed to progressive organ fibrosis in the western world. For example, chronic Kidney Diseases (CKD) affect the 8-16% of the population worldwide and the number of them is continuously increasing mainly due to the increasing number of the diabetic patients.

Progressive fibrosis is initiated by the sustained production of growth factor, proteolytic enzymes, angiogenic factors and/or fibrogenic cytokines, leading to progressive and excessive production of ECM components. In cases of progressive fibrosis when this process is not regulated to cease or reverse, the accumulation (and contraction) of ECM results in the expansion and stiffening of the interstitium that surrounds parenchymal units and disrupts their physiological function [Klingberg F et al. *J Pathol.* 229(2), 298-309 (2013)].

Thus, in conditions of injuries or disturbed tissue or organ homeostasis usually accompanied by inflammation, resident and infiltrating immune cells secrete cytokines and growth factors, like platelet-derived growth factor (PDGF), transforming growth factor-β (TGFβ), epidermal growth factor (EGF), fibroblast growth factor (FGF), insulin-like growth factor (IGF), connective tissue growth factor (CTGF), glucose, angiontensin II, or aldosterone and various interleukins (IL-1alpha, IL-1β, IL-4, IL-8, IL-13). These mediators facilitate formation and accumulation of αSMA expressing and ECM-producing myofibroblasts.

Myofibroblasts and the ECM in which they reside are critical components of the progressive fibrotic process. The ECM is actually a functional tissue whose components possess not only scaffolding characteristics, but also growth factor, mitogenic, and other bioactive properties. Progressive fibrosis oftentimes is leading to organ dysfunction and increased morbidity or mortality, and it is also associated with a kind of dysregulation of the tissue processes in disturbed tissue homeostasis [Lekkerkerker S et al. *Curr Pharm Des.* 18(27), 4093-102 (2012)]. Thus, progressive fibrosis is a condition that cannot be considered homeostatic and/or serves no longer as a regenerative process; it might be associated with a disease or may constitute a condition that requires medical treatment.

The present inventors have unexpectedly recognized that fluvoxamine, the potent Sigma-1 receptor (S1R) agonists is useful in the prevention and/or inhibition of fibrotic remodeling of ECM and thereby in progressive fibrotic conditions. Specifically the inventors discovered that fluvoxamine successfully improves the impairment of renal function associated with renal fibrosis (confirmed by the improvement in conventional, gold-standard, clinical parameters e.g. GFR, creatinine, serum urea nitrogen etc). Furthermore they demonstrated that S1R agonists have an anti-fibroproliferative potential also in various tissues.

As explained below it is understood herein that accumulation of myofibroblasts and/or overproduction and deposition of ECM components may be indicative of and/or associated with progressive fibrosis associated with pathological conditions and which may occur in several disorders. Treatment of progressive fibrosis, however, can be differentiated from the treatment of the disease which is accompanied by said progressive fibrosis and may even be independent therefrom.

Thus, according to the invention in a given condition or in a given subject/patient the treatment may be directed to prevention, control, reversal or inhibition of fibrotic remodeling of ECM preferably including accumulation of myofibroblast and/or excessive production and deposition of ECM components, e.g. fibrillar components thereof, including collagen, preferably type I and III collagen or fibronectin or excessive production and/or rearrangement of actin filaments in the fibrotic cells. Thereby the present invention may lead to the amelioration of the patient's condition regarding the underlying or causative disease e.g. as listed herein.

The invention provides compounds and compositions for use in the prevention or treatment of progressive fibrosis, in particular in the prevention, control, reversal or inhibition of progressive fibrosis. Once fibrotic processes are inhibited or prevented, this may allow the regenerative mechanisms of the organism to take place. Thereby a fibrotic condition may even be reversed.

The Sigma Receptor

The Sigma receptor is as a ligand-regulated molecular chaperon in the endoplasmic reticulum. Sigma receptors consist of two subtypes, Sigma-1 and Sigma-2 (S1R and S2R) receptors (alternative names: sigma non-opioid intracellular receptor, AAG8, ALS16, Aging-associated gene 8 protein, OPRS1, SIG-1R). The S1R was cloned in 1996 and its molecular conformation was then explored. S1R and S2R receptors have no close homology to any other mammalian proteins. The human 223-amino acid protein S1R is localized in various tissues including the brain, intestine, liver, spleen, lung, kidney, skeletal muscle, adrenal glands, genital tract, skin and eye [Hanner M et al. *Proc Natl Acad Sci USA*. 93(15). 8072-8077 (1996)]. S1R can be found in a large number on the endoplasmic reticulum, in particular on the mitochondria-associated ER membrane where they proposed to function as "receptor chaperones" However outside the central nervous system the function and regulation of the S1R is almost unknown.

S1R has been suggested to take part in a number of diseases of the central nervous system. The primary therapeutic targets of agonists include schizophrenia, major depression, obsessive-compulsive disorder (OCD), and Alzheimer's disease and major depressive disorder [Ishikawa M et al. *Journal of Receptor, Ligand and Channel Research* 3, 25-3 (2010)]. Information is scarce about the potential role and use of S1R agonists outside the central nervous system. Furthermore, the study of clinical potential of S1R agonists is in its very beginning.

It is contemplated that in principle any S1R receptor agonists might be applicable in the present invention. Preferred are S1R agonists which are selective over S2R. Also preferred are S1R agonists which have a strong affinity to S1R receptor and which have less side-effects.

A compound is selective for S1R over S2R if it has a higher affinity for S1R than S2R, preferably 5 times higher or 20 times higher or 50 times higher or at least $10^2$ higher, at least $10^3$ higher or at least $10^4$ higher.

S1R agonists belong to various structural groups of compounds. In the present invention compounds as defined in the brief description of the invention are preferred.

In the experimental part illustrative experiments are shown with three S1R agonist compounds: fluvoxamine, SA-4503 (cumetasine) and PRE-84. Each compound has different structures and each of them has been surprisingly found to be active in controlling progressive fibrosis. Fluvoxamine was found to be successful even in preventing, inhibiting and reversing progressive fibrosis in the kidney and in the lung. As it has been shown, other S1R agonists, e.g. SA-4503 (cumetasine) and PRE-84 have the same effect in vivo. Fluvoxamine is particularly preferred.

In a further set of experiment the same three S1R agonist compounds, fluvoxamine, SA-4503 (cumetasine) and PRE-84 were used to inhibit progressive fibrosis in an in vitro model of progressive fibrosis of the eye HTM-5 cell wherein progressive fibrosis has been artificially elicited by PDGF. Excessive fibrotic proliferation of cells, expression of matrix components indicating fibrosis, as well as active overproduction and rearrangement of F-actin filaments were reversed by different Sigma-1 receptor agonists. HTM cells can be obtained e.g. from DELL APPLICATIONS INC, San Diego, Calif., USA.

In Table A below a number of S1R receptor agonist are listed which are contemplated for use according to the invention.

TABLE A

| Name | Formula | IUPAC name |
|---|---|---|
| fluvoxamine | | 2-{[(E)-{5-Methoxy-1-[4-(trifluoromethyl)phenyl]pentylidene}amino]oxy}-ethanamine |
| fluoxetine | | N-methyl-3-phenyl-3-[4-(trifluoromethyl)phenoxy]propan-1-amine |

TABLE A-continued

| Name | Formula | IUPAC name |
| --- | --- | --- |
| sertraline | | (1S,4S)-4-(3,4-dichlorophenyl)-N-methyl-1,2,3,4-tetrahydronaphthalen-1-amine |
| SA 4503 (cutamesine) | | 1-[2-(3,4-Dimethoxyphenyl)ethyl]-4-(3-phenylpropyl)piperazine |
| BD1031 | | (8aR)-2-[2-(3,4-Dichlorophenyl)ethyl]octahydropyrrolo[1,2-a]pyrazine |
| BD1052 | | N-[2-(3,4-dichlorophenyl)ethyl]-N-(2-pyrrolidin-1-ylethyl)prop-2-en-1-amine |
| 4-IBP | | N-(N-Benzylpiperidin-4-yl)-4-iodobenzamide |
| PRE-084 | | 2-morpholin-4-ylethyl 1-phenylcyclohexane-1-carboxylate |
| Pentoxyverine (rINN) or carbetapentane | | 2-[2-(diethylamino)ethoxy]ethyl 1-phenylcyclopentanecarboxylate |

TABLE A-continued

| Name | Formula | IUPAC name |
|---|---|---|
| (±)-PPCC oxalate | 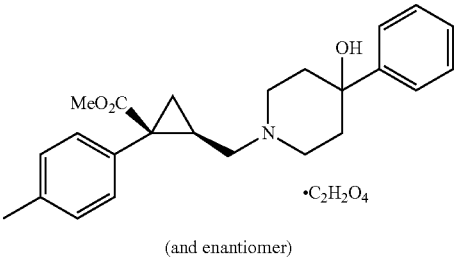 (and enantiomer) | (S*,R*)-2-[(4-Hydroxy-4-phenyl-1-piperidinyl)methyl]-1-(4-methylphenyl)-cyclopropanecarboxylic acid methyl ester |
| haloperidol metabolite II (reduced haloperidol) | 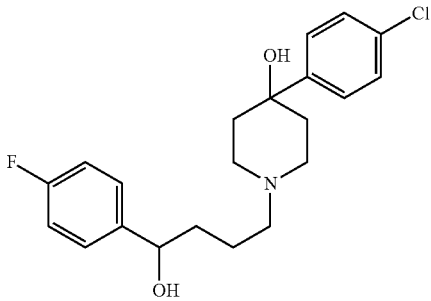 [SMILES: OC(CCCN1CCC(O)(c2ccc(Cl)cc2)CC1)c1ccc(F)cc1] | 4-[4-(4-Chlorophenyl)-4-hydroxy-1-piperidyl]-1-(4-fluorophenyl)-butan-1-ol |
| ANAVEX2-73 Tetrahidro-N,N-dimetil-2,2-difenil-3-furánmeténamin HCl | 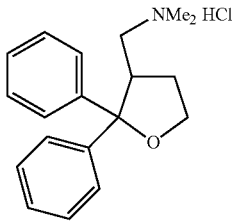 | Tetrahydro-N,N-dimethyl-2,2-diphenyl-3-furanmethanamine hydrochloride |
| RC-33 | 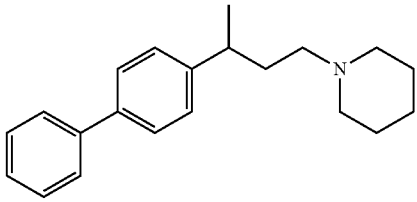 [SMILES: CC(CCN1CCCCC1)c1ccc(-c2ccccc2)cc1] | 1-[1-(4-biphenyl)-1-methyl-propyl]piperidine |

S1R agonists for use in the present invention can be prepared according to methods known for a skilled person or are commercially available like fluvoxamine, SA-4503, PRE-084, 4-IBP, ANAVEX2-73, etc.

For example, fluvoxamine maleate can be prepared as described in U.S. Pat. No. 4,085,225 and in U.S. Pat. No. 6,433,225 B1.

EP2353598A1 discloses synthesis of sigma-receptor ligands including cumetasine and related compounds.

PRE-084 is a high affinity, sigma-receptor agonist, selective for the S1R subtype (Kis=2.2 and 13,091 nM for σ1 and σ2 receptors, respectively). It is a potent ligand of the S1R (IC50=44 nM) without appreciable affinity for PCP receptors (IC50>100,000 nM) and its availability is described e.g. [Griesmaier E et al. *Experimental Neurology* 237(2), 388 395 (2012)]. Rossi, Daniela et al. describe the synthesis of sigma-receptor ligands based on arylalkenylaminic scaffold, among others RC-33, see Table A [Rossi D et al. *Bioorganic & Medicinal Chemistry* 19(21), 6210-6224 (2011)].

It is known for a large number of compounds that they are S1R agonist. To test binding affinity and measure dissociation constant can be done by usual methods in protein and bioorganic chemistry.

For example Xu, Rong et al. disclose the effect of ether modifications to SA-4503 on binding affinity and selectivity for sigma receptors and monoamine transporters and methods to measure these parameters [Rong Xu et al. *Bioorganic & Medicinal Chemistry* 23(1), 222-230 (2015)].

Furthermore, Rossi, Daniela et al. (see above) selected and identified a potent and selective S1R agonist among a number of compounds and described related methods. Moreover, the authors have developed a three dimensional S1R pharmacophore model using active compounds only to derive this model. The model included two hydrophobes and a positive nitrogen as relevant features and it was able to discriminate between molecules with and without affinity toward σ1 receptor subtype. Thus, it is well within the skills of a person skilled in the art to prepare and select compounds according to the invention.

As also shown in the Examples below, it is well within the skills of a person skilled in the art to test whether a potential S1R agonist is actually an agonist.

A usual method to test whether an S1R agonist acts on the S1R is to use a specific antagonist, as a control. Such a well-accepted specific antagonist is NE-100 which is a potent and selective S1R antagonist ($K_i$=0.86 nM) that displays >55-fold selectivity over S2R and >6000-fold selectivity over $D_1$, $D_2$, 5-$HT_{1A}$, 5-$HT_2$ and PCP receptors (4-Methoxy-3-(2-phenylethoxy)-N,N-dipropylbenzeneethanamine hydrochloride). NE-100 exhibits reversible binding ($K_d$=1.2 nM) [Okuyama S et al. *CNS Drug Rev.* 2(2), 226-237 (1999), Berardi F et al. *Bioorg. Med. Chem.* 9(5), 1325-35 (2001)].

Below a few diseases are listed as examples that often or even necessarily associated with progressive fibrosis and a few options to treat progressive fibrosis are mentioned. It is to be understood, however, that these examples though may be preferred, are merely illustrative. As progressive fibrosis may occur in a number of disorders other embodiments of the invention may be reduced into practice without departing from the concept and scope of the present invention. Typically these disease conditions are accompanied by abnormal proliferation of myofibroblasts and/or excessive production of ECM components. Such diseases in which pathogenic progressive fibrosis may be evident or imminent may be acute or chronic. Preferably progressive fibrosis is prevented or treated in chronic diseases or chronic fibroproliferative diseases.

Progressive Fibrosis in the Kidney

A number of diseases such as metabolic, anatomical, mechanical abnormalities, infections and toxic agents or autoimmune diseases can result in loss of kidney function. The most frequent examples of kidney related diseases in which progressive fibrosis are part of the syndrome are: diabetic nephropathy, hypertensive nephropathy, different types of glomerulonephritis, and certain tubulointerstitial disorders. Patients with diabetes and hypertension are at greatest risk and have a higher rate of renal problems than the normal population. Diabetic nephropathy accounts for 25-30% of new patients commencing renal replacement therapy worldwide. Antibiotics, analgesic drugs (aspirin, ibuprofen, acetaminophen etc.), chemotherapic agents, different drugs and various infections have all been also identified as progressive fibrosis inducing agents.

The different forms of renal diseases mimic a sustained injury leading to an excessive accumulation of ECM that may occur in virtually all type of chronic kidney failure. In diabetic nephropathy progressive fibrosis arises through activation of renal myofibroblasts to secrete certain proteins of the connective tissue, most commonly collagen types I, III, and IV and fibronectin and thereby remodel the ECM. Compounds used in diabetic nephropathy include renin-angiotensin-aldosterone system (RAAS) blockers, primarily ACE-inhibitors and ARBs, none of which directly aims at the overproliferation of ECM. A review of medication dosing in patients with chronic kidney disease is provided by Zuber K et al. the principles of which, and references cited therein, may be used as guidance for setting the dose of S1R agonists [Zuber K et al. *JAAPA.* 26(10), 19-25 (2013)].

Early phase diagnosis is preferred in treatment of the progressive fibrosis of the kidney. Present treatments focus on preventing and improving the symptoms and the progression of the disease itself. Oral administration in this case is preferred. Parenteral intravenous, intramuscular, intracutan or subcutan administration would be also an option, or direct infusion to target the kidney is also possible.

Progressive Fibrosis in the Lung

Infections, long-term exposure to pollutants or toxins (most commonly smoking), allergy, certain medications (e.g. chemotherapics), gastroesophageal reflux, autoimmun diseases (e.g. SLE) are all risk factors or potential causes of lung diseases characterized by inflammation and resulting in abnormal tissue repair. Scar forming and the thickening of the walls of the lungs lead to oxygen shortage and diseases identified under the generic term pulmonary fibrosis.

To the present knowledge scarring that occurs in progressive pulmonary fibrosis cannot be reversed, and no current treatment has proved effective in halting the progression of the disease. Some treatments including corticosteroids or immunsuppressive therapy may improve symptoms temporarily but their efficacy regarding fibrotic conditions is rather questionable with serious side effects.

Administration of the composition of the invention is preferably started at an early phase of the onset of disease. Inhalation represents a preferred option through systemic administration, if possible. Means for this type of administration, like powder inhalers, vaporizers, nebulizers, devices like oxygen mask, nasal cannula and metered dose inhalers are well-known in the art.

Progressive Fibrosis in the Gastrointestinal System

In chronic intestinal inflammatory conditions, inflammation is accompanied by a response where progressive fibrosis is an inevitable or very common component. In Crohn-disease, inflammation is typically transmural and so is the ensuing fibrostenotic response, whereas, in ulcerative colitis, inflammation and a progressive fibrotic response are virtually limited to the mucosal layer. Transmural inflammation and progressive fibrosis typically frequently result in symptomatic stenosis or stricture. Stellate cells are found not exclusively in liver, but also in the pancreas and human intestinal mucosa. Infiltrating immune cells and intestinal stellate cells release different cytokines and growth factors, such as TGFβ, which contribute to the remodeling of the ECM. Some cells of non-mesenchymal origin also undergo a process of transdifferentiation into mesenchymal cells to become efficient ECM-producing cells.

Although intestinal fibrosis is increasingly recognized as a problem, there is no accepted medication in the art to treat or hinder organ fibrosis of the GI system.

Preferably administration is carried out through the digestive tract. Examples of oral formulations include solid forms like pills, tablets, capsules, pastilles etc. Liquid forms include syrups, emulsions, suspensions, hydrogels, encapsulated forms, preferably in an extended release form.

Progressive Fibrosis in the Liver

A common symptom of fibroproliferative diseases of the liver (e.g. cirrhosis steatohepatis, infectious hepatitis, biliary diseases, storage diseases like hemochromatosis or Wilson's disease) may be the accumulation of excess connective tissue in the liver accompanying hepatocellular damage. Abnormal degradation of the ECM may also contribute to the progressive fibrosis of the liver. During the progression of fibrosis, activated stellate cells (or liver-specific pericytes) show features of smooth muscle-like cells, characterized by expression of a number of contractile filaments including α-SMA and myosin. As fibrosis advances, the activated stellate cells progressively impede portal blood flow mediated by pathways that allow interaction with the ECM. The end stage of chronic liver disease, without liver transplantation, frequently leads to death.

Early phase diagnosis is preferred also in treatment of the progressive fibrosis of the liver. Oral administration of compounds of the invention in this case is preferred. Parenteral intravenous, intramuscular, intracutan or subcutan) administration would be also an option.

Progressive Fibrosis in the Organs of the Urogenital System

The urogenital system can also be affected by diseases associated with progressive fibrosis when they are exposed to various infections (e.g. *chlamydia, candida* or herpes). Women are at risk of injuries to the organs of the reproductive system also during pregnancy, delivery or miscarriages. Irradiation associated fibrosis of the vagina or prostate could be a consequence of the anti-tumor treatment of the urogenital organs (e.g. ovarian or prostate cancer) Endometriosis is a severe progressive fibrotic disorder causing constant pain and infertility. Penile fibrosis is a possible cause of impotency in men.

Oral administration of compounds of the invention in this case is preferred and parenteral administration, like injection or infusion is also possible. Topical e.g. transmucosal administration may be possible if this may provide a better targeting of the drug. Topical formulae may include in this group of disorders ointment, vaginal or rectal suppositories, and rings etc, intrauterine devices.

Progressive Fibrosis in the Skin

Defective wound healing consists of two categories: in the case of chronic wounds (e.g. ulcerative lesions) the healing process is delayed or blocked, while in excessive wound healing (e.g. hypertrophic scars, keloids), the repair process is hyperactivated. Excessive wound healing occurs when ECM synthesis remains high, resulting in overproduction of collagen and other ECM components. This condition may arise from a failure of myofibroblasts to undergo apoptosis and results in hypertrophic scarring, leaving permanent and undesirable marks on the skin. In dermal keloids, the overproduction of collagen type I or type III extend beyond the boundaries of the original injury.

Most often progressive fibrosis related dermatological diseases or conditions are as follows: keloids of various origin (e.g. acne, piercing, chicken-pox), ulcus (e.g. diabetes derived), and various infectious diseases e.g. acne vulgaris, acne inversa). Treatment focuses on improving the symptoms and preventing the progression of fibrosis. Topical administration of the compound of the invention is preferred when treating a skin related symptom. Preventive treatment is contemplated when the patient is at risk of defective wound healing.

In dermal applications topical formulation of the medicament is preferred, among others ointments, topical creams and gels, dermal and transdermal patches and films, hydrogels, creams, lotions and sprays.

Progressive Fibrosis in the Eye

Most diseases that cause loss of vision are related to abnormal wound healing and angiogenesis. While among the most frequent causes are tissue ischemia or inflammation, it is usually, among others, the concomitant fibrosis that results in mechanical disruption of the visual axis [Friedlander, Martin. (2007) 117(3): 576-586].

Fibrosis, as a local response to injuries includes infiltration by inflammatory cells, neovascularization, altered vascular permeability, proliferation of fibroblasts and fibroblast-like cells, modification of the ECM, and, ultimately, some sort of resolution of the damaged tissue. Progressive fibrosis of the eye included fibrosis of the anterior segment of the eye which is not part of the central nervous system and posterior segments i.e. those which are part of the CNS, like retina wherein progressive fibrosis may be called gliosis. Preferably, in the present invention, fibrosis is present in the anterior segments. However, posterior segments i.e. those which are part of the CNS, like retina, have similar processes and in a broader aspect the invention covers those tissues as well.

In preferred embodiments the fibroproliferarive disease of the eye may be retinal fibrosis wherein a dysregulated accumulation of extracellular matrix (ECM) protein occurs. This can occur as the result of an aberrant wound-healing response, as in the case of post-surgical complications of proliferative vitreoretinopathy (PVR). Fibrosis has a role in other retinal diseases including diabetic retinopathy (DR) and age-related macular degeneration (AMD) as well, wherein neovascularization, a typical hallmark of late stage DR just as AMD, involves aberrant ECM assembly [Miller Charles G et al. Minireview: (2016) Fibronectin in retinal disease Experimental Biology and Medicine 242(1), 1-7]

A quite frequent eye disease, glaucoma, is characterized by neuropathy and loss of retinal ganglion cells, cupping and atrophy of the optic nerve head, and associated visual field loss. Primary open-angle (POAG) glaucoma, is a usual form wherein free aqueous humor (AH) outflow occurs, which due to clogging of trabecular meshwork (TM) channels, follows an abnormal route [Zhavoronkov, Alex et al. Profibrotic pathway activation in trabecular meshwork and lamina cribrosa is the main driving force of glaucoma Cell Cycle. 2016; 15(12): 1643-1652]. It is well known that fibrosis plays a role in the glaucoma progression and a number of therapeutic approaches have been studied in an attempt to combat fibrosis [see e.g. Hill, Lisa J, Neural Regen Res. 2016 Jun.; 11(6): 922-923.], however, mechanisms of fibrosis have been largely unknown.

The Trabecular Meshwork

The trabecular meshwork is an important regulator of intraocular pressure. The TM cells (TMC) display characteristic features of several different cell types, like those of endothelia, fibroblasts, smooth muscle and macrophages, owing to the multiple roles and two distinct environments where they operate to maintain intraocular pressure homeostasis [Stamer W. Daniel et al. The many faces of the trabecular meshwork cell Exp Eye Res. 2017 158 112-123.]. TMC make layers of beams, part of a fibrous basement membrane containing ECM cells. Damage and dysfunction of HTMC have clinical significance. For instance, physical changes to the TM include increased fibrosis, fibronectin accumulation, and expression of ECM cross-linking enzymes. This cytoskeletal reorganization and cell loss causes the TM to become rigid and stiff which may play role in several diseases, like glaucoma-related dysfunctions. Thus, fibrosis in TMC are good model for ocular fibrosis.

Concepts of Diagnosis

While it is known that many diseases are associated with progressive fibrosis the present invention is useful to prevent or inhibit the formation of excessive amount of ECM in different tissues and organs. While at present diagnosis of progressive fibrosis has its difficulties, diagnosis of such a condition is possible and advisable.

Inevitably, microscopic examination of tissue biopsies is one of the most reliable methods of diagnosing fibrotic tissue. Detection of the proliferation of mesangial cells (mesangial matrix expansion, (see e.g. Examples 8) and/or myofibroblasts, (e.g. as in Example 11, 13, 15) is clearly a possibility. Measurement of markers of progressive fibrosis like increased presence of Masson's trichrome (e.g. in Example 7, 12, 14) or Sirius red e.g. Example 10 positivity, increased expression of α-SMA (e.g. in Example 11, 13, 15) or determination of the amount of fibronectin (e.g. in Example 9) in the tissue is a further option (Example 5).

Several morphometry techniques are used to assess progressive interstitial fibrosis, including morphometry of slides stained with Masson's trichrome or Sirius Red which are specific for collagen types I and III under polarized light and immunohistochemistry method [Farris A B, *United States and Canadian Academy of Pathology Annual Meeting* (2012)]. The method is, however, invasive and inconvenient to the patient and quite often needs anesthesia. A skilled pathologist is needed for the assessment and the whole evaluation procedure is rather slow to use as routine clinical application. Moreover, invasive methods, while applicable in case of need, have their own risk [Díez J, Circ J. 72, A:A8-12 (2008)].

Thus, from the aspect of patient well-being and compliance non-invasive physical methods are preferred. There are certain functional non-invasive markers that are used as gold-standard values in the estimation of organ function (including kidney: glomerular filtration rate (GFR) and serum creatinine and urea nitrogen, proteinuria [KDIGO, 2013]; lung: spyrometry etc, liver: fibroscan. Pulmonary fibrosis can be diagnosed based on the Guidelines provided by the American Thoracic Society [Raghu et al. Am J Respir Crit Care Med 183, 788-824 (2011)]. Progressive liver fibrosis can be diagnosed by serum markers (hepatic myofibroblast specific single chain antibody C1-3 was conjugate and imaging techniques that are in a research-phase yet [Hill S, Thesis (2012)].

These markers can predict the deterioration of the organ function, but they are not always specific enough for the progressive fibrotic process. Furthermore at present all these markers are expensive and slow to perform, therefore the techniques are expected to improve in the future and new markers will be probably also discovered.

As to biomarkers of the fibrosis in the eye the research is underway. Cynthia Yu-Wai-Man et al. [Cynthia Yu-Wai-Man Personalized Medicine in Ocular Fibrosis: Myth or Future Biomarkers. Adv Wound Care (New Rochelle). 2016 Sep. 1; 5(9): 390-402.] list a number of new biomarkers which are under validation. However, such biomarkers can be used in the present invention to diagnose risk of scarring and to decide on as well as to carry out the antifibrotic treatment regimen to each individual patient.

However, progressive fibrosis in the eye, albeit in a later stage than diagnosis by biomarkers, can be established by the comprehensive ocular examination including the measurement of ocular pressure as well.

As to diagnosis of glaucoma, a fibroproliferative eye disease the treatment of which is preferred according to the invention, preferably the following factors should be examined:

the inner eye pressure (preferably by tonometry), the examination, eg. shape and color of the optic nerve (preferably by ophthalmoscopy or dilated eye exam or computer measurement), the complete field of vision (preferably by perimetry or visual field test), the angle in the eye where the iris meets the cornea (preferably by gonioscopy), the thickness of the cornea (preferably by pachymetry).

By this method e.g. open or closed angle glaucoma, and preferably glaucoma of the anterior or posterior eye tissues can be diagnosed.

Below the invention is illustrated through specific examples and exemplary embodiments which, however, do not limit the scope of the invention.

EXAMPLES

Methods
Compounds
fluvoxamine (fluvoxamine maleate, Sigma Aldrich, St. Louis, Mo., USA), PRE-084 (2-morpholin-4-dylethyl 1-phenylcyclohexane-1-carboxylate Sigma Aldrich, St. Louis, Mo., USA), SA4503 (1-[2-(3,4-Dimethoxyphenyl) ethyl]-4-(3-phenylpropyl)piperazine; Tocris Bioscience, Bristol, UK); NE100 (N-dipropyl-2-[4-methoxy-3-(2-phenylethoxy)-phenyl]-ethylamine monohydrochloride, Tocris Bioscience, Bristol, UK)

Cell Lines

NRK49F rat kidney interstitial fibroblast cell lines (American Type Culture Collection, Manassas, Va., USA) were cultured in Dulbecco's modified Eagle's medium (Gibco, Life Technologies, Carlsbad, Calif., USA) supplemented with 10% fetal bovine serum (FBS) (Gibco, Life Technologies, Carlsbad, Calif., USA) and 1% Antibiotic-Antimycotic Solution (Sigma-Aldrich Co., St. Louis, Mo., USA) at 37° C. and 5% $CO_2$.

Cell Viability and Proliferation Assay

To test the possible cytotoxic effect of the said compounds cell viability was determined in 96-well plate by (3-(4,5-dimethylthiazol-2-yl)-2,5-diphenyltetrazolium bromide) MTT assay after 24-hours treatment with the said S1R compounds (Roche Diagnostics, Mannheim, Germany). Cell viability was also assessed by trypan blue exclusion. Cells were detached with trypsin-EDTA and re-suspended in medium diluted 1:1 with trypan blue solution (Sigma Aldrich, Budapest, Hungary). Live cells from triplicate wells were counted in a Burker chamber.

To investigate the effect of S1R agonists (fluvoxamine, PRE084, SA4503) on PDGFB induced proliferation renal fibroblasts cells were starved in 0.01% FBS for 24 hours then trypsinized and seeded in 6-well plates at a density of $5 \times 10^5$ cells/well. After plating, cells were treated with human recombinant rPDGFBB; (10 ng/mL, R&D Systems, Minneapolis, Minn., USA). A group of cells was treated with rPDGFBB and fluvoxamine (1, 5 and 10 μM/L; Cell Signaling Technology Inc., Danvers, Mass., USA). Control cells were treated with solvents (4 mM HCl, Sigma-Aldrich Co., St. Louis, Mo., USA) alone. Subsequently cells were incubated for 24 hours at 37° C. then cell proliferation assay (MTT) was performed.

PicroSyrius Red Stain to Measure Collagen Production

To investigate the deposition of fibrillar collagen Sirius Red staining was performed. 48 hours after the treatment with TGF-β and said compounds the NRK-49F cells were incubated for 10 minutes with Kahle fixative solution. 0.1% Sirius Red (Direct Red 80, Sigma-Aldrich) in 1.2% picric acid was added for each well and plates were incubated for 30 minutes at RT. The unconnected dye molecules were washed with distilled water. The bound Sirius Red dye was eluated with 0.1 M NaOH solution, absorbance was recorded at 540 nm in a Hidex Chameleon Microplate Reader (Triathler, Plate Chameleion, 300SL Lablogic Systems, Inc., Brandon, Fla., USA) used MikroWin program. Vehicle treated cells served as controls.

Collagen I-III PCR

Total RNA was isolated from NRK49F cells by RNeasy Micro RNA isolations kit (Qiagen GmbH, Hilden, Germany). 100 ng RNA was reverse-transcribed using Super-Script III RNase H— (Gibco, Life Technologies, Carlsbad, Calif., USA) to generate first-strand cDNA. The mRNA expressions of collagen I, collagen III and glyceraldehyde-3-phosphate dehydrogenase (GAPDH) were determined by real-time RT-PCR using Light Cycler 480 SYBR Green 1 Master on a Light Cycler system (Roche Diagnostics, Mannheim, Germany). The reaction mix contained 10 μmol/μl of each PCR primers (Table 1; Invitrogen, Life Technologies, Carlsbad, Calif., USA), 10 μl of Light Cycler 480 SYBR Green 1 Master enzyme mix (Roche Diagnostics, Mannheim, Germany) and 1 μl of cDNA sample. The conditions of the PCRs were as follows: 1 cycle at 95° C. for 5 minutes, followed by 60 cycles under the appropriate PCR conditions. Quantification was performed with the second-derivative method by monitoring the cycle number at which the fluorescent sign could be distinguished from the background. Results were analyzed with Light Cycler 480 software version 1.5.0.39 (Roche Diagnostics, Mannheim, Germany). The mRNA expression of each gene was determined by comparison with GAPDH as internal control from the same sample.

kidneys were removed, weighed and a section fixed in formalin (4%, pH=7.4) for histology and the remained immediately snap-frozen for further investigations.

Mice Model of Unilateral Ureteral Obstruction (UUO) Induced Renal Fibrosis

After general anesthesia animals were placed on a thermo controlled table to maintain rectal temperature at 37±1° C.). After standard midline laparotomy the bowel was gently displaced from the abdomen and covered with sterile saline

TABLE 1

Nucleotide sequence of specific primer pairs applied for the real time detection of the examined genes and conditions of the PCR reactions.

| Gene | Primer sequences | PCR conditions |
| --- | --- | --- |
| Rat collagen I | F: 5'-AGCTCAGGGGCGAAGGCAACAGTC-3' (SEQ ID NO: 1)<br>R: 5'-CAGGCGGGAGGTCTTGGT-3' (SEQ ID NO: 2) | 95° C.-5 sec<br>59° C.-7 sec<br>72° C.-7 sec |
| Rat collagen III | F: 5'-AGGCGGTGCGGGTGCTGAT-3' (SEQ ID NO: 3)<br>R: 5'-GGGCCAGGGGGACCAATAGGA-3' (SEQ ID NO: 4) | 95° C.-5 sec<br>59° C.-7 sec<br>72° C.-7 sec |
| Rat GAPDH | F: 5'-GTCACGGCATGGACTGTG-3' (SEQ ID NO: 5)<br>R: 5'-CACCACCATGGAGAAGGCTG-3' (SEQ ID NO: 6) | 95° C.-5 sec<br>60° C.-5 sec<br>72° C.-10 sec |

In Vivo Models of Fibrosis

Animals

The institutional committee on animal welfare approved all experiments. Experiments were performed on Male Wistar rats weighing 205±15 g (Toxi-Coop Toxicological Research Center, Dunakeszi, Hungary) or 7-8 week old male C57BL/6 mice (WT; Charles River Laboratories, Sulzfeld, Germany). Animals were housed in a temperature-controlled (22±1° C.) room with alternating light and dark cycles and had free access to standard rat chow and water.

During surgical procedures or at animal harvest general anesthesia was performed by an i.p. injection of ketamine (75 mg/bwkg) and xylazine (10 mg/bwkg). (Richter Ltd., Budapest, Hungary).

Rat Model of Streptozotocin (STZ) Induced Diabetic Nephropathy

All substances were purchased from Sigma-Aldrich Ltd. (Budapest, Hungary). Diabetes was induced in male Wistar rats by 65 mg/bwkg streptozotocin (STZ) i.v. (dissolved in 0.1 M citrate buffer; pH 4.5). Animals were considered diabetic if blood glucose concentrations increased to 15 mmol/L within 72 h after STZ injection and remained elevated. Animals were randomly divided into groups (n=10-12/group) and received by per os (i) fluvoxamine (20 mg/bwkg/day) for 7 weeks; (ii) fluvoxamine (20 mg/bwkg/day) for 2 weeks from the 5$^{th}$ week of diabetes, (iii) fluvoxamine (2 mg/bwkg/day) for 2 weeks from the 5$^{th}$ week of diabetes; or (iv) vehicle (isotonic saline). Additional groups were also treated per os with NE100, a specific inhibitor (antagonist) of S1R (v) fluvoxamine+NE100 (20 mg/bwkg/day+1 mg/bwkg/day) for two weeks, (vi) fluvoxamine+NE100 (2 mg/bwkg/day+1 mg/bwkg/day) for two weeks. Non-diabetic age-matched control animals were injected with citrate buffer and sacrificed after 7 weeks (n=8-10/group).

Before and during and at the end of treatment period rats were placed into metabolic cages to collect 24-hour urinary samples. After 2 weeks of treatment all rats were anesthesized, blood and urinary samples were collected and the soaked sterile gauze. Left ureter was isolated by blunt dissection and completely ligated using fine suture material (6/0 Safil, B. Braun Aesculap, Panama, USA). The bowel was then laid back and the muscle and skin were closed with 4-0 nylon sutures. Mice were treated with fluvoxamine (20 mg/bwkg/day, i.p.) or fluvoxamine+NE100 (1 mg/bwkg/day, i.p.). Left kidneys of the mice were surgically removed on the 7th day (n=6) after the onset of UUO. As surgical controls, animals (n=6) underwent identical surgical procedure without occlusion of left ureter. Kidney segments were immediately used for molecular biological measurements or frozen in liquid nitrogen and fixed in formalin (4%, pH=7.4).

Rat Model of Bleomycin Induced Pulmonary Fibrosis

For the induction of pulmonary fibrosis male Wistar rats were anesthetized. Bleomycin (5 mg/bwkg in a 300 µl solution of isotonic saline) or 300 µl isotonic saline was administered into the trachea using a 30G needle.

Animals were randomly divided into 4 groups of 6 rats each as follows (i)—control group was sham operated, received isotonic saline per os daily for 3 weeks, (ii) vehicle treated group: received isotonic saline per os daily for 3 weeks after the induction of lung fibrosis, (iii) fluvoxamine treated group: received fluvoxamine (20 mg/bwkg/day per os for 3 weeks after the induction of lung fibrosis), (iv) fluvoxamine+NE100 treated group: received fluvoxamine (20 mg/bwkg/day; per os) and 1 mg/bwkg/day NE100 (i.p. for 3 weeks after the induction of lung fibrosis.

For the induction of pulmonary fibrosis rats were anesthetized and bleomycin (5 mg/bwkg in a 300 µl solution of isotonic saline) or 300 µl isotonic saline was administered intratracheally using a 30G needle. Animals were sacrificed 21 days after the induction of pulmonary fibrosis.

Measurement of Metabolic and Renal Parameters

Serum metabolic (glucose, fructoseamine, total and HDL-cholesterol, triglycerides) and renal functional parameters from rat serum (sodium, potassium, creatinine, BUN, GFR and proteinuria) were determined with commercially available kits on a Hitachi 912 photometric chemistry analyzer.

Random urine and 24-hour urine samples were also measured. Urinary protein to creatinine ratio was also calculated.

Histological Analysis

PAS Staining

Kidney was fixed in 10% formalin, paraffin embedded, 5 µm wide sections were taken and stained with periodic acid-Schiff (PAS) for determination of glomerular matrix expansion, vascular hyalinosis and tubulointerstitial lesions. Briefly, glomerular hypertrophy was determined by measuring the glomerular tuft area of 50 glomerular cross-sections excluding incomplete glomeruli along the sample edge. Hyaline was determined by assessment of PAS-positive and nucleus-free areas within the arterioles. Arteriolar hyalinosis was defined by the average of hyalinized quarters of arterioles. The presence of Armanni-Ebstein lesions was also evaluated. The analysis was performed on a double blinded fashion with computer-assisted morphometry using AxioVision 4.8 software on a Zeiss Axiolmager A1 light-microscope.

Fibronectin Staining

Heat-induced epitope retrieval was performed by boiling the paraffine-embedded tissue sections in citrate buffer (pH 6, HISTOLS, Citrate Buffer, Histopathology Ltd). Slides were peroxidase blocked (HISTOLS Peroxidase Blocking, Histopathology Ltd), and non-specific attachments were inhibited with protein solution (HISTOLS BBPS, Histopathology Ltd). Sections were incubated with policlonal antibody against fibronectin (1:500, Abcam, USA) and peroxidase labelled anti-rabbit antibody (HISTOLS-R, Detection System, Histopathology Ltd). Fibronectin was visualised with HISTOLS-Resistant AEC Chromogen/Substrate System, (Histopathology Ltd.), counterstained with haematoxylin and eosin and mounted with permanent mounting medium.

Masson's Trichrome Staining

To investigate the amount of collagen fibers the formalin-fixed and paraffin embedded tissue samples were dewaxed and cut into 4-10 µm slices. Slides were immersed in Weigert's hematoxylin (Sigma-Aldrich Co., St. Louis, Mo., USA) then were stained serially with acid fuschin, phosphomolybdic acid and methyl blue. The color was fixed in 1% acetic acid. Then the slides were dehydrated using increasingly higher concentration of alcohol, fixed in toluene, mounted in Permount (Fisher Scientific Inc., Waltham, Mass., USA.) and air-dried overnight before observation and photography. The nuclei of the cells appear as blue-black, the collagen fibers stained blue, the cytoplasm is red.

The stained sections were viewed and photographed with Pannoramic 250 Flash and Pannoramic Viewer 1.15.2 (3D HISTECH Ltd. Budapest, Hungary) Adobe Photoshop 13.0 and Scion Image for Windows software were used for the analysis. The blue staining of fibrotic tissue was marked using the color-recognizer option of Adobe Photoshop software. The number of blue stained pixels (i.e. the area of the fibrotic tissue) was divided by the number of pixels in the whole section, thus giving the ratio of fibrotic tissue to all tissue. Finally these ratios were statistically analyzed in all of the treatment groups.

Protein Isolation and Western Blotting

Tissue samples were lysed in buffer containing leupeptin, aprotinin, Triton X-100, Tris-HCl, Ethylene glycol-bis(2-aminoethylether),N,N,N',N'-tetraacetic-acid, NaF, Phenylmethylsulphonylfluoride and Na-orthovanadate (each substance were purchased from Sigma-Aldrich Co., St. Louis, Mo., USA) and centrifuged to pellet nuclei and large cellular fragments. Protein concentration of the supernatants was determined by Bradford assay (Bio-Rad Laboratories, Hercules, Calif., USA). Ten micrograms were separated by 10% SDS-PAGE at 120 V (~40 mA, 90 min) (Penguin™ Dual-Gel Water Cooled Systems, Owl, N.H., USA). Pre-stained protein mixture (BenchMark™, Gibco/BRL, Eggenstein, Germany) was used as marker of molecular mass. The separated proteins were transferred into nitrocellulose membrane (GE Haelthcare, Little Chalfont, UK) at 70 V (~220 mA, 90 min) (MiniTank™ electroblotter, Owl, N.H., USA). Non-specific binding sites were blocked in 5% non-fat dry milk containing blot solution. Membranes were incubated with monoclonal antibody specific to mouse α-SMA (Sigma-Aldrich Co., St. Louis, Mo., USA) diluted to 1:1000. Blots were washed and incubated (30 min, room temperature) with peroxidase-conjugated goat anti-rabbit IgG secondary antibody (Sigma-Aldrich Co.) diluted to 1:10000. Equal protein loading to the gel was confirmed by staining with a goat polyclonal IgG antibody raised against the carboxy (C-11) terminus of the β-actin (Santa Cruz Biotechnology Inc.). Immunoreactive bands were visualized using enhanced chemiluminescence Western blotting detection protocol (AP Biotech, Buckinghamshire, UK). Bands were analyzed with Quantity One software version 4.6.9. (Bio-Rad). Ponceau staining was used as a loading control and an internal control was used as well.

Fluorescent Immunohistochemistry

Frozen kidney sections were embedded in Shandon cryomatrix (Thermo Fisher Scientific) and cut to 5-7 µm slides with a cryostat. Samples were incubated for one hour with the specific mouse α-SMA (1:2000, Sigma-Aldrich Co., St. Louis, Mo., USA) or S1R (1:100, Sigma-Aldrich Co., St. Louis, Mo., USA) antibody. After repeated washing slides were incubated with goat anti-mouse Alexa Fluor 488 conjugate and counterstained with Hoechst 33342 (Sigma-Aldrich Ltd.) to visualize nuclei. Appropriate controls were performed omitting the primary antibody to assure the specificity and to avoid autofluorescence. Sections were analyzed with a Zeiss LSM 510 Meta confocal laser scanning microscope with objectives of 20× and 63× magnification.

Statistical Analysis

Data were analyzed using GraphPad Prism software (GraphPad Software Inc., La Jolla, Calif., USA). After testing the normality with Kolmogorov-Smirnov test, numerical datasets from all experiments were analyzed using the Mann-Whitney U-test for two group's comparison and Kruskal-Wallis test when there were 3 or more groups. P values less than 0.05 were considered to indicate statistically significant differences. Values for all measurements were expressed as mean+−SEM.

Experiments with Human Trabecular Meshwork-5 (HTM-5) Cells

Cell Cultures

Human trabecular meshwork-5 (HTM-5) were cultured in DMEM containing 25 mM glucose (Thermo Fisher Scientific, Waltham, Mass., USA) supplemented with 10% FBS, 1% penicillin/streptomycin and 1% L-glutamine (Sigma-Aldrich St. Luis, Mo., USA). Cells were incubated at 37° C. in a humidified atmosphere of 5% $CO_2$ and 95% air.

Methyl-Thiazoletetrazolium (MTT) Cell Proliferation Assay

HTM-5 cells were plated in serum free fresh medium in 96 well plates at a density of 40 000 cells/well and treated with 20 ng/mL of platelet-derived growth factor (PDGF; R&D Systems, Minneapolis, Minn., USA), 10-15 µM fluvoxamine (PDGF+FLU; Sigma-Aldrich, St. Luis, Mo., USA), 5-15 µM SA-4503 (PDGF+SA; Tocris Bioscience, Bristol, UK), and with 5-15 µM PRE-087 (PDGF+PRE;

Sigma-Aldrich, St. Luis, Mo., USA) for 24 h. Control cells were treated with vehicle (HCl) alone (n=6 wells/group). After the treatment period cells were incubated with methylthiazoletetrazolium (MTT) for 4 h followed by solubilisation in DMSO-ethanol (1:1). The formation of water-insoluble formazan was determined by measuring optical density at 570 nm in a Plate CHAMELEON™ V Fluorometer-Luminometer-Photom reader (Hidex, Turku, Finland).

Immunocytochemistry

Morphological changes/cytoskeleton rearrangements of HTM-5 cells caused by PDGF was visualised by immunostaining of F-actin. Cells were plated at a density of 200 000 cells/well on 0.1% gelatine coated tissue culture chambers in serum-free media. Cells were treated with PDGF (20 ng/mL) or FLU (10 µM) for 24 h, then cells were washed with PBS, fixed in 4% formalin, washed again, permeabilised with Triton X-100 (Sigma-Aldrich, St. Luis, Mo., USA) and blocked with 5% BSA (Sigma-Aldrich, St. Luis, Mo., USA). Repeated washes with PBS were followed by staining with phalloidin-Alexa-Fluor 546 (1:40; Invitrogen, Carlsbad, Calif., USA) for F-actin and with Hoechst (Sigma-Aldrich, St. Luis, Mo., USA) for DNA. After PBS washes, coverslips were mounted onto slides using ProLong Anti-Fade (Life Technologies, Waltham, Mass., USA). Images were obtained at 10× and 60× magnification on Nikon Ti2 fluorescent microscope.

Reverse Transcription Polymerase Chain Reaction (RT-PCR)

Total RNA was extracted using the RT050 Total RNA isolation Mini Kit (Geneaid Biotech, New Taipei City, Taiwan). The quality and quantity of isolated RNA was measured on a NanoDrop ND-1000 spectrophotometer (Baylor College of Medicine, Houston, Tex., USA). One hundred fifty nanograms each of FN1, COL1A1 and MMP2 mRNA from HTM-5 cells were reverse-transcribed using a First Strand cDNA Synthesis Kit for RT-PCR (Thermo Fisher Scientific, Waltham, Mass., USA). The expression of the mRNA was determined in triplicate with 1 µL cDNA samples obtained by qPCR using 10 µL SYBR Green I Master enzyme mix (Roche Diagnostics, Mannheim, Germany) and 10 pmol µL-1 of each specific primer (Invitrogen, Carlsbad, Calif., USA), following sequences designed by Lasergene PrimerSelect software version 7.1.0 (DNASTAR, Medison, Wis., USA) based on nucleotide sequences from National Center for Biotechnology Information's nucleotide database. Results were analysed by LightCycler 480 software version 1.5.0 (Roche Diagnostics, Indianapolis, Ind., USA). The mRNA expression of interest was normalised against mRNA expression of 18S ribosomal RNA (RN18S) from the same samples as internal control.

Statistical Analysis

Statistical analyses were performed using GraphPad Prism software version 6.01 (GraphPad Software Inc., San Diego, Calif., USA). To test if the values were from a Gaussian distribution, a Kolmogorov-Smirnov normality test was performed. Data were analysed by one-way ANOVA followed by Bonferroni's multiple-comparison post hoc test for all parametrical comparisons, or in the case of non-parametric data, by Kruskal-Wallis ANOVA on ranks. Significance was set a priori at $P<0.05$, corrected for multiple comparisons.

Example 1—S1R is Expressed in Various In Vitro, In Vivo and Human Samples

Fluorescent immunohistochemistry confirmed the presence of SIR in various models (see also the chapter "Fluorescent immunohistochemistry"). In vitro in myofibroblasts (1A) SIR was localized in the whole cytoplasm with a predominant enrichment in the endoplasmic reticulum. In in vivo samples SIR showed a perinuclear staining pattern of proximal tubules, however it was also visible in the cytoplasm (1B). Immunhistochemistry of the total kidney of diabetic rats (1C) revealed that SIR is not expressed in renal glomeruli. In renal biopsies of patients diagnosed with obstructive uropathy (1D) SIR staining and patchy co-localization with α-smooth muscle actin (αSMA) indicates that SIR is expressed in the myofibroblasts also in humans.

Figure 1A:
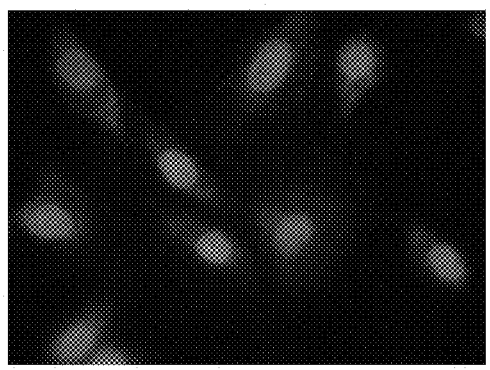
FIGS. 1A-D. Sigma-1 receptor (S1R) expression in various models: in vitro in myofibroblasts (FIG. 1A); in vivo in proximal tubules (FIG. 1B) and whole kidney samples (FIG. 1C) of diabetic rats and also in (FIG. 1D) renal biopsies of patients diagnosed with obstructive uropathy. SIR is also co-localized with α-smooth muscle actin (αSMA) (FIG. 1D). SIR was stained with red (Alexa Fluor 543 on FIGS. 1A-D), while αSMA were stained with green (Alexa Fluor 488 on FIGS. 1A-D). Nucleus is stained blue with Hoechst. (Pictures were evaluated Zeiss Axiovert, confocal laser-scanning microscope, 40×, 63×, 100× magnification, respectively).
Figure 1B:
Figure 1C:
Figure 1D:
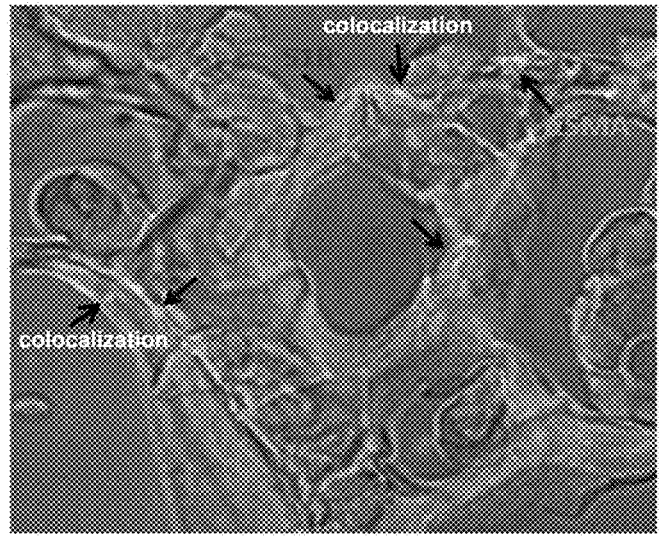
Figure 2A:
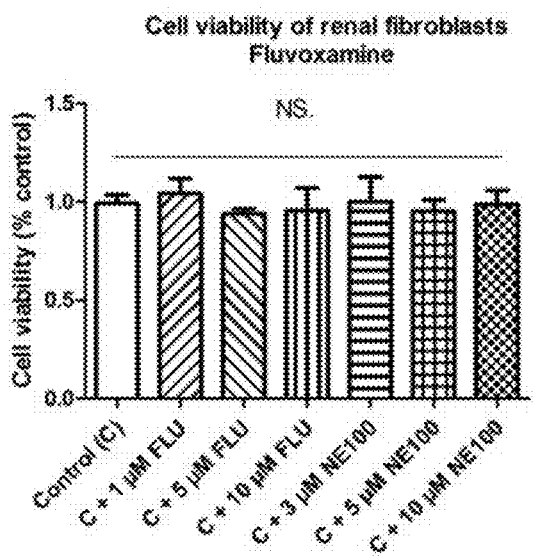
FIGS. 2A-C. Sigma-1 receptor (S1R) compounds [fluvoxamine (FIG. 2A), NE-100 (FIG. 2A) SA-4503 (FIG. 2B), PRE-084 (FIG. 2C)] are not cytotoxic in myofibroblasts. After 24-hours treatment with the S1R compounds in different concentrations (1, 3, 5, 10, 20 μM/L), cell viability was measured by (3-(4,5-dimethylthiazol-2-yl)-2,5-diphenyltetrazolium bromide) MTT assay on 96-well plate ($4 \times 10^3$ cells/well). (Bars represent mean±SEM)
Figure 2B:
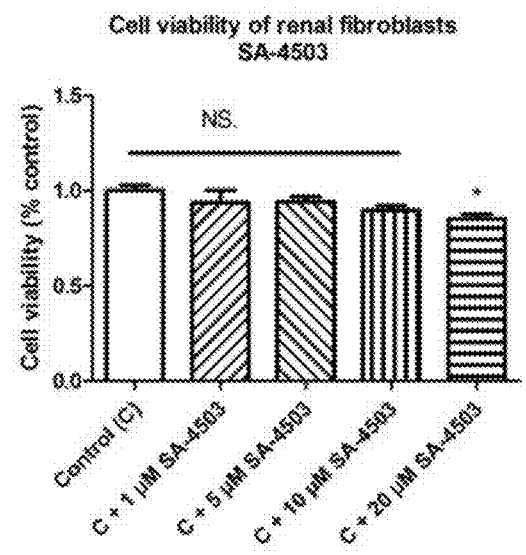
Figure 2C:
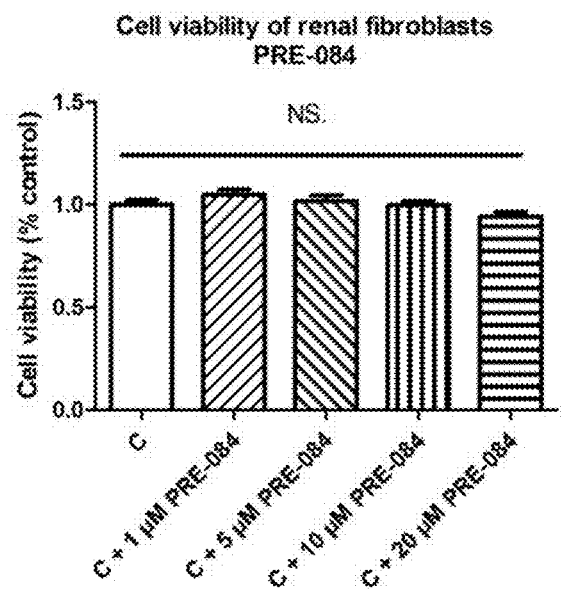

Example 2—S1R Agonist Compounds (Fluvoxamine, SA-4503, PRE-084) are not Cytotoxic in Myomyofibroblasts None of the selective SIR agonists (fluvoxamine (FIG. 2A), SA-4503 (FIG. 2B) or PRE-084 (FIG. 2C)) inhibited cell viability of NRK49F cells, which confirms that applied concentrations of the said SIR compounds are not cytotoxic in myofibroblasts in the commonly used doses (1-10 µM) and therefore they can be administered in in vitro studies (see also the chapter "In vitro experiments on myofibroblasts—MTT assay").

Figure 3A:
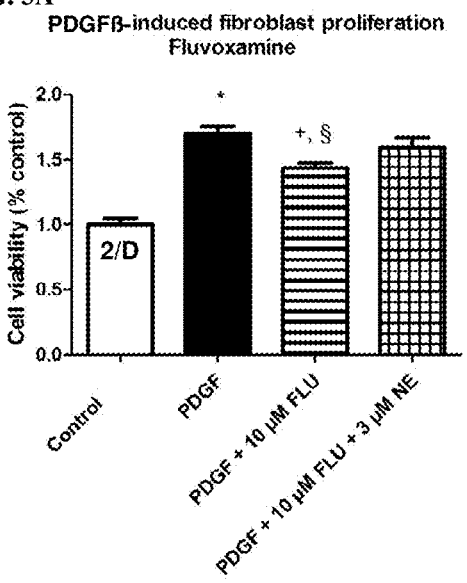
FIGS. 3A-C. Sigma-1 receptor (S1R) agonist compounds [fluvoxamine (FIG. 3A), fluvoxamine+NE-100 (FIG. 3A), SA-4503 (FIG. 3B), PRE-084 (FIG. 3C)] inhibits PDGFB-induced cell proliferation. Myofibroblast proliferation was induced by 10 ng/mL PDGFB in 6-well plates ($6 \times 10^6$ cells/well). To investigate the effect of S1R agonists parallel to PDGF-induction a group of cells was treated with the said compounds in different concentrations (1, 3, 5, 10, 20 μM/L). Subsequently cells were incubated for 24 hours at 37° C. then cell proliferation assay (MTT) was performed. Solvent treated cells served as controls. (Bars represent mean±SEM)
Figure 3B:
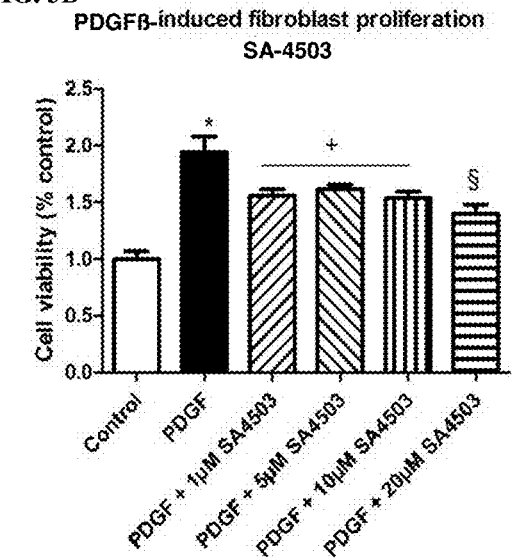
Figure 3C:
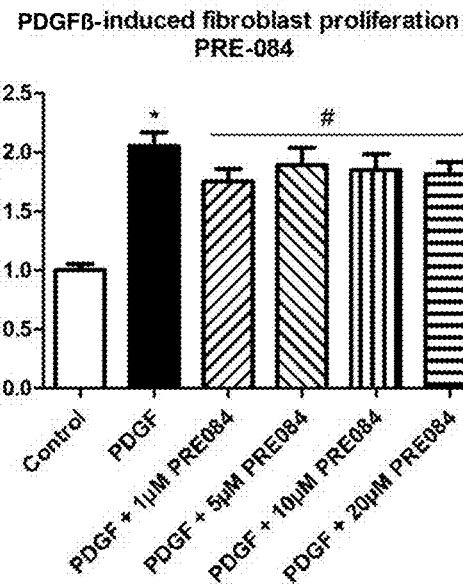

Example 3—S1R Agonist Compounds (Fluvoxamine, SA-4503, PRE-084) Decreases PDGF Induced Cell-Proliferation PDGF treatment of myofibroblasts for 24 hours resulted in significantly increased cell proliferation compared to controls (FIG. 3; see also the chapter "In vitro experiments on myofibroblasts—MTT assay"). Pretreatment with different concentrations of the said SIR agonists (fluvoxamine (FIG. 3A), SA-4503 (FIG. 3B) or PRE-084 (FIG. 3C)) significantly decreased PDGF-induced myofibroblast proliferation. Co-incubation with the S1R antagonist NE-100 (3 µM) suspended the effect of fluvoxamine (10 µM), which suggests that the anti-proliferative effect is SIR mediated.

Figure 4A:
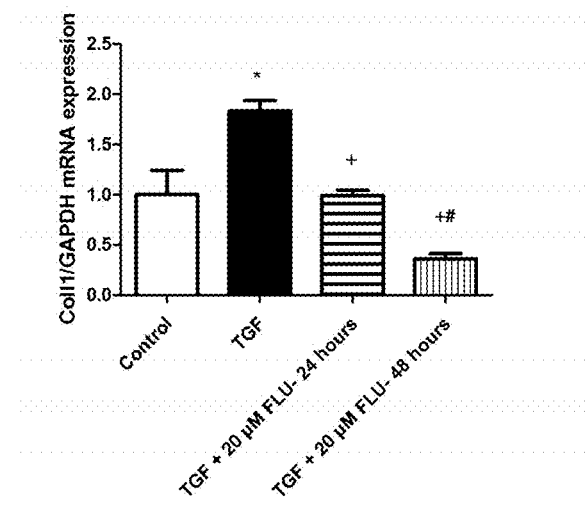
FIGS. 4A-B. Sigma-1 receptor (S1R) agonist compound fluvoxamine minimizes TGFβ-induced collagen-1 (FIG. 4A) and collagen-3 (FIG. 4B) production of myofibroblasts on a time-dependent manner. Collagen-1 and collagen-3 production was induced by 0.5 nM TGF-β in 6-well plates ($6 \times 10^6$ cells/well). To investigate the effect of S1R agonist fluvoxamine a group of cells was treated with 20 μM/L fluvoxamine parallel to TGFβ-induction. Subsequently cells were incubated for 48 hours at 37° C. then quantitative RT-PCR was performed. Solvent treated cells served as controls. (Bars represent mean±SEM)
Figure 4B:
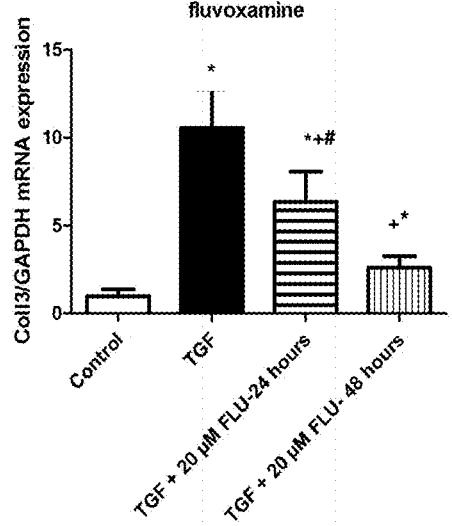

Example 4—S1R Agonist Compound Fluvoxamine Minimizes TGFβ-Induced Collagen 1 and Collagen 3 Production of Myofibroblasts in a Time-Dependent Manner NRK49F myofibroblast cells were treated with 50 nM TGFβ to induce collagen production. (FIG. 4; the model used is described in the chapter "In vitro experiments on myofibroblasts—RT-PCR"). 48 hours of treatment resulted in a significant production of ECM components collagen-1 (FIG. 4A), and collagen-3 (FIG. 4B). Compared to TGFβ treated cells fluvoxamine treatment remarkably diminished mRNA expression of the said collagens already as early as by 24 hours. By 48 hours collagen production of fluvoxamine treated cells returned to the level of normal controls.

Figure 5A:
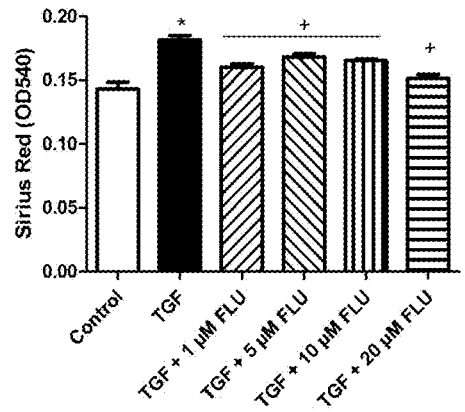
FIGS. 5A-C. Sigma-1 receptor (S1R) agonist compounds [fluvoxamine (FIG. 5A), SA-4503 (FIG. 5B), PRE-084 (FIG. 5C)] inhibit TGFβ-induced extracellular matrix (ECM) production. In 6-well plates of NRK49F myofibroblasts ($6 \times 10^6$ cells/well) TGF-β (1 nM) induced production of fibrillar components of the extracellular matrix was measured by Sirius Red staining. To investigate the effect of S1R agonist compounds a group of cells was treated for 48 hours with the various S1R agonists. Solvent treated cells served as controls. (Bars represent mean±SEM)
Figure 5B:
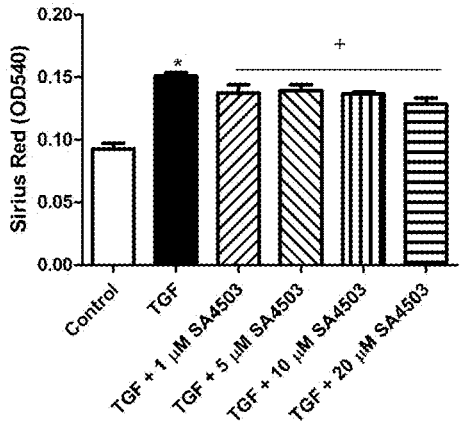
Figure 5C:
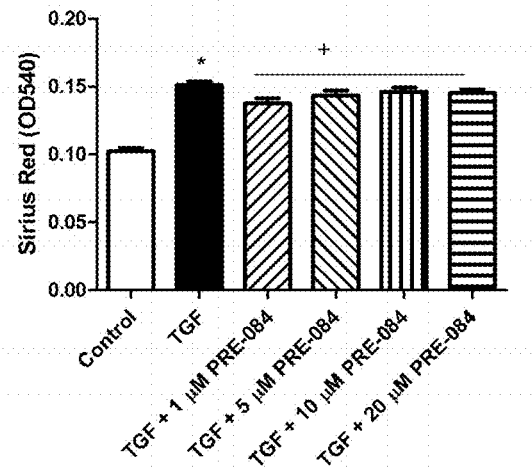

Example 5—Sigma-1 Receptor (S1R) Agonist Compounds (Fluvoxamine, SA-4503, PRE-084) Inhibit TGFβ-Induced Extracellular Matrix (ECM) Production 24 hours of TGFβ induction led to significant ECM production of NRK49F myofibroblasts compared to controls (FIG. 5; the model used is described in the chapter "In vitro experiments on myofibroblasts—Sirius Red staining"). All the applied concentrations (even the smallest 1 μM) of the said S1R agonist compounds (fluvoxamine (FIG. 5A), SA-4503 (FIG. 5B) or PRE-084 (FIG. 5C)) significantly inhibited TGFβ-induced ECM production.

Example 6—S1R Agonist Fluvoxamine Improves Diabetes Induced Impairment in Renal Function Renal parameters of control, diabetic and treated diabetic rats (Table 2-3) were measured. The model used is described in the chapter "Rat model of streptozotocin induced diabetic nephropathy". Diabetes induced severe renal impairment with increased serum creatinine and blood urea nitrogen values. Fractional sodium excretion (FeNa) was increased, significant albuminuria was present and the glomerular filtration rate (GFR) was decreased, all indicating the development of diabetic nephropathy. Fluvoxamine treatment, specifically the long-term (7-weeks) treatment remarkably improved renal function, prevented GFR decline. This beneficial effect was diminished by co-administration of the specific S1R antagonist NE-100 (Table 3), which confirms that any non-specific effect on a receptor other than S1R could be excluded. These data prove that S1R agonists are renoprotective and the treatments improve those gold standard markers of renal function that are used also in human clinical routine for the assessment of kidney failure.

Table 3 shows renal function parameters of Streptozotocin-(65 mg/bwkg iv.) induced type 1 diabetic rats treated per os with (D): vehicle (isotonic saline); (D+FLU): fluvoxamine (20 mg/bwkg/day) for 2 weeks from the $5^{th}$ week of diabetes,) or (D+FLU2): fluvoxamine (2 mg/bwkg/day) for 2 weeks from the $5^{th}$ week of diabetes. Additional groups were also treated per os with NE-100, a specific antagonist of S1R; (D+FLU+NE-100): fluvoxamine+NE-100 (20 mg/bwkg/day+1 mg/bwkg/day) for two weeks or D+FLU2+NE-100):fluvoxamine+NE-100 (2 mg/bwkg/day+1 mg/bwkg/day) for two weeks from the $5^{th}$ week of diabetes. GFR-glomerular filtration rate, FeNa: fractional sodium excretion. § $p<0.05$ vs. Diabetes; $p0.05 vs. D+FLU; # $p \leq 0.05$ vs.D+FLU2; (n=8-10 group, Mean±SEM).

Figure 6A:
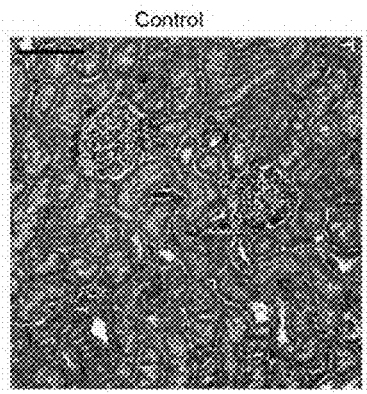
FIGS. 6A-H. Sigma-1 receptor (S1R) agonist fluvoxamine decreases diabetes induced tubulointerstitial fibrosis in the kidney of diabetic rats
Figure 6B:
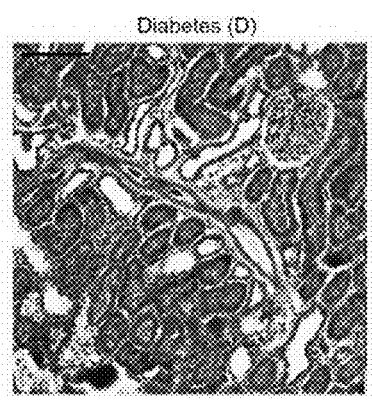
Figure 6C:
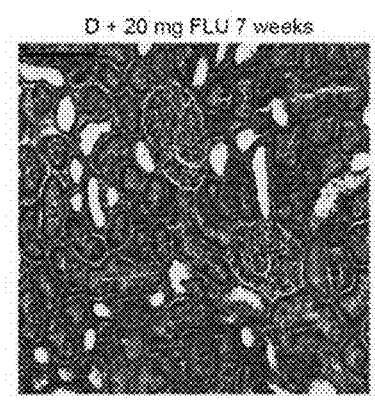
Figure 6D:
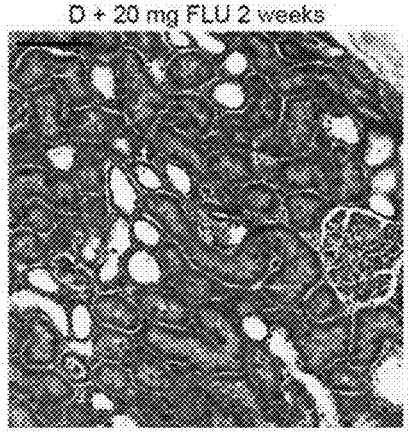
Figure 6E:
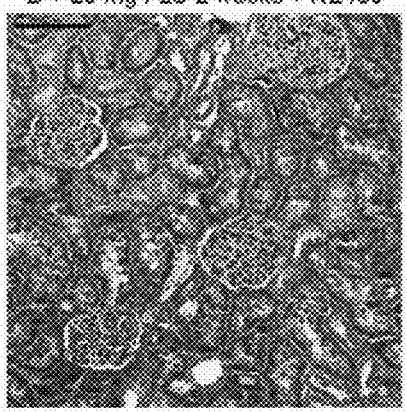
Figure 6F:
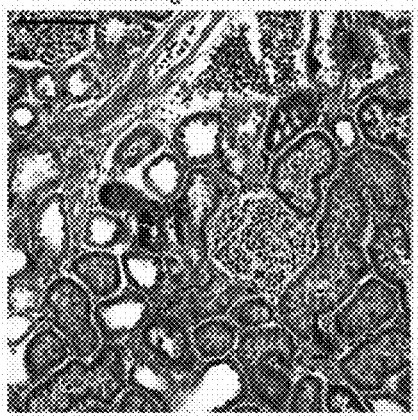
Figure 6G:
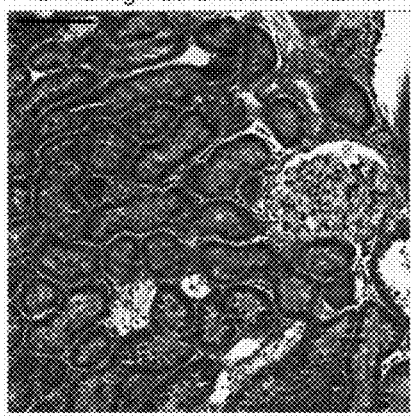
Figure 6H:
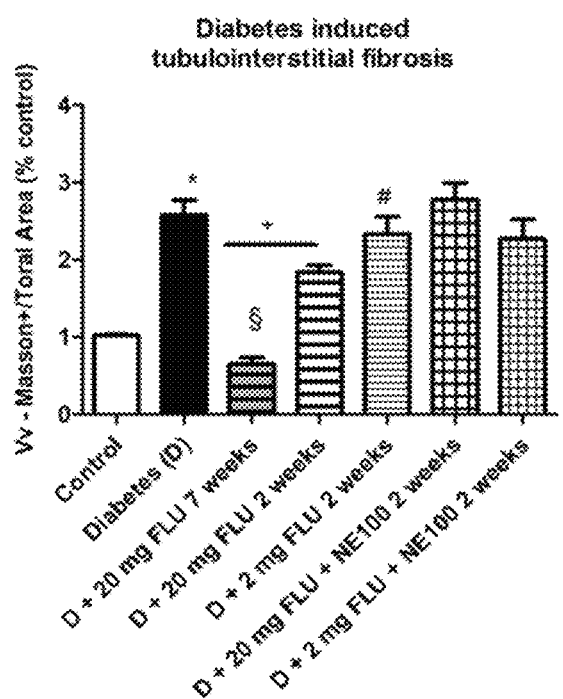

Example 7—Sigma-1 Receptor (S1R) Agonist Compound Fluvoxamine Diminishes Diabetes Induced Renal Interstitial Fibrosis The rat model used was the same as in Example 6. To evaluate the fibrotic lesion of diabetic kidney, paraffin embedded tissue sections of rat kidneys were stained with Masson's trichrome reagent. Diabetes induced development of tubulointerstitial fibrosis (FIG. 6B) is marked by the light blue or light grey regions. Fluvoxamine treatment ameliorated the diabetes induced tubulointerstitial fibrosis (FIGS. 6C, 6D and 6F). Specifically the long-term (7-weeks) treatment restored almost the normal renal structure (FIG. 6C). The co-administration of the S1R specific antagonist NE-100 inhibited the protective effect of fluvoxamine in rats treated with 20 mg fluvoxamine (FIG. 6E). The results are summarized on the column diagram on FIG. 6H.

TABLE 2

Renal parameters of control, diabetic and diabetic rats treated with the S1R agonist fluvoxamine

|  | Control | Diabetes (D) | D7FLU | D + FLU | D + FLU2 |
|---|---|---|---|---|---|
| Blood Glucose (mmol/L) | 17.3 ± 0.95 | 46.6 ± 2.85* | 50.31 ± 3.7 | 36.6 ± 2.62§ | 26.45 ± 3.11§ |
| Fructosamine (μmol/L) | 152 ± 11.0 | 254 ± 8.52* | 276 ± 11.2§ | 252 ± 18.5 | 242 ± 12.8 |
| Blood Urea Nitrogen (mmol/L) | 7.06 ± 0.19 | 26.6 ± 2.42* | 17.3 ± 1.49§ | 17.3 ± 2.30§ | 18.8 ± 1.68§ |
| Blood Creatinine (μmol/L) | 22.0 ± 0.93 | 42.0 ± 2.39* | 27.0 ± 2.24§ | 34.5 ± 2.74§ | 31.8 ± 2.94§ |
| GFR (mL/min/100 g) | 12.8 ± 0.57 | 3.15 ± 0.20* | 6.77 ± 1.15§ | 3.73 ± 0.49 | 4.73 ± 0.69 |
| FeNa (%) | 0.22 ± 0.02 | 3.12 ± 0.75* | 0.40 ± 0.03§ | 0.90 ± 0.23§ | 0.62 ± 0.12§ |
| Urinary albumin excretion (mg/mL) | 3.25 ± 2.39 | 42.5 ± 6.38* | 20.8 ± 9.51§ | 21.5 ± 4.99§ | 24.3 ± 5.77 |

Table 2 shows renal function parameters of Streptozotocin-(65 mg/bwkg iv.) induced type 1 diabetic rats treated per os with (D): vehicle (isotonic saline); (D7FLU): fluvoxamine (20 mg/bwkg/day) for 7 weeks or (D+FLU): fluvoxamine (20 mg/bwkg/day) for 2 weeks from the $5^{th}$ week of diabetes or (D+FLU2): fluvoxamine (2 mg/bwkg/day) for 2 weeks from the $5^{th}$ week of diabetes. GFR-glomerular filtration rate, FeNa: fractional sodium excretion. *$p \leq 0.05$ vs. Control; § $p \leq 0.05$ vs. Diabetes (n=8-10 group, Mean±SEM).

Example 8—Sigma-1 Receptor (S1R) Agonist Compound Fluvoxamine Compound Treatment Decreases Diabetes Induced Mesangial Matrix Expansion in the Kidney of Diabetic Rats The rat model used was the same as in Example 6. Paraffin embedded tissue sections of rat kidneys were stained with PAS. The increase of PAS positive (dark purple or dark grey) area showed a significantly more robust mesangial matrix

TABLE 3

Renal parameters of diabetic rats and diabetic rats treated with either only S1R agonist fluvoxamine, or with the S1R agonist fluvoxamine + antagonist NE-100.

Figure 7A:
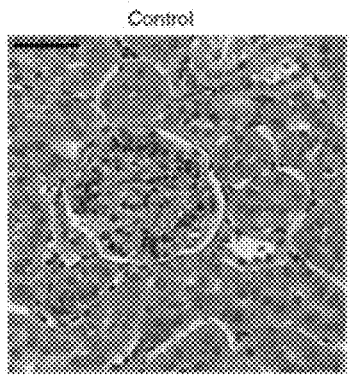
FIGS. 7A-H show the development of mesangial matrix expansion in the kidney sections of Streptozotocin-(65 mg/bwkg iv.) induced type 1 diabetic rats treated per os with (D): vehicle (isotonic saline); D+7FLU fluvoxamine (20 mg/bwkg/day) for 7 weeks or (D+FLU): fluvoxamine (20 mg/bwkg/day) for 2 weeks from the $5^{th}$ week of diabetes,) or (D+FLU2): fluvoxamine (2 mg/bwkg/day) for 2 weeks from the $5^{th}$ week of diabetes. Additional groups were also treated per os with NE-100, a specific antagonist of S1R; (D+FLU+NE-100): fluvoxamine+NE-100 (20 mg/bwkg/day+1 mg/bwkg/day) for two weeks or (D+FLU2+NE-100): fluvoxamine+NE-100 (2 mg/bwkg/day+1 mg/bwkg/day) for two weeks from the $5^{th}$ week of diabetes. Kidney sections were stained with PAS reagent and mesangial fractional volume values (Vv) are defined by the ratio of mesangial area/glomerular tuft area. The mesangial area is determined by assessment of PAS-positive and nucleus-free areas in the mesangium (Bars represent Mean±SEM, n=8-10/group, 20× magnification; scale bar—50 μm). Specifically.
Figure 7B:
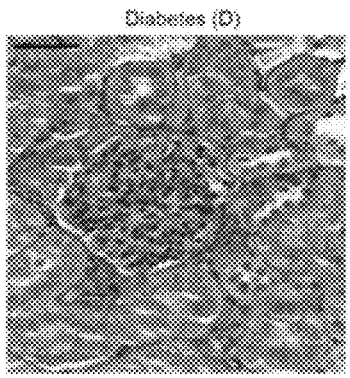
Figure 7C:
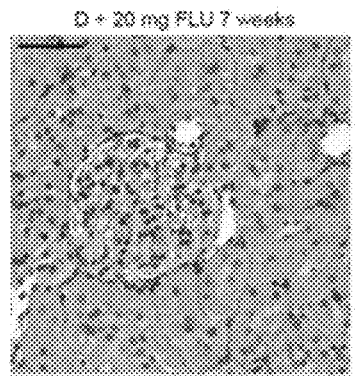
Figure 7D:
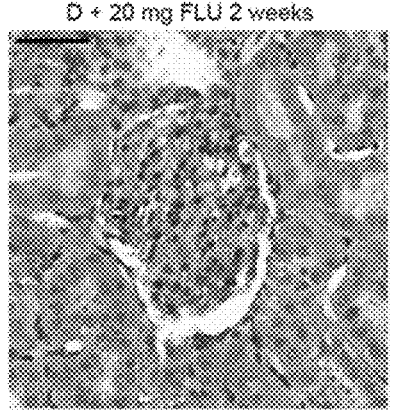
Figure 7E:
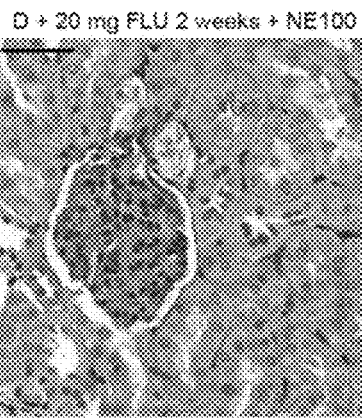
Figure 7F:
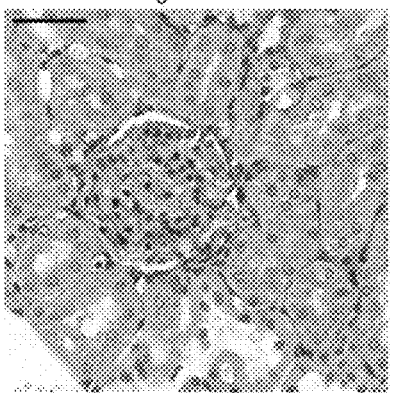
Figure 7G:
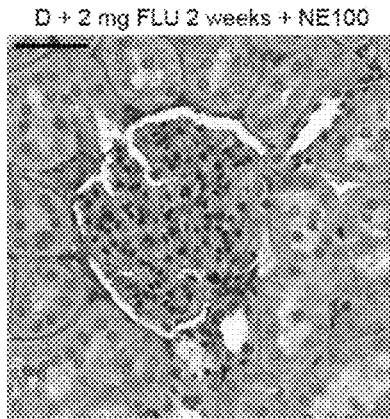
Figure 7H:
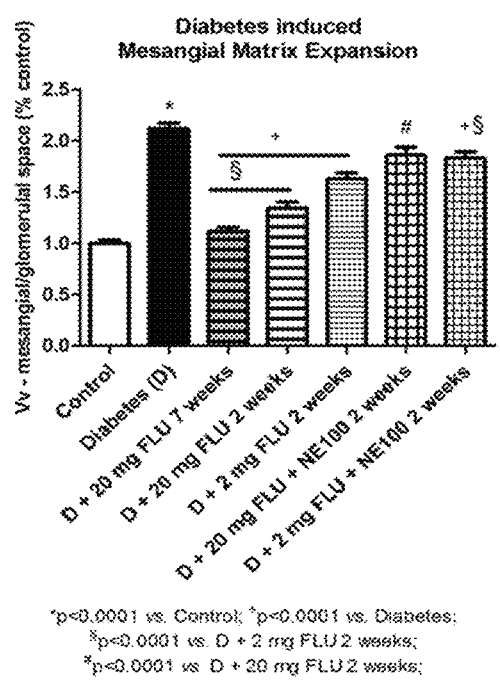
Figure 8A:
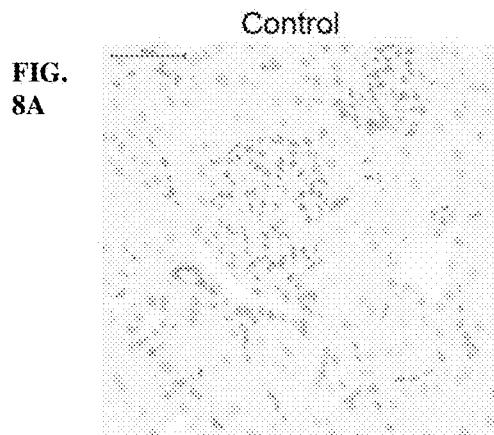
FIGS. 8A-E show fibronectin accumulation in the kidney sections of Streptozotocin-(65 mg/bwkg iv.) induced type 1 diabetic rats treated per os with (D): vehicle (isotonic saline); or (D+FLU): fluvoxamine (20 mg/bwkg/day) for 2 weeks from the 5$^{th}$ week of diabetes) or with (D+FLU+NE-100): fluvoxamine+specific S1R antagonist NE-100 (20 mg/bwkg/day+1 mg/bwkg/day) for two weeks from the 5$^{th}$ week of diabetes. Kidney sections were stained for fibronectin and the positive area/glomeruli was calculated for the sections (Bars represent Mean±SEM, n=8-10/group, 20× magnification; scale bar—50 μm). Specifically.
Figure 8B:
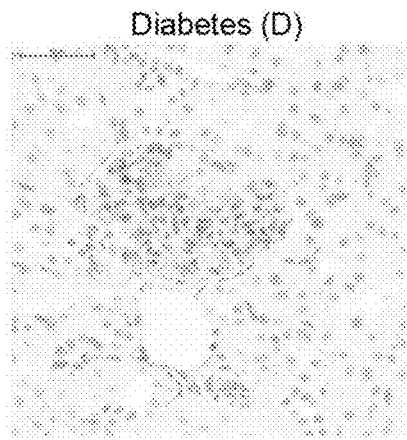
Figure 8C:
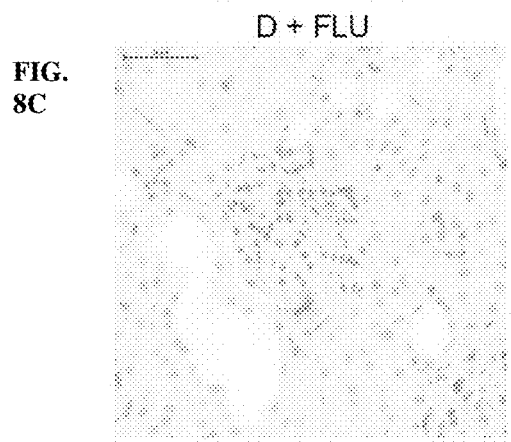
Figure 8D:
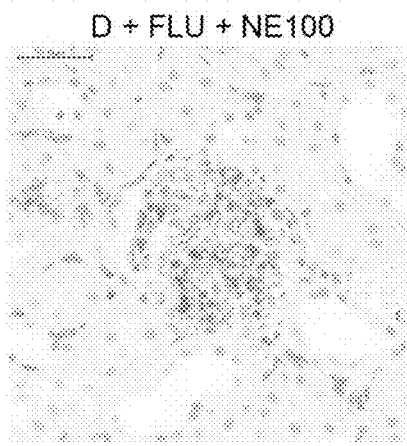
Figure 8E:
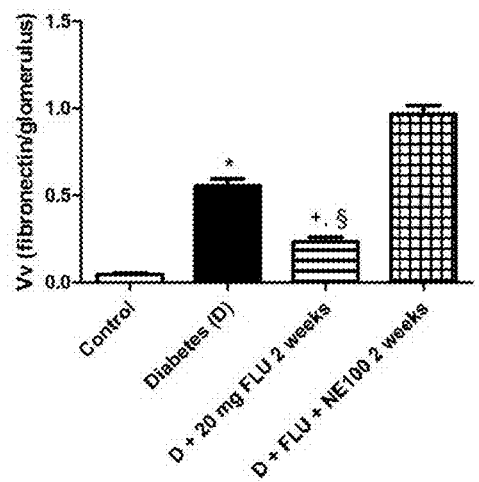

|  | Diabetes (D) | D + FLU | D + FLU + NE-100 | D + FLU2 | D + FLU2 + NE-100 |
|---|---|---|---|---|---|
| Blood Glucose (mmol/L) | 46.6 ± 2.85 | 36.6 ± 2.62§ | 48.5 ± 2.40$ | 26.45 ± 3.11§ | 40.8 ± 3.00# |
| Fructosamine (μmol/L) | 254 ± 8.52 | 252 ± 18.5 | 267 ± 7.66 | 242 ± 12.8 | 264 ± 11.1 |
| Blood Urea Nitrogen (mmol/L) | 26.6 ± 2.42 | 17.3 ± 2.30§ | 24.3 ± 2.27$ | 18.8 ± 1.68§ | 22.3 ± 1.43 |
| Blood Creatinine (μmol/L) | 42.0 ± 2.39 | 34.5 ± 2.74§ | 37.0 ± 4.39 | 31.8 ± 2.94§ | 40.0 ± 3.72 |
| GFR (mL/min/100 g) | 3.15 ± 0.20 | 3.73 ± 0.49 | 3.25 ± 0.25 | 4.73 ± 0.69 | 4.06 ± 0.58 |
| FeNa (%) | 3.12 ± 0.75 | 0.90 ± 0.23§ | 1.33 ± 0.39 | 0.62 ± 0.12§ | 0.96 ± 0.12 |
| Urinary albumin excretion (mg/mL) | 42.5 ± 6.38 | 21.5 ± 4.99§ | 73.3 ± 15.8$ | 24.3 ± 5.77 | 42.8 ± 7.92# | expansion in diabetic animals compared to controls (FIG. 7B). Similarly to tubulointerstitial fibrosis the extent of mesangial matrix expansion was remarkably diminished by all doses of fluvoxamine (FIGS. 7C, 7D and 7F). Long-term (7-weeks) treatment was the most effective in preventing renal tissue damage (FIG. 7C). The co-administration of the S1R specific antagonist NE-100 prohibited the renoprotection of fluvoxamine (FIGS. 7E and 7G) suggesting a directly S1R mediated effect. The results are summarized on the column diagram on FIG. 7H.

Example 9—Sigma-1 Receptor (S1R) Agonist Compound Fluvoxamine Treatment Decreases Diabetes Induced Fibronectin Accumulation in the Kidney of Diabetic Rats The development of fibrosis in diabetic rats (see the chapter "Rat model of streptozotocin (STZ) induced diabetic nephropathy") was confirmed by fibronectin staining as well (FIG. 8). In fluvoxamine treated rats the fibrotic lesion (brown area or darker-medium grey area) is smaller (FIG. 8C) than in diabetic rats (FIG. 8B), and again the S1R antagonist NE-100 suspended this beneficial effect (FIG. 8D). The results are summarized on the column diagram of FIG. 8E.

Example 10—Sigma-1 Receptor (S1R) Agonist Compound Fluvoxamine Decreases Diabetes Induced Extracellular Matrix (ECM) Production in the Kidney of Diabetic Rats The rat model used was the same as in Example 6. ECM components in the kidney tissue sections were determined by Sirius Red staining (FIG. 9). Diabetes induced excessive ECM accumulation (as seen in FIG. 9B), was significantly reduced by the long term 7-weeks fluvoxamine treatment (FIG. 9C).

Figure 10:
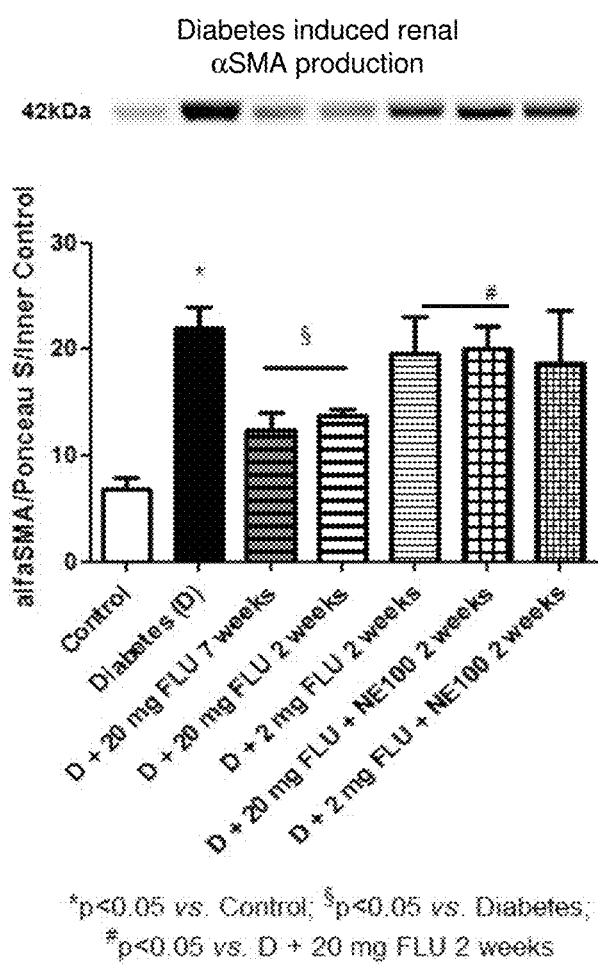

Example 11—Sigma-1 Receptor (S1R) Agonist Compound Fluvoxamine Treatment Decreases Diabetes Induced Alpha Smooth Muscle Actin (αSMA) Protein Level in the Kidney of Diabetic Rats Diabetes induces proliferation and ECM production of myofibroblasts in the kidney, which can be investigated also by the measurement of the protein level of αSMA, a typical marker of myofibroblast. As seen in FIG. 10 αSMA increased by 300% in diabetic rats compared to controls. Fluvoxamine treatment, (predominantly the dose of 20 mg) reduced αSMA protein level by the half. The beneficial effect of fluvoxamine was suspended by the co-administration of the S1R specific antagonist NE-100.

Example 12—Sigma-1 Receptor (S1R) Agonist Compound Fluvoxamine Treatment Minimizes Tubulointerstitial Fibrosis in the Kidney after Unilateral Ureteral Obstruction (UUO)

To confirm the anti-fibroproliferative effect in other models of progressive fibrosis, fluvoxamine was administered to mice with unilateral ureter obstruction (UUO) that is the gold-standard animal model of fibrosis (FIG. 11). The model used is described in the chapter "Mice model of unilateral ureteral obstruction (UUO) induced renal fibrosis". A serious tubulointerstitial fibrosis was induced by the ureter obstruction and fluvoxamine treatment decreased tubulointerstitial fibrosis (FIG. 11B-11C). Similar to diabetic rats, in mice NE-100, the specific S1R antagonist, suspended the beneficial effect of fluvoxamine (FIG. 11D). The results are summarized on the column diagram on FIG. 11E.

Example 13—Sigma-1 Receptor (S1R) Agonist Compound Fluvoxamine Treatment Minimizes Alpha Smooth Muscle Actin (αSMA) Production in the Kidney after Unilateral Ureteral Obstruction (UUO)

Figure 12:
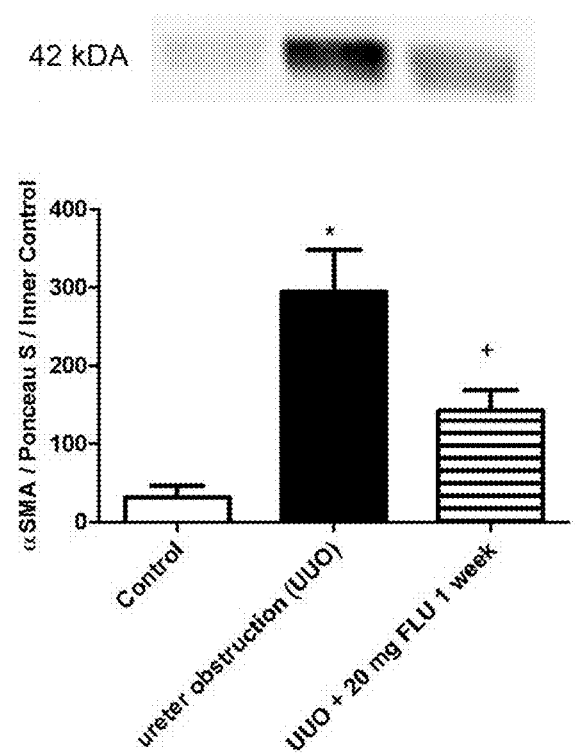
FIG. 12. Sigma-1 receptor (S1R) agonist compound fluvoxamine treatment minimizes α-smooth muscle actin (αSMA) production in the kidney after unilateral ureteral obstruction (UUO).

The mice model used was the same as in Example 12. One week after the induction of UUO the protein amount of αSMA was six times higher in UUO mice than in controls (FIG. 12). One week fluvoxamine treatment successfully decreased UUO-induced αSMA production in mice, which suggest a significant anti-fibroproliferative effect of fluvoxamine treatment even in the long-term.

Figure 13:
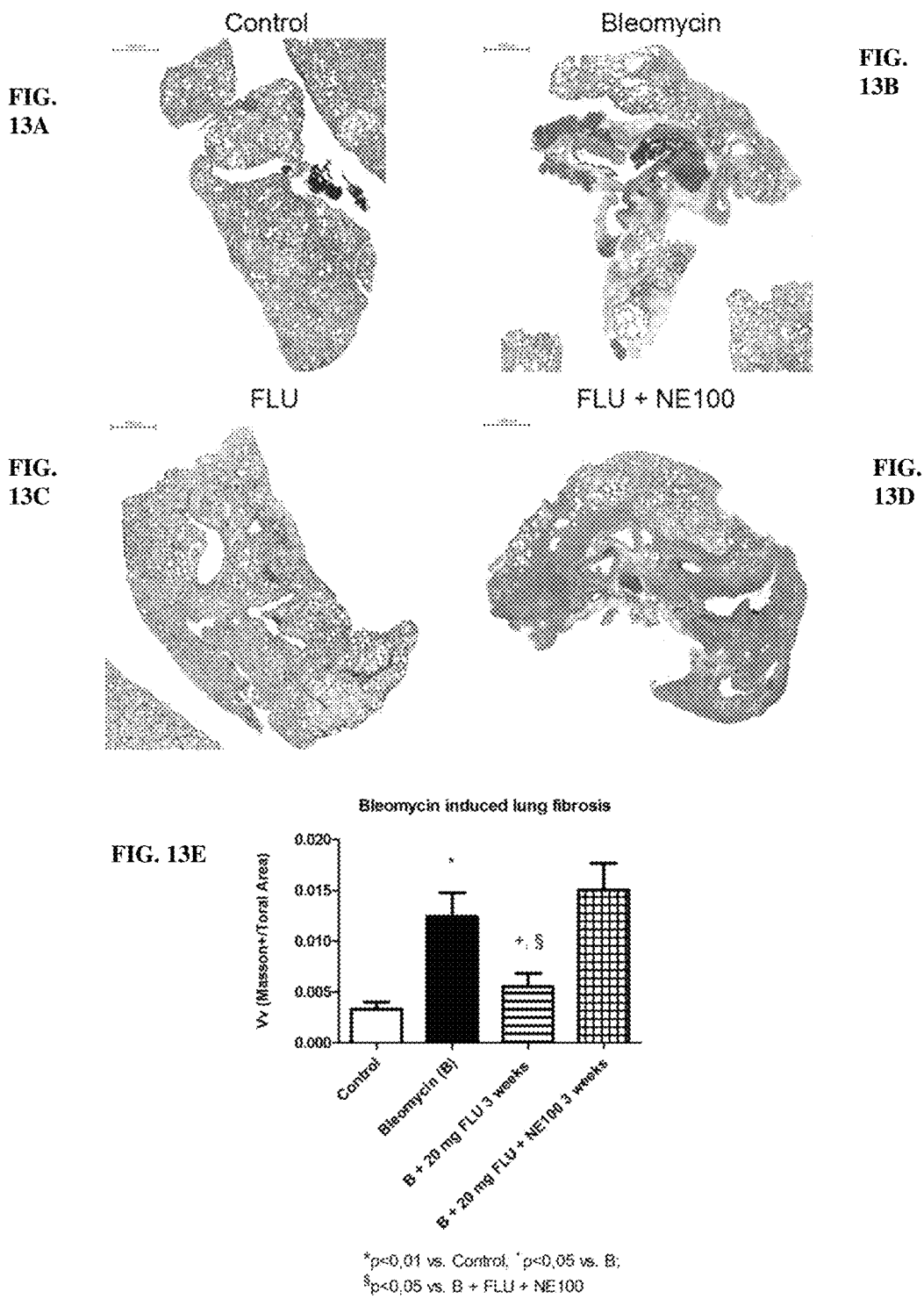
FIGS. 13A-E. S1R agonist compound fluvoxamine treatment ameliorates interstitial fibrosis of the lung in a rat model of bleomycin-induced lung fibrosis.

Example 14—Sigma-1 Receptor (S1R) Agonist Compound Fluvoxamine Treatment Ameliorates Interstitial Fibrosis of the Lung in a Rat Model of Bleomycin-Induced Lung Fibrosis To prove the beneficial anti-fibroproliferative effect of fluvoxamine also in other organs, fluvoxamine was tested in the progressive fibrosis of the lung in the rat model of bleomycin-induced lung fibrosis described in chapter "Rat model of bleomycin-induced pulmonary fibrosis", (FIG. 13). While fibrotic lesions of the lung (marked by light blue or continuous medium grey area FIG. 13B) significantly increased after bleomycin treatment compared to controls; fluvoxamine prevented almost totally the fibrotic effect of bleomycin (FIG. 13C). S1R antagonist NE-100 suspended the effect of fluvoxamine (FIG. 13D). The results are summarized on the column diagram on FIG. 13E.

Figure 14:
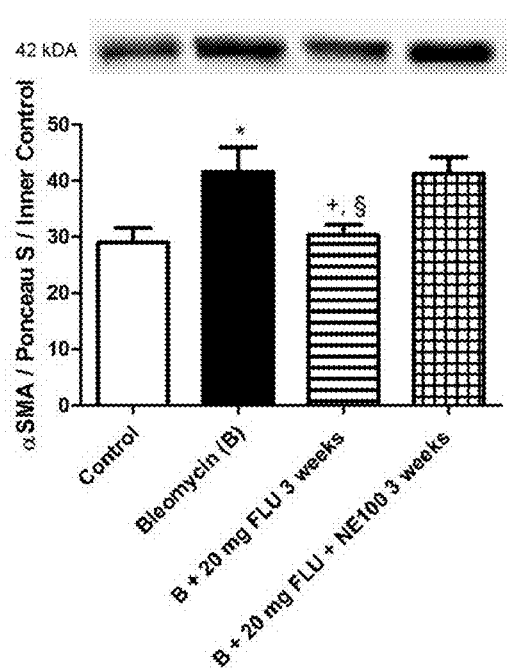
FIG. 14 demonstrates the protein level of αSMA in lung homogenates of rats treated with vehicle (with or without sham operation) or with fluvoxamine (20 mg/bwkg/day) or with fluvoxamine+S1R antagonist NE-100 (1 mg/bwkg/day) for three weeks after the intratracheal injection of bleomycin. (Bars represent Mean±SEM, n=6/group). Upper panel shows representative picture of western blot of αSMA.

Example 15—Sigma-1 Receptor (SIR) Agonist Compound Fluvoxamine Treatment Diminishes αSMA Production in a Rat Model of Bleomycin-Induced Lung Fibrosis The rat model used was the same as in Example 14. Three weeks after the intrathecal injection of bleomycin αSMA protein level was significantly increased in the lung compared to controls (FIG. 14). Fluvoxamine treatment successfully reduced bleomycin-induced αSMA production nearly to the level of controls. Similar to previous results the S1R antagonist NE-100 suspended the beneficial effect of fluvoxamine, which underlines the S1R-mediated antiproliferative effect of fluvoxamine also in other organs, e.g. in the lung.

Example 16—Sigma-1 Receptor (S1R) Agonists Suspend Platelet-Derived Growth Factor (PDGF)-Induced Cell Proliferation in Human Trabecular Meshwork-5 (HTM-5) Cells Human trabecular meshwork-5 (HTM-5) cells were cultured and MTT cell proliferation assay was carried out as described in Materials and Methods. Briefly, the HTM-5 cells were plated in 96 well plates at a density of 40 000 cells/well and treated with a pro-fibrotic substance, PDGF, in the absence or presence of Sigma-1 receptor agonists fluvoxamine (FLU), SA-4503 and PRE-087 for 24 h. Control cells were treated with vehicle (HCl) alone. Thus, in this eye fibrosis model the inventors studied whether Sigma-1 receptor agonists of very different chemical structure are able to reduce artificially elicited progressive fibrosis.

After the treatment period cells were incubated with methyl-thiazoletetrazolium (MTT) for 4 h followed by solubilisation in DMSO-ethanol (1:1) to measure the level of fibrotic proliferation. The formation of water-insoluble formazan was determined by measuring optical density at 570 nm.

The results are shown in FIG. 15.

It can be seen that in a dose-dependent manner each of the three Sigma-1 receptor (SIR) agonists has reduced fibrotic proliferation to the level or even below the level of control cells.

Statistical analysis was carried out as described in the Materials and Methods throughout the Examples.

Example 17—SIR Receptor Agonist Fluvoxamine Reduces Fibrotic Markers in HTM-5 Cells The aim of this experiment was to measure the mRNA expression level of fibrotic markers, i.e. cellular matrix elements fibronectin (FN1), collagenIal (COL1A1) and matrix metalloproteinase 2 (MMP2) in the HTM-5 eye fibrosis model and the effect of S1R agonists effect on progressive fibrosis characterized by these markers.

Human trabecular meshwork-5 (HTM-5) cells were cultured and reverse transcription polymerase chain reaction (RT-PCR) was carried out as described in the Materials and Methods. Briefly, total RNA was extracted, qualitatively and quantitatively characterized and subjected to reverse transcription. The expression levels were measured by real-time quantitative PCR (qPCR) by SYBR green detection. Primer sequences were based on nucleotide sequences from National Center for Biotechnology Information's nucleotide database. The mRNA expression of interest was normalised against mRNA expression of 18S ribosomal RNA (RN18S) from the same samples as internal control.

FIG. 16 shows that fluvoxamine inhibit the expression of each fibrosis marker tested in a dose dependent manner.

Example 18. Effect of PDGF and S1R Agonist FLU on Actin Cytoskeleton Rearrangement in HTM-5 Cells In this example of the eye fibrosis model of human trabecular meshwork-5 (HTM-5) cells, treated with PDGF, F-actin were immunostained to visualize morphological changes/cytoskeleton rearrangements of HTM-5 cells caused by PDGF.

Cells were cultured and plated in serum-free media as described in the Materials and Methods. Cells were treated with PDGF or FLU or both, washed, fixed and permealized and blocked. This preparation and repeated washes with PBS were followed by staining with phalloidin-Alexa-Fluor 546 for F-actin and with Hoechst dye for DNA to show nuclei. Images were made as described in Materials and methods in various magnifications and are shown in FIG. 17 (magnification: 1000×) and FIG. 18 (magnification: 6000×) The results clearly show that in the present eye fibrosis model fibrotic rearrangement and active production of actin filaments (see FIGS. 17B and 18B), a hallmark of progressive fibrosis, are blocked by S1R agonist fluvoxamine (see FIGS. 17C and 18C) to a level similar that of the control (see FIGS. 17A and 18A),

REFERENCES

Armendariz-Borunda J et al. Gut 55(11), 1663-1665 (2006)
Azuma A. Expert Review of Respiratory Medicine 4(3), 301-310 (2010)
Berardi F et al. Bioorg. Med. Chem. 9(5), 1325-35 (2001)
Díez J, Circ J. 72, A:A8-12 (2008)
Farris A B, United States and Canadian Academy of Pathology Annual Meeting (2012)
Friedlander, Martin. Fibrosis and diseases of the eye Clin Invest. 2007 Mar. 1; 117(3): 576-586.
Griesmaier E et al. Experimental Neurology 237(2), 388-395 (2012)
Hanner M et al. Proc Natl Acad Sci USA. 93(15). 8072-8077 (1996)
Hill, Lisa J, Neural Regen Res. 2016 June; 11(6): 922-923.
Hill S J, Thesis (2012)
Hinz B. Curr, Reumatol Reports (2009)
Hinz. B et al. F1000 Biol Rep., 2:78 (2010)
Hutchinson et al. BBA 1832, 962-971 (2013)
Ishikawa M et al. Journal of Receptor, Ligand and Channel Research 3, 25-3 (2010)
Janna K et al. Nature Rev Mol Cell Biol 15, 771-785 (2014)
Karihaloo A. Curr Diab Rep. 12(4), 414-22 (2012)
Klingberg F et al. J Pathol. 229(2), 298-309 (2013)
Lee W J et al. Br J Dermatol. 165(3), 673-7 (2011)
Lee, Wen-Cherng et al. WO 03/087304A2
Lekkerkerker S et al. Curr Pharm Des. 18(27), 4093-102 (2012)
M E Cho et al. Expert Opin Investig Drugs. 19(2), 275-283 (2010)
Maksumova L. and Unwin D. H WO 2010/048716
McDonnell, Fiona et al. The Role of Epigenetics in the Fibrotic Processes Associated with Glaucoma.
Journal of Ophthalmology Volume 2014, Article ID 750459, 13 pages Miller Charles G et al. (2016) Experimental Biology and Medicine 242(1), 1-7
Okuyama S et al. CNS Drug Rev. 2(2), 226-237 (1999)
Patel Ashaben. Ocular drug delivery systems: An overview. World J Pharmacol. 2013; 2(2): 47-64.
Paz Z et al. Clin Rev Allergy Immunol. 38(2-3), 276-286 (2010)
Paz Z et al. Rev Allerg Immunol 38, 276-286 (2010)
Pellicoro et al. Nature Reviews Immunology 14, 181-194 (2014)
Raghu et al. Am J Respir Crit Care Med 183, 788-824 (2011)
Rieder et al. Curr Opin Gastroenterol. July; 24(4), 462-8 (2008)
Rong Xu et al. Bioorganic & Medicinal Chemistry 23(1), 222-230 (2015)
Rossi D et al. Bioorganic & Medicinal Chemistry 19(21), 6210-6224 (2011)
Schaefer C J et al. Eur Respir Rev 20(120), 85-97 (2011)
See F. Heart Lung Circ. 22(2), 122-132 (2013)
Stamer W. Daniel et al. The many faces of the trabecular meshwork cell Exp Eye Res. 2017 158 112-123.
Shimizu K. et al. EP 1548008
Zhavoronkov, Alex et al. Pro-fibrotic pathway activation in trabecular meshwork and lamina cribrosa is the main driving force of glaucoma Cell Cycle. 2016; 15(12): 1643-1652
Zuber K et al. JAAPA. 26(10), 19-25 (2013)
Yu-Wai-Man Cynthia Personalized Medicine in Ocular Fibrosis: Myth or Future Biomarkers. Adv Wound Care (New Rochelle). 2016 Sep. 1; 5(9): 390-402.

The invention claimed is:

1. A method for the treatment of progressive fibrosis in a progressively fibrotic eye tissue of a subject by preventing, reversing or inhibiting fibrotic remodeling of the extracellular matrix, said method comprising administering to the subject an S1R agonist compound in an effective amount sufficient for preventing, reversing or inhibiting fibrotic remodeling of the extracellular matrix to an area of the eye affected by progressive fibrosis, said S1R agonist compound having the following formula II:

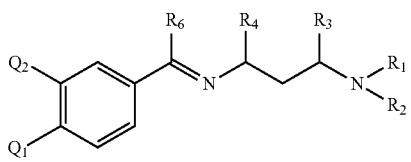

wherein $Q_1$ is a Cl or F or a methyl-halogen selected from $CH_2F$, $CHF_2CF_3$, $CH_2C_1$, $CHCl_2$, $CCl_3$, or a methoxy $Q_2$ is H, Cl or F, $R_6$ is selected from a substituted or unsubstituted C(1-6) alkyl, C(1-6) alkoxy, C(1-6) alkoxy C(1-6) alkyl, C(5-10) aryl, Y is CH or O, wherein if Y is O then $R_4$ is not present, if Y is CH then $R_4$ is H, methyl or ethyl, $R_3$ is H, methyl or ethyl, or $R_3$ and $R_4$ together with the Y-C2 alkyl moiety which they are attached to, may form a saturated or partially unsaturated cyclic group comprising 0 to 2 heteroatom(s) or $R_4$ and $R_3$ together form a C(2-4) alkyl bridge, $R_1$ and $R_2$ are independently H, methyl or ethyl, or a pharmaceutically acceptable salt thereof.

2. The method according to claim 1 wherein $Q_1$ is a methyl-halogen selected from $CHF_2$, $CF_3$, $CHCL_2$ or $CCL_3$, $Q_2$ is H, $R_6$ is selected from a substituted or unsubstituted C(1-6) alkoxyalkyl (or C(1-6) dialkyl-ether) or C(1-2) alkoxy C(2-5) alkyl, Y is CH or O, wherein if Y is O then $R_4$ is not present, if Y is CH then $R_4$ is H, methyl or ethyl, $R_3$ is H or methyl.

3. The method according to claim 1 wherein said compound is fluvoxamine.

4. The method according to claim 1 wherein the subject has a fibroproliferative eye disorder.

5. The method according to claim 4 wherein said fibroproliferative eye disorder is an eye disease in the anterior segment of the eye.

6. The method according to claim 4 wherein said fibroproliferative eye disorder is glaucoma.

7. The method according to claim 6 wherein glaucoma is selected from the group consisting of open angle glaucoma, closed angle glaucoma, primary glaucoma and secondary glaucoma.

8. The method according to claim 4 wherein said fibroproliferative eye disorder is an eye disease related with a fibrosis in the trabecular meshwork.

9. The method according to claim 1 wherein said S1R agonist is administered in a formulation of eye drops.

10. The method according to claim 1 wherein said S1R agonist is administered in a formulation of ointment.

11. The method according to claim 2 wherein the subject has a fibroproliferative eye disorder which is glaucoma and said S1R agonist is administered in a formulation of eye drops.

* * * * *

UNITED STATES PATENT AND TRADEMARK OFFICE
CERTIFICATE OF CORRECTION

PATENT NO. : 10,842,794 B2
APPLICATION NO. : 16/360375
DATED : November 24, 2020
INVENTOR(S) : Fekete et al.

Page 1 of 1

It is certified that error appears in the above-identified patent and that said Letters Patent is hereby corrected as shown below:

In the Claims

Claim 1, Column 59, Lines 14-21, delete

" 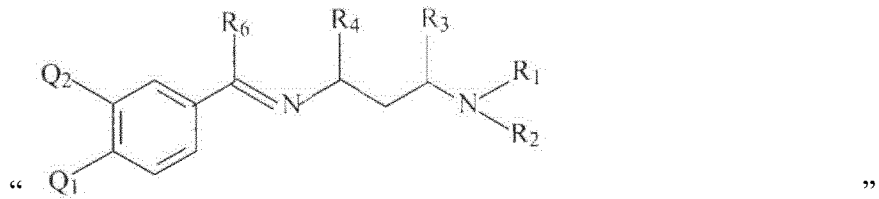 (II) "

and substitute therefor – 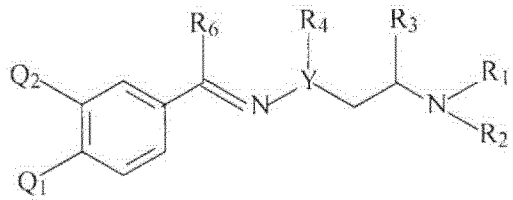 (II) –.

Claim 1, Column 59, Line 25, delete "$CH_2C_1$" and substitute therefor – $CH_2Cl$ –.

Claim 2, Column 60, Line 2, delete "$CHCL_2$" and substitute therefor – $CHCl_2$ –.

Claim 2, Column 60, Lines 3, delete "$CCL_3$" and substitute therefor – $CCl_3$ –.
$Cl_2$ –.

Signed and Sealed this
Tenth Day of August, 2021

Drew Hirshfeld
*Performing the Functions and Duties of the
Under Secretary of Commerce for Intellectual Property and
Director of the United States Patent and Trademark Office*